(12) United States Patent
Li et al.

(10) Patent No.: US 9,187,454 B2
(45) Date of Patent: Nov. 17, 2015

(54) INHIBITORS OF KINASES AND CANCER STEM CELLS, AND METHODS OF PREPARATION AND USE THEREOF

(71) Applicant: Boston Biomedical, Inc., Cambridge, MA (US)

(72) Inventors: Chiang Jia Li, Cambridge, MA (US); Ji-Feng Liu, Winchester, MA (US); Wei Li, Wayland, MA (US); Amanda Gibeau, Natick, MA (US); Harry Rogoff, Wrentham, MA (US)

(73) Assignee: Boston Biomedical, Inc., Cambridge, MA (US)

( * ) Notice: Subject to any disclaimer, the term of this patent is extended or adjusted under 35 U.S.C. 154(b) by 0 days.

(21) Appl. No.: 14/208,170

(22) Filed: Mar. 13, 2014

(65) Prior Publication Data

US 2014/0275033 A1    Sep. 18, 2014

Related U.S. Application Data

(60) Provisional application No. 61/780,248, filed on Mar. 13, 2013.

(51) Int. Cl.
  *C07D 417/14* (2006.01)
  *C07D 487/04* (2006.01)
  *C07D 471/04* (2006.01)
  *C07D 403/06* (2006.01)
  *C07D 409/14* (2006.01)

(52) U.S. Cl.
  CPC ............ *C07D 403/06* (2013.01); *C07D 409/14* (2013.01); *C07D 417/14* (2013.01); *C07D 471/04* (2013.01); *C07D 487/04* (2013.01)

(58) Field of Classification Search
  CPC ... C07D 471/14; C07D 487/04; C07D 471/04
  USPC .......................... 548/469, 486; 514/415, 418
  See application file for complete search history.

(56) References Cited

U.S. PATENT DOCUMENTS

| 7,026,330 | B2 * | 4/2006 | Grupp et al. .................. 514/291 |
| 7,176,234 | B2 * | 2/2007 | Cai et al. ........................ 514/450 |
| 7,342,016 | B2 * | 3/2008 | Zhu et al. ................. 514/253.04 |
| 2006/0094674 | A1 * | 5/2006 | Neel et al. ........................ 514/44 |
| 2014/0275076 | A1 | 9/2014 | Tsuboi et al. |

FOREIGN PATENT DOCUMENTS

| WO | 2004000300 | * 12/2003 |
| WO | 2009/033033 A2 | 3/2009 |

OTHER PUBLICATIONS

Guan et al., Bioorganic & Medicinal Chemistry Letters (2004),14(1), 187-190.*

* cited by examiner

*Primary Examiner* — Niloofar Rahmani
(74) *Attorney, Agent, or Firm* — Arent Fox LLP; Yi Liu; Tony K. Uhm

(57) ABSTRACT

The invention provides novel inhibitors of cancer stem cells as well as cancer stem cell pathway kinase and other related kinases, pharmaceutical compositions and uses thereof in the treatment of cancer or a related disorder in a mammal, and methods of making such compounds and compositions.

18 Claims, 1 Drawing Sheet

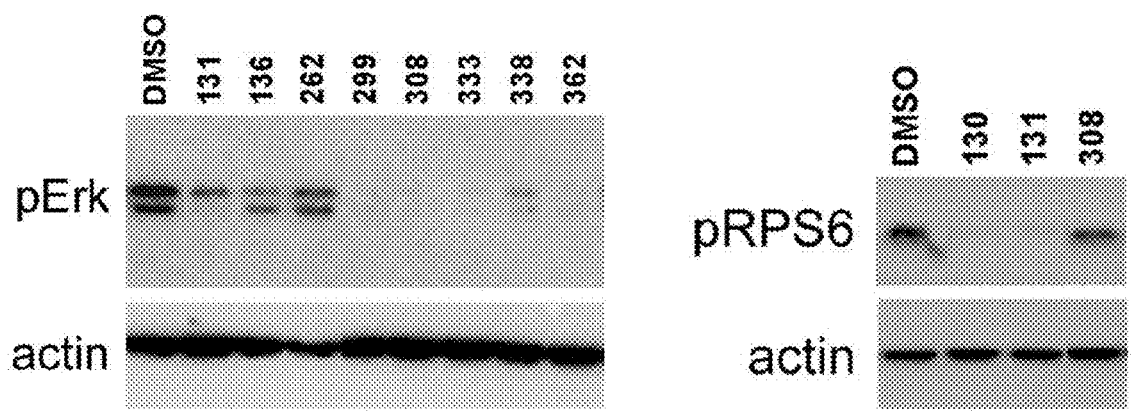

INHIBITORS OF KINASES AND CANCER STEM CELLS, AND METHODS OF PREPARATION AND USE THEREOF

RELATED APPLICATIONS

This application claims the benefit of U.S. Provisional Application No. 61/780,248, filed Mar. 13, 2013. The contents of this application are hereby incorporated by reference in their entirety.

TECHNICAL FIELD OF THE INVENTION

The invention generally relates to inhibitors of cancer stem cells. More particularly, the invention relates to novel inhibitors of cancer stem cells as well as cancer stem cell pathway kinase and other related kinases, to pharmaceutical compositions and uses thereof in the treatment of cancer or a related disorder in a mammal, and to methods of making such compounds and compositions.

BACKGROUND OF THE INVENTION

Despite decades of intensive scientific and clinical research, cancer remains a challenging disease to both the patient and the healthcare provider. In the U.S. alone, it is estimated that there are over 1.5 million new cases of cancer and more than half million of cancer-related deaths in 2011. Worldwide, cancer is the third leading cause of death.

Cancer is characterized by rapidly-proliferating cell growth in the body. Cancer is often able to invade other tissues from its original location and, in a process called metastasis, spread to other parts of the body through blood and lymphatics. There are many types of cancer, which may be classified in pathology and clinical diagnosis into carcinoma, sarcoma, leukemia, lymphoma and myeloma, and malignant tumors of the central nervous system.

At the present time, the leading therapies for cancer include surgery, radiation, and chemotherapy. Surgery and radiotherapy are quite successful in treating primary tumors. However, once a cancer has disseminated to distant sites, chemotherapy is often required to treat the disease. Cytotoxic agents have played a critical role in modern cancer therapy. However, they usually induce substantial toxicity in normal tissues. Targeted therapies that more specifically target cancer cells are more desirable. A relatively new class of agents with selectivity for targets implicated in tumor growth have started to emerge recently, demonstrating impressive efficacy with much less toxicity than cytotoxic agents.

Protein kinases represent potential targets for therapeutic inhibition. (Pyle, et al., 2006 *Nat Biotechnol.* 24(3): p. 344-50.) Protein kinases are a family of enzymes that regulate a wide variety of cellular processes, including cell growth, cell proliferation, cell differentiation and metabolism. A kinase enzyme that modifies other proteins by chemically adding phosphate groups to them in a phosphorylation process. Protein kinases communicate cell growth signals through sequential chemical modification of pathway partners. Therefore, pharmacologic inhibition of any kinase on a given signal transduction cascade would theoretically block communication along the entire pathway. In addition, it is known that protein kinases play a role in disease states and disorders, for example, kinase mutation and/or overexpression are frequently characterized in cancers, resulting in hyperactivated activity that often correlates with uncontrolled cell growth.

Cancer Stem Cells (CSC) is a subpopulation of cells within a variety of tumor types with a tumorigenic potential that is lacking in the rest of the cells within these tumors. CSC can generate tumors through the stem cell processes of self-renewal and differentiation into multiple cell types. There is mounting evidence that such cells exist in almost all tumor types. CSC give rise to the differentiated cells that form the bulk of the tumor mass and phenotypically characterize the disease. Cancer stem cells have been demonstrated to be fundamentally responsible for carcinogenesis, cancer metastasis, and cancer reoccurrence. In many tumors, CSC and their differentiated progeny appear to have markedly different biologic characteristics.

Therapies specifically targeted at CSCs, therefore, hold unique potential for improvement of survival and quality of life of cancer patients, especially for sufferers of metastatic disease. (PCTUS2008075418, WO 2009033033) Conventional therapies that target mature tumor cells may lead to clinical improvement, but are unlikely to be curative unless CSCs are also targeted. Relevant targets unique to the rare cancer stem cells may be missed if clinical activity is judged solely by criteria that reflect the effects of treatment on the bulk of the cancer.

Recent studies have shown that certain compounds inhibit kinases and kill cancer stem cells, demonstrating that kinases are important targets for killing or inhibiting cancer stem cells. These kinases important for CSCs are collectively referred to cancer stem cell pathway kinase (CSCPK) hereinafter. Our results provide a method of targeting cancer stem cells with CSCPK inhibitors.

PDGFRα is a receptor tyrosine kinase (RTK) that is activated after binding to its ligand, PDGF, which contributes to cell proliferation, angiogenesis, and apoptosis. It belongs to class III receptor tyrosine kinase family and are related to the CFS-1 receptor/c-fms and the stem cell growth factor/c-kit proto-oncogene family. PDGFRα pathway is active in early fetal development and reactivated in many cancers, such as hepatocellular cancer (HCC), head and neck cancer, brain tumors, gastrointestinal tumors, skin cancer, prostate cancer, ovarian cancer, breast cancer, sarcoma, and leukemia. (Betsholtz 1995 *Int J Dev Biol* 39(5): p. 817-25; Chott, et al. 1999 *Am J Pathol* 155(4): p. 1271-9; Dabrow, et al., 1998 *Gynecol Oncol* 71(1): p. 29-37; Cools, et al. 2003 *N Engl J Med* 348(13): p. 1201-14; Heinrich, et al., 2003 *Science* 299(5607): p. 708-10; Holtkamp, et al. 2006 *Carcinogenesis* 27(3): p. 664-71; Jackson, et al. 2006 *Neuron* 51(2): p. 187-99; Jechlinger, et al. 2006 *J Clin Invest* 116(6): p. 1561-70; Ongkeko, et al. 2005 *Am J Clin Pathol* 124(1): p. 71-6; Stock, et al. 2007 *Mol Cancer Ther* 6(7): p. 1932-41; Sulzbacher, et al. 2003 *Mod Pathol* 16(1): p. 66-71; Wilczynski, et al. 2005 *Hum Pathol* 36(3): p. 242-9; Zhang, et al. 2005 *Clin Cancer Res* 11(24 Pt 1): p. 8557-63; Westermark, et al. 1993 *Acta Oncol* 32(2): p. 101-5.)

In addition, PDGFRα activation has recently been shown to play a key role in bone metastasis of prostate cancer. (Dolloff, et al. 2005 *Oncogene* 24(45): p. 6848-54; Dolloff, et al. 2007 *Cancer Res* 67(2): p. 555-62.) Furthermore, PDGFRα-p70S6K pathway has been shown to be essential for angiogenesis in vivo. (Tsutsumi, et al. 2004 *Circ Res* 94(9): p. 1186-94.) Specifically targeting PDGFRα using monoclonal antibody has been shown to lead to significant reduction in tumor cell proliferation and survival while being a relatively non-toxic treatment. (Stock, et al. 2007 *Mol Cancer Ther* 6(7): p. 1932-41.) Therefore, PDGFRα represents a target for developing targeted chemotherapy against broad spectrum of cancers with less toxicity.

Other than cancer, it has been well demonstrated that chromosomal rearrangements activate PDGFRα by fusion to FIP1L1, causing idiopathic hypereosinophilic syndrome.

(Cools, et al. 2003 *N Engl J Med* 348(13): p. 1201-14.) In addition, activation of PDGFRα by promoter polymorphisms has linked to neural tube defects including spina bifida, which has been verified by mouse mutant model. (Joosten, et al. 2001 *Nat Genet* 27(2): p. 215-7.) PDGFRα activation has also been linked with fibrosis. (Lasky, et al. 1998 *Am J Respir Crit Care Med* 157(5 Pt 1): p. 1652-7; Ferns, et al. 1991 *Science* 253(5024): p. 1129-32; Johnson, et al. 1992 *J Exp Med* 175 (5): p. 1413-6; Raines, et al. 1989 *Science* 243(4889): p. 393-6.) Thus, PDGFRα is a potential target for anti-fibrotic therapy.

There are continued unmet needs for novel inhibitors of cancer stem cells as well as cancer stem cell pathway kinase and other related kinases and targets.

SUMMARY OF THE INVENTION

The invention provides novel inhibitors of cancer stem cells as well as cancer stem cell pathway kinase and other related kinases and targets, as well as pharmaceutical compositions and uses thereof in the treatment of a cancer or a related disorder in a mammal. The invention also provide synthetic and preparation methods of making such compounds and compositions.

In one aspect, the invention generally relates to a compound of Formula I,

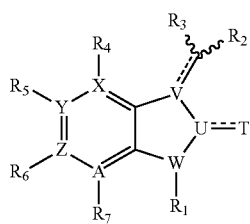

or an enantiomer, diastereomer, tautomer, or pharmaceutically acceptable salt or solvate thereof, wherein
$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;
$R_2$ is monocyclic or bicyclic heterocycle or substituted heterocycle, aryl or substituted aryl;
$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_aR_b$, $S(O)_2NR_aR_b$;
$R_4$, $R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;
T is O, S or $R_a$;
U, V, and W are each independently a carbon, N, O, or S;
X, Y, Z, and A are each independently a carbon or N, with the proviso that the ring in which X, Y, Z, and A exist is aromatic;

with the provision that
one of $R_4$, $R_5$, $R_6$, and $R_7$ is

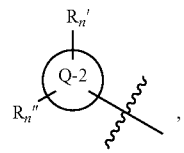

and
$R_4$, $R_5$, $R_6$, or $R_7$ is absent if X, Y, Z, or A, respectively, is a heteroatom;
wherein
Q-2 is a 5- or 6-membered aromatic or non-aromatic ring or ring system optionally having at least one ring carbon atom substituted with a heteroatom selected from N, O and S;
$R_{n'}$ and $R_{n''}$ are each independently hydrogen, halogen, cyano, nitro, trihalomethyl, $OCF_3$, alkyl or substituted alkyl, heterocycle or substituted heterocycle, aryl or substituted aryl, or $OR_a$;
$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;
$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and
$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In another aspect, the invention generally relates to a compound of Formula II,

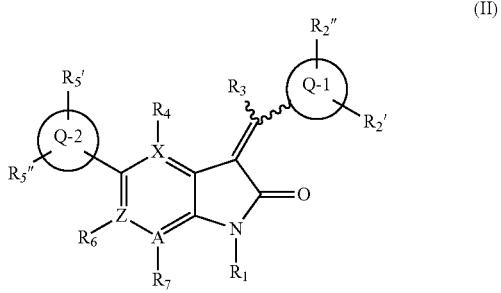

or an enantiomer, diastereomer, tautomer, or pharmaceutically acceptable salt or solvate thereof, wherein
$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;
$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_aR_b$, $S(O)_2NR_aR_b$;
$R_4$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Z, and A are each independently a carbon or N, with the proviso that the ring in which X, Z, and A exist is aromatic;

Q-1 and Q-2 is independently is a 5- or 6-membered aromatic or non-aromatic ring or ring system optionally having at least one ring carbon atom substituted with a heteroatom selected from N, O and S;

$R_{2'}$ and $R_{2''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, $R_{5'}$ and $R_{5'''}$ are each independently hydrogen, halogen, cyano, nitro, $CF_3$, $OCF_3$, alkyl or substituted alkyl, heterocycle or substituted heterocycle, aryl or substituted aryl, or $OR_a$;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In yet another aspect, the invention generally relates to a compound of Formula III,

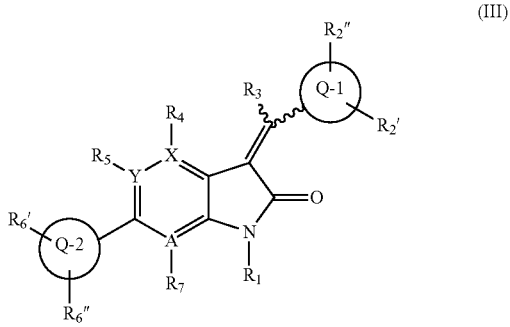

(III)

or an enantiomer, diastereomer, tautomer, or pharmaceutically acceptable salt or solvate thereof, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, $—OR_a$, $—C(O)R_a$, $—C(O)OR_a$, $—NR_aR_b$, $S(O)_2NR_aR_b$;

$R_4$, $R_5$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Y, and A are each independently a carbon or N, with the proviso that the ring in which X, Y, and A exist is aromatic;

Q-1 and Q-2 are each independently is a 5- or 6-membered aromatic or non-aromatic ring or ring system optionally having at least one ring carbon atom substituted with a heteroatom selected from N, O and S;

$R_{2'}$ and $R_{2''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, $R_{6'}$ and $R_{6''}$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In yet another aspect, the invention generally relates to a compound of Formula IV,

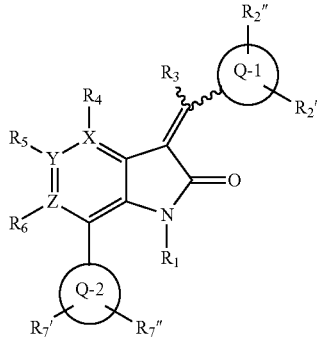

(IV)

or an enantiomer, diastereomer, tautomer, or pharmaceutically acceptable salt or solvate thereof, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, —$OR_a$, —$C(O)R_a$, —$C(O)OR_a$, —$NR_aR_b$, $S(O)_2NR_aR_b$;

$R_4$, $R_5$, and $R_6$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Y, and Z are each independently a carbon or N, with the proviso that the ring in which X, Y, and Z exist is aromatic;

Q-1 and Q-2 are each independently is a 5- or 6-membered aromatic or non-aromatic ring or ring system optionally having at least one ring carbon atom substituted with a heteroatom selected from N, O and S;

$R_{2'}$ and $R_{2''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_b R_c$, $NR_dS(=O)_2NR_bR_c$, $NR_dP(=O)_2NR_bR_c$, $NR_bC(=O)R_a$, or $NR_bP(=O)2R_e$, $R_{7'}$ and $R_{7''}$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In yet another aspect, the invention generally relates to a compound of Formula V

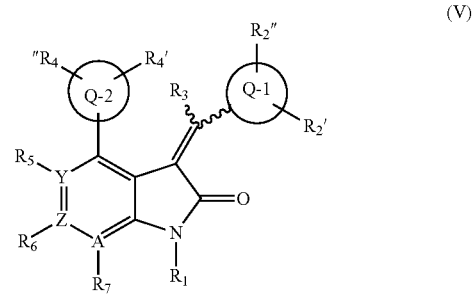

(V)

or an enantiomer, diastereomer, tautomer, or pharmaceutically acceptable salt or solvate thereof, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, —$OR_a$, —$C(O)R_a$, —$C(O)OR_a$, —$NR_aR_b$, $S(O)_2NR_aR_b$;

$R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

Y, Z and A are each independently a carbon or N, with the proviso that the ring in which Y, Z and A exist is aromatic;

Q-1 and Q-2 are each independently is a 5- or 6-membered aromatic or non-aromatic ring or ring system optionally having at least one ring carbon atom substituted with a heteroatom selected from N, O and S;

$R_{2'}$ and $R_{2''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, $R_{7'}$ and $R_{7''}$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In yet another aspect, the invention generally relates to a pharmaceutical composition comprising a compound disclosed herein, or a pharmaceutically acceptable salt, ester or pro-drug thereof, and a pharmaceutically acceptable excipient, carrier, or diluent.

In yet another aspect, the invention generally relates to a method of treating or preventing cancer, or a related disorder or condition thereof in a mammal, including a human, comprising administering to a subject in need thereof a therapeutically effective amount of a pharmaceutical composition comprising a compound disclosed herein, or a pharmaceutically acceptable salt, ester or pro-drug thereof, effective in the treatment or prevention of cancer, or a related disorder or condition thereof in a mammal, including a human, and a pharmaceutically acceptable excipient, carrier, or diluent.

BRIEF DESCRIPTION OF THE DRAWINGS

FIG. 1 shows the kinase inhibition activity of the compounds.

DEFINITIONS

Definitions of specific functional groups and chemical terms are described in more detail below. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties. Throughout the specifications, groups and substituents thereof may be chosen to provide stable moieties and compounds.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "pharmaceutically acceptable salt" refers to either a pharmaceutical acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

The compounds of the present invention may form salts that are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps that may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable ester," refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

As used herein, the term "prodrug" refers to a pharmacological derivative of a parent drug molecule that requires biotransformation, either spontaneous or enzymatic, within the organism to release the active drug. For example, prodrugs are variations or derivatives of the compounds of Formula I that have groups cleavable under certain metabolic conditions, which when cleaved, become the compounds of Formula I. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form.

Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, "$C_x$-$C_y$" refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{20}$" and the likes similarly encompass the various combinations between 1 and 20 (inclusive) carbon atoms, such as $C_1$-$C_6$, $C_1$-$C_{12}$ and $C_3$-$C_{12}$.

As used herein, the terms "alkyl" refers to a straight or branched chain alkane (hydrocarbon) radical. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, $CF_3$, $OCF3$, cycloalkyl, alkenyl, cycloalkenyl, alkynyl, heterocycle, aryl, $OR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle or substituted heterocycle; and $R_e$ is alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted. As used herein, the term "$C_x$-$C_y$ alkyl" refers to a saturated linear or branched free radical consisting essentially of x to y carbon atoms, wherein x is an integer from 1 to about 10 and y is an integer from about 2 to about 20. Exemplary $C_x$-$C_y$ alkyl groups include "$C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc. Of course, other $C_1$-$C_{20}$ alkyl groups will be readily apparent to those of skill in the art given the benefit of the present disclosure.

As used herein, the term "alkenyl" refers to a straight or branched chain hydrocarbon radical having at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substitutents can themselves be optionally substituted.

As used herein, the term "alkynyl" refers to a straight or branched chain hydrocarbon radical having at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substitutents can themselves be optionally substituted.

As used herein, the term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. The exemplary substitutents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the term "cycloalkyl" refers to a fully saturated cyclic hydrocarbon group having from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. The exemplary substitutents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. The exemplary substitutents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) that have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

As used herein, "substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. The exemplary substitutents can themselves be optionally substituted. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the term "halogen" refers to fluorine (F), chlorine (Cl), bromine (Br), or iodine (I).

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents. The exemplary substitutents can themselves be optionally substituted.

The term a "protein kinase related disorder" refers to any disease or deleterious condition in which a protein kinase plays a role. Examples include a serine-threonine kinase related disorder, a receptor tyrosine kinase related disorder, a non-receptor tyrosine kinase related disorder, an EGFR related disorder, an IGFR related disorder, a PDGFR related disorder and a flk related disorder.

According to one or more embodiments of the present invention, "cancer stem cell" ("CSC") or "cancer stem cells" ("CSCs") refer to a minute population of cancer cells that have self-renewal capability and are tumorigenic. They are also called "Cancer Initiating Cells", "Tumor Initiating Cells", "Cancer Stem-Like Cells", "Stem-Like Cancer Cells", "aggressive cancer cells", and "super malignant cancer cells", etc. The methods of isolating these cells include but not limited to enrichment by their ability of efflux Hoechst 33342, enrichment of surface markers such as CD133, CD44, and others, and enrichment by their tumorigenic property.

The term "CSCPK" or "CSCPKs" refer to protein kinase (s) that are essential for cancer stem cell survival or self-renewal.

Unless otherwise indicated, any heteroatom with unsatisfied valences is assumed to have hydrogen atoms sufficient to satisfy the valences.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}O$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007005643, WO 2007005644, WO 2007016361, and WO 2007016431.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The compounds, salts, esters, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates of the compounds of the invention are also contemplated herein. Solvates of the compounds of the present invention include, for example, hydrates.

DETAILED DESCRIPTION OF THE INVENTION

The invention provides unique novel inhibitors of cancer stem cells as well as cancer stem cell pathway kinase and other related kinases and targets, as well as pharmaceutical compositions and uses thereof in the treatment of a cancer or a related disorder in a mammal.

In one aspect, the invention generally relates to a compound of Formula I,

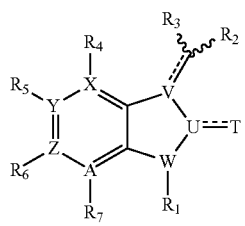

(I)

or an enantiomer, diastereomer, tautomer, or pharmaceutically acceptable salt or solvate thereof, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is monocyclic or bicyclic heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_aR_b$, $S(O)_2NR_aR_b$;

$R_4$, $R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

T is O, S or $R_a$;

U, V, and W are each independently a carbon, N, O, or S;

X, Y, Z, and A are each independently a carbon or N, with the proviso that the ring in which X, Y, Z, and A exist is aromatic;

with the provision that
one of $R_4$, $R_5$, $R_6$, and $R_7$ is

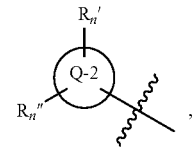

and
$R_4$, $R_5$, $R_6$, or $R_7$ is absent if X, Y, Z, or A, respectively, is a heteroatom;
wherein
Q-2 is a 5- or 6-membered aromatic or non-aromatic ring or ring system optionally having at least one ring carbon atom substituted with a heteroatom selected from N, O and S;
$R_{n'}$ and $R_{n''}$ are each independently hydrogen, halogen, cyano, nitro, trihalomethyl, $OCF_3$, alkyl or substituted alkyl, heterocycle or substituted heterocycle, aryl or substituted aryl, or $OR_a$;
$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;
$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and
$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, the compound has the formula of (I-a)

wherein T is O or S.

In certain embodiments, T is O, and the compound has the formula of (I-b)

In certain embodiments, V is carbon, and the compound has the formula of

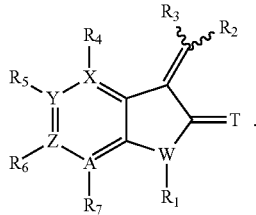
(I-c)

In certain embodiments, W is N, and the compound has the formula of

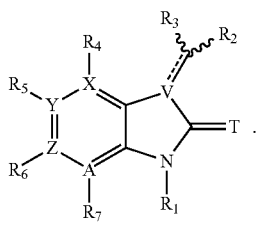
(I-d)

In certain embodiments, T is O and W is N, and the compound has the formula of

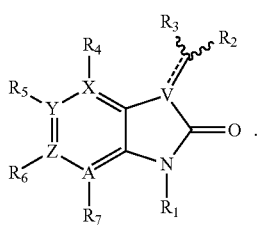
(I-e)

In certain embodiments, T is O and V is carbon, and the compound has the formula of

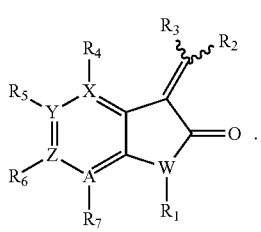
(I-f)

In certain embodiments, U is carbon, V is carbon, W is N, T is O, and the compound has the formula of

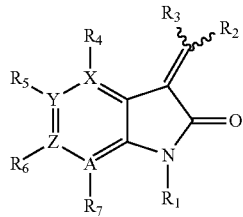
(I-g)

In certain embodiments, each of X, Y, Z, and A is carbon.
In certain embodiments, $R_2$ is

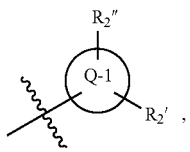

wherein
Q-1 is a 5- or 6-membered aromatic or non-aromatic ring or ring system optionally having at least one ring carbon atom substituted with a heteroatom selected from N, O and S;
$R_{2'}$ and $R_{2''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$.

In certain embodiments, one of X, Y, Z, and A is a heteroatom.
In certain embodiments, $R_2$ is

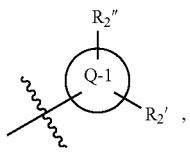

wherein
Q-1 is a 5- or 6-membered aromatic or non-aromatic ring or ring system optionally having at least one ring carbon atom substituted with a heteroatom selected from N, O and S;
$R_{2'}$ and $R_{2''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$.

Q-1 is a 5- or 6-membered aromatic or non-aromatic ring or ring system optionally having at least one ring carbon atom substituted with a heteroatom selected from N, O and S. 5- or 6-membered aromatic or non-aromatic rings or ring systems include, for examples, 5-membered or 6-membered aromatic or non-aromatic single rings or multi-fused or linked rings or ring systems. The ring or ring system, which may be for example saturated, partially unsaturated carbocyclic, can include in the cyclic backbone(s) 1, 2 or 3 heteroatoms independently of each other selected from N, O and S.

In certain embodiments, Q-1 is a 5-membered, aromatic ring with one heteroatom (e.g., N).

Q-2 is a 5- or 6-membered aromatic or non-aromatic ring or ring system optionally having at least one ring carbon atom substituted with a heteroatom selected from N, O and S. 5- or 6-membered aromatic or non-aromatic rings or ring systems include, for examples, 5-membered or 6-membered aromatic or non-aromatic single rings or multi-fused or linked rings or ring systems. The ring or ring system, which may be for example saturated, partially unsaturated carbocyclic, can include in the cyclic backbone(s) 1, 2 or 3 heteroatoms independently of each other selected from N, O and S.

In certain embodiments, Q-2 is a 5-membered, aromatic ring with two heteroatoms (e.g., N, S).

In another aspect, the invention generally relates to a compound of Formula II,

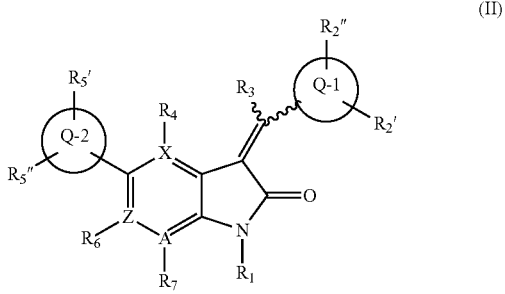

(II)

or an enantiomer, diastereomer, tautomer, or pharmaceutically acceptable salt or solvate thereof, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, $—OR_a$, $—C(O)R_a$, $—C(O)OR_a$, $—NR_aR_b$, $S(O)_2NR_aR_b$;

$R_4$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Z, and A are each independently a carbon or N, with the proviso that the ring in which X, Z, and A exist is aromatic;

Q-1 and Q-2 is independently is a 5- or 6-membered aromatic or non-aromatic ring or ring system optionally having at least one ring carbon atom substituted with a heteroatom selected from N, O and S;

$R_{2'}$ and $R_{2''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, $R_{5'}$ and $R_{5''}$ are each independently hydrogen, halogen, cyano, nitro, $CF_3$, $OCF_3$, alkyl or substituted alkyl, heterocycle or substituted heterocycle, aryl or substituted aryl, or $OR_a$;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, each of X, Z, and A is carbon.

In certain embodiments, one of X, Z, and A is a heteroatom.

In certain embodiments, the compound has the formula of

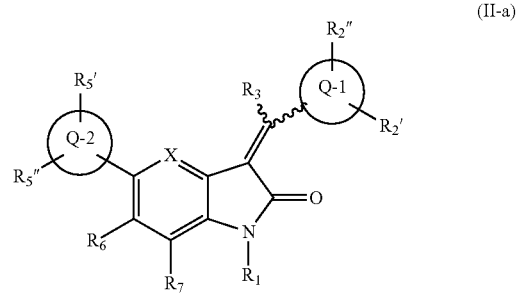

(II-a)

wherein X is C or N.

In certain embodiments, the compound of claim 2c, having the formula of

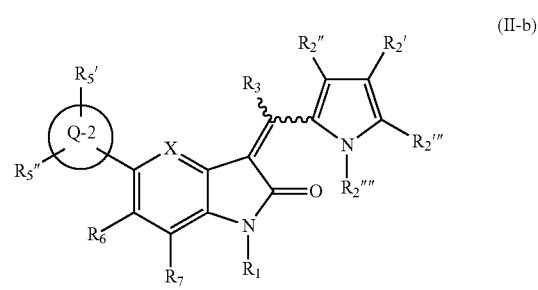

(II-b)

wherein

X is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2'''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, X is C. In certain embodiments, X is N.

In certain embodiments, $R_{2''}$ is H. In certain embodiments, each of $R_{2''}$ and $R_{2'''}$ is H.

In certain embodiments, the compound has the formula of

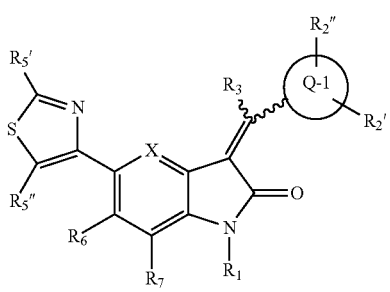
(II-c)

wherein X is C or N.

In certain embodiments, the compound has the formula of

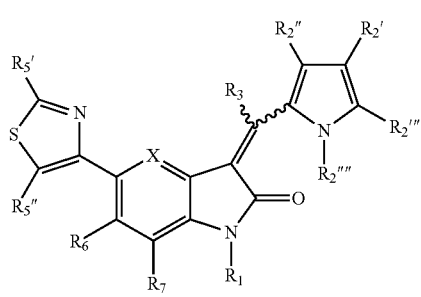
(II-d)

wherein

X is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2'''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, the compound has the formula of

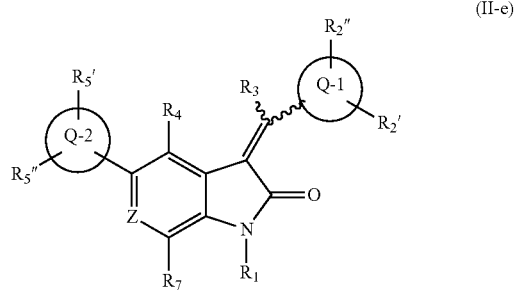
(II-e)

wherein Z is C or N.

In certain embodiments, the compound has the formula of

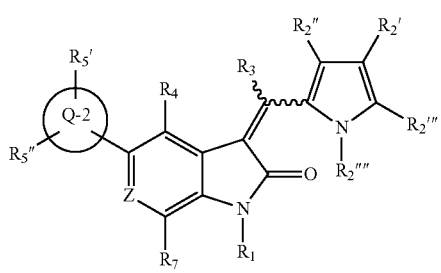
(II-f)

wherein

Z is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2'''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, Z is C. In certain embodiments, Z is N.

In certain embodiments, $R_{2''}$ is H. In certain embodiments, each of $R_2$ and $R_{2'''}$ is H.

In certain embodiments, the compound has the formula of

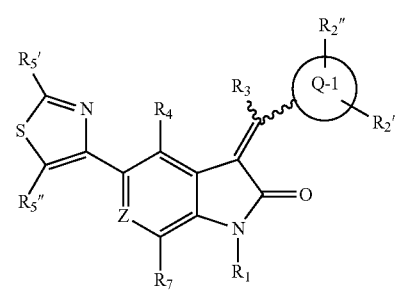
(II-g)

wherein Z is C or N.

In certain embodiments, the compound has the formula of

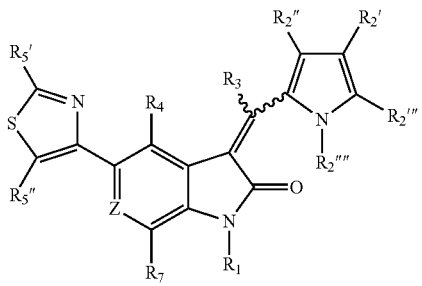

(II-h)

wherein

Z is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, the compound has the formula of

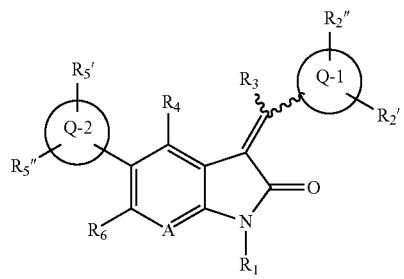

(II-i)

wherein A is C or N.

In certain embodiments, the compound has the formula of

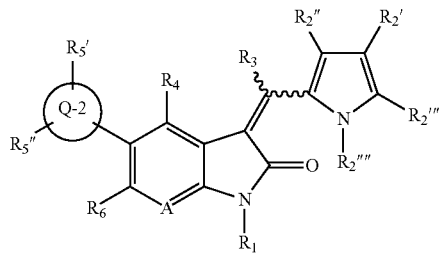

(II-j)

wherein

A is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, A is C. In certain embodiments, A is N.

In certain embodiments, $R_{2''''}$ is H. In certain embodiments, each of $R_2$ and $R_{2''''}$ is H.

In certain embodiments, the compound has the formula of

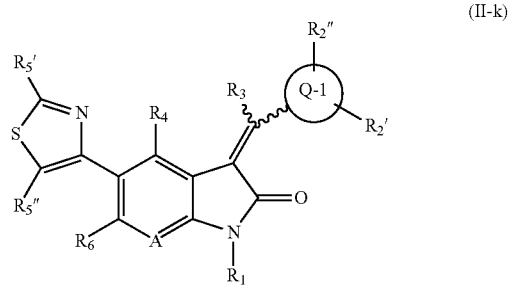

(II-k)

wherein A is C or N.

In certain embodiments, the compound has the formula of

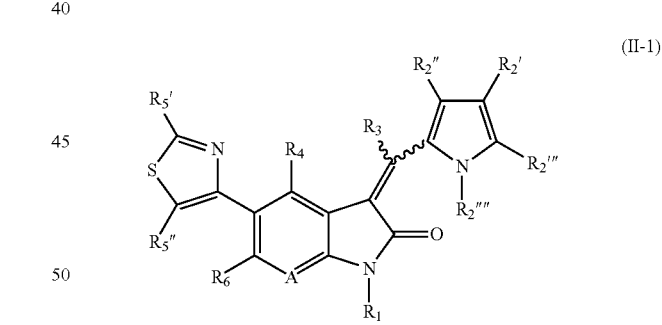

(II-1)

wherein

A is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In yet another aspect, the invention generally relates to a compound of Formula III,

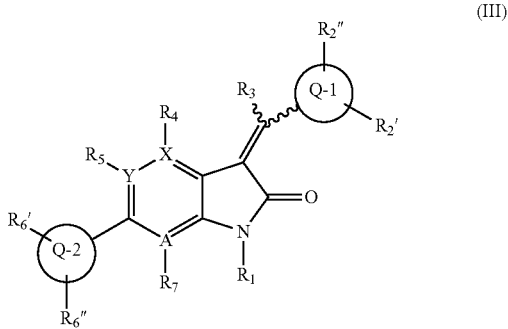

(III)

or an enantiomer, diastereomer, tautomer, or pharmaceutically acceptable salt or solvate thereof, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_aR_b$, $S(O)_2NR_aR_b$;

$R_4$, $R_5$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Y, and A are each independently a carbon or N, with the proviso that the ring in which X, Y, and A exist is aromatic;

Q-1 and Q-2 are each independently is a 5- or 6-membered aromatic or non-aromatic ring or ring system optionally having at least one ring carbon atom substituted with a heteroatom selected from N, O and S;

$R_2$ and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, $R_6'$ and $R_6''$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, each of X, Y, and A is carbon.

In certain embodiments, one of X, Y, and A is a heteroatom.

In certain embodiments, the compound has the formula of

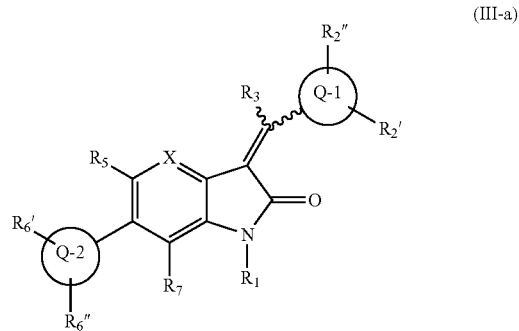

(III-a)

wherein X is C or N.

In certain embodiments, the compound has the formula of

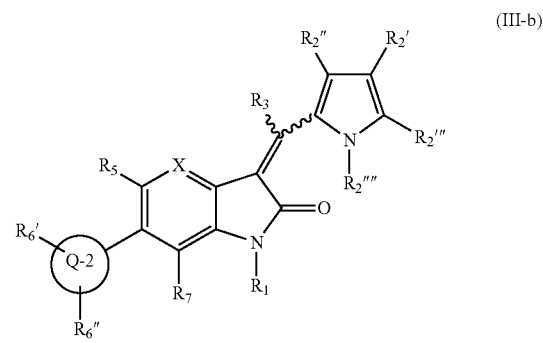

(III-b)

wherein

X is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, X is C. In certain embodiments, X is N.

In certain embodiments, $R_{2'''}$ is H. In certain embodiments, each of $R_2$ and $R_{2'''}$ is H.

In certain embodiments, the compound has the formula of

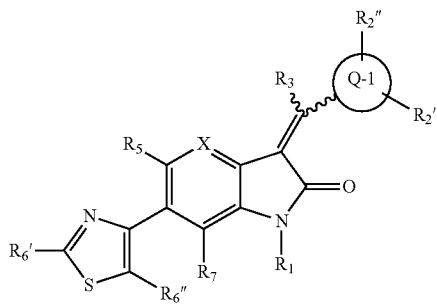

(III-c)

wherein X is C or N.

In certain embodiments, the compound has the formula of

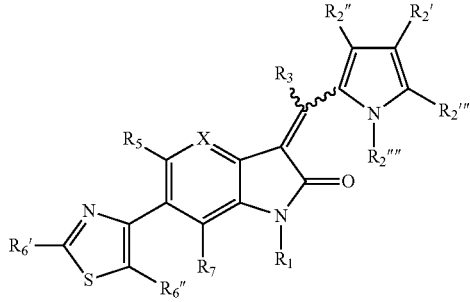

(III-d)

wherein

X is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, the compound has the formula of

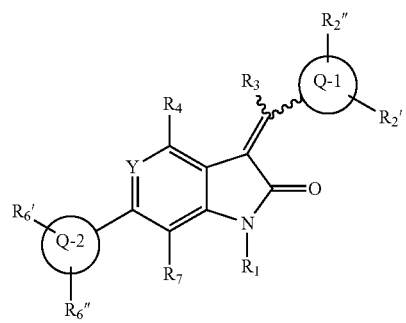

(III-e)

wherein Y is C or N.

In certain embodiments, the compound has the formula of

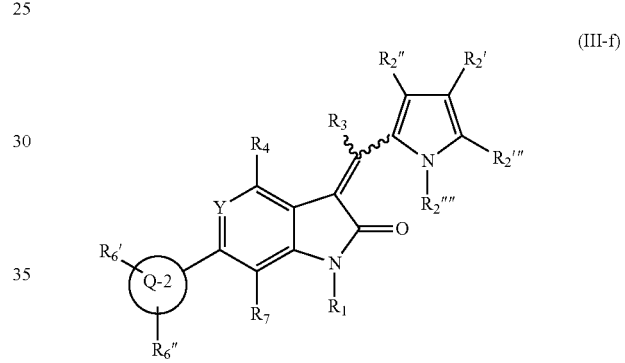

(III-f)

wherein

Y is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, Y is C. In certain embodiments, Y is N.

In certain embodiments, $R_{2'''}$ is H. In certain embodiments, each of $R_2$ and $R_{2'''}$ is H.

In certain embodiments, the compound has the formula of

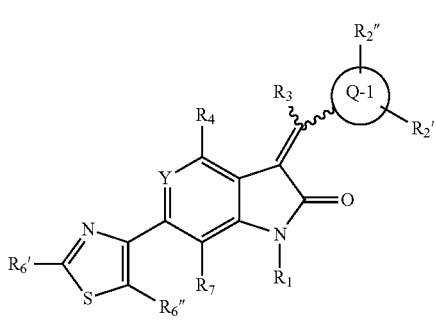

(III-g)

wherein Y is C or N.

In certain embodiments, the compound has the formula of

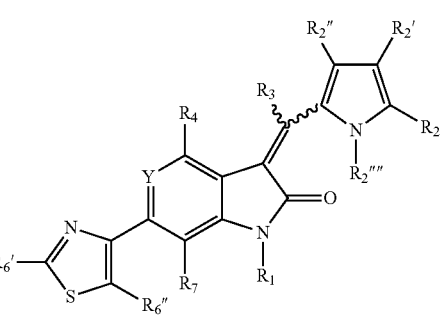

(III-h)

wherein

Y is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, the compound has the formula of

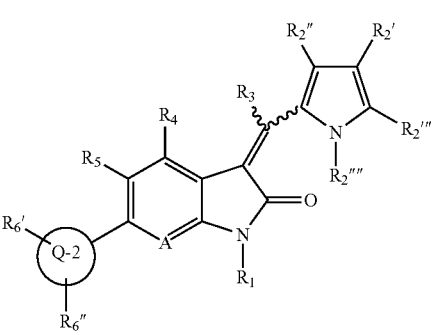

(III-i)

wherein A is C or N.

In certain embodiments, the compound has the formula of

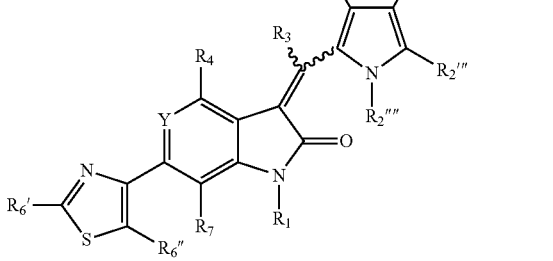

(III-j)

wherein

A is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, A is C. In certain embodiments, A is N.

In certain embodiments, $R_{2'''}$ is H. In certain embodiments, each of $R_{2''}$ and $R_{2'''}$ is H.

In certain embodiments, the compound has the formula of

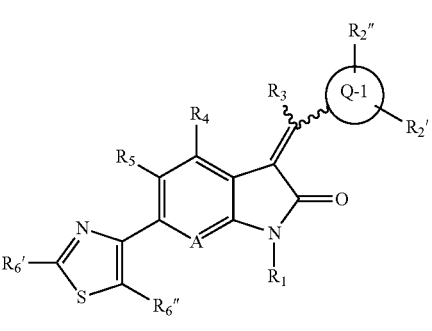

(III-k)

wherein A is C or N.

In certain embodiments, the compound has the formula of

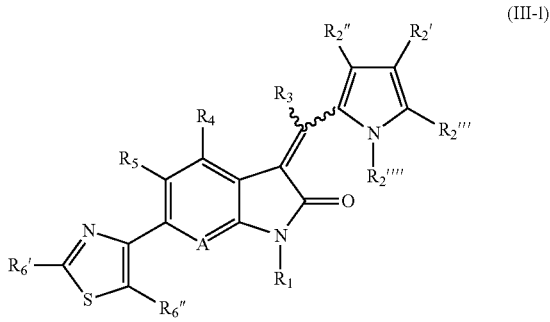

(III-1)

wherein

A is C or N,

R$_{2'}$, R$_{2''}$, and R$_{2'''}$ are each independently hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)2R$_e$, and R$_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$.

In yet another aspect, the invention generally relates to a compound of Formula IV,

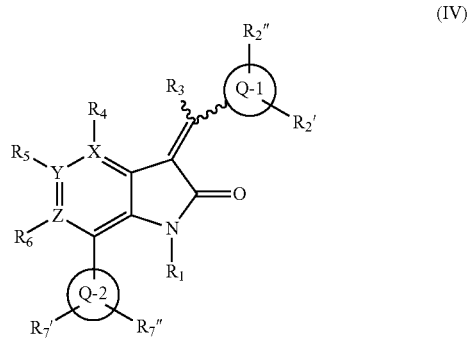

(IV)

or an enantiomer, diastereomer, tautomer, or pharmaceutically acceptable salt or solvate thereof, wherein R$_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$;

R$_3$ is hydrogen, alkyl or substituted alkyl, cycloalkyl or substituted cycloalkyl, heterocycle or substituted heterocycle, aryl or substituted aryl, halogen, —OR$_a$, —C(O)R$_a$, —C(O)OR$_a$, —NR$_a$R$_b$, S(O)$_2$NR$_a$R$_b$;

R$_4$, R$_5$, and R$_6$ are each independently hydrogen, halogen, cyano, nitro, trihalomethyl, OCF$_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$;

X, Y, and Z are each independently a carbon or N, with the proviso that the ring in which X, Y, and Z exist is aromatic;

Q-1 and Q-2 are each independently is a 5- or 6-membered aromatic or non-aromatic ring or ring system optionally having at least one ring carbon atom substituted with a heteroatom selected from N, O and S;

R$_{2'}$ and R$_{2''}$ are each independently hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)2Re, R$_{7'}$ and R$_{7''}$ are each independently hydrogen, halogen, cyano, nitro, trihalomethyl, OCF$_3$, alkyl or substituted alkyl, heterocycle or substituted heterocycle, aryl or substituted aryl, or OR$_a$;

wherein

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$, and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, each of X, Y, and Z is carbon. In certain embodiments, one of X, Y, and Z is a heteroatom.

In certain embodiments, the compound has the formula of

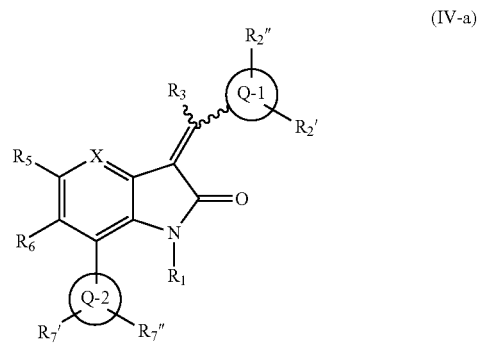

(IV-a)

wherein X is C or N.

In certain embodiments, the compound has the formula:

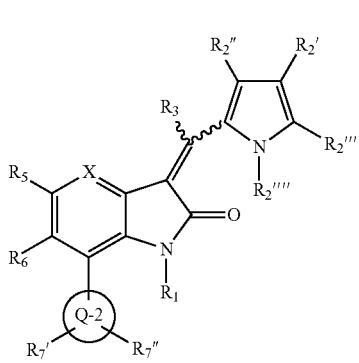
(IV-b)

wherein

X is C or N, $R_{2'}$, $R_{2'''}$, and $R_{2''''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, X is C. In certain embodiments, X is N.

In certain embodiments, $R_{2'''}$ is H. In certain embodiments, each of $R_2$ and $R_{2'''}$ is H.

In certain embodiments, the compound has the formula of

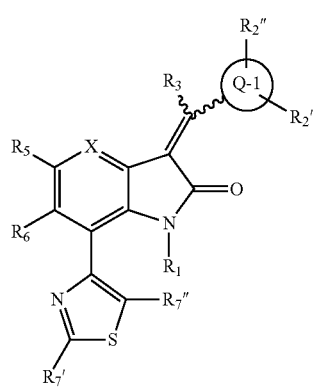
(IV-c)

wherein X is C or N.

In certain embodiments, the compound has the formula of

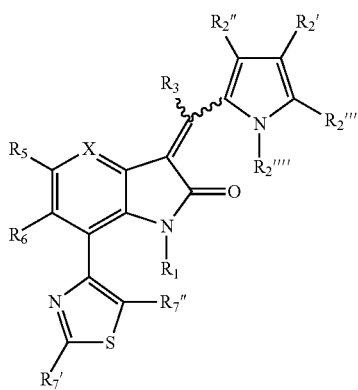
(IV-d)

wherein

X is C or N, $R_{2'}$, $R_{2'''}$, and $R_{2''''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, the compound has the formula of

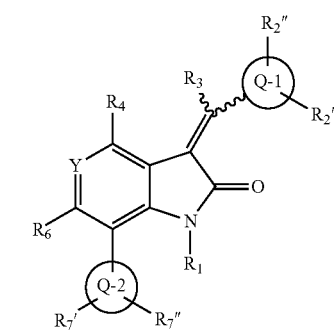
(IV-e)

wherein Y is C or N.

In certain embodiments, the compound has the formula of

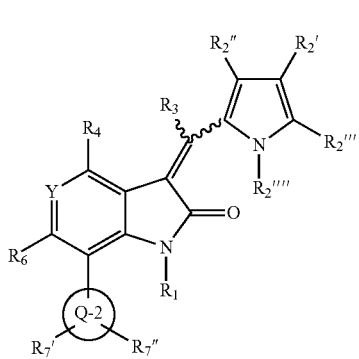

(IV-f)

wherein

Y is C or N, $R_{2'}$, $R_{2'''}$, and $R_{2''''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, Y is C. In certain embodiments, Y is N.

In certain embodiments, $R_{2''''}$ is H. In certain embodiments, each of $R_2$ and $R_{2''''}$ is H.

In certain embodiments, the compound has the formula of

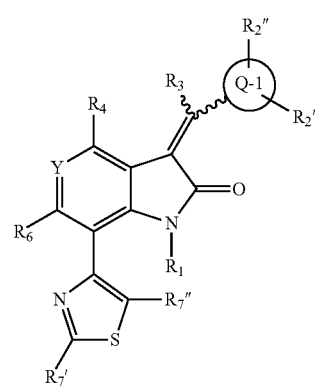

(IV-g)

wherein Y is C or N.

In certain embodiments, the compound has the formula of

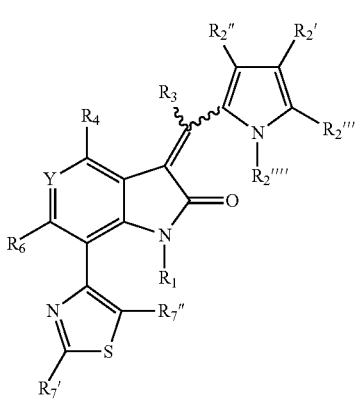

(IV-h)

wherein

Y is C or N, $R_{2'}$, $R_{2'''}$, and $R_{2''''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, the compound has the formula of

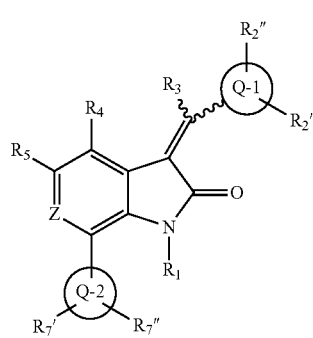

(IV-i)

wherein Z is C or N.

In certain embodiments, the compound has the formula:

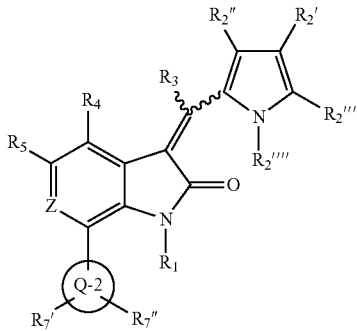

(IV-j)

wherein

Z is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, Z is C. In certain embodiments, Z is N.

In certain embodiments, $R_{2''''}$ is H. In certain embodiments, each of $R_2$ and $R_{2'''}$ is H.

In certain embodiments, the compound has the formula:

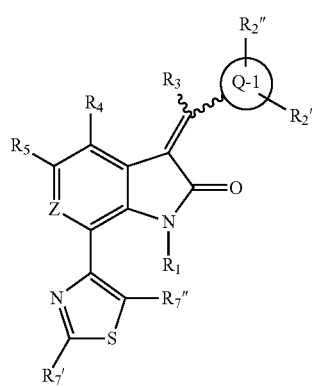

(IV-k)

wherein Z is C or N.

In certain embodiments, the compound has the formula:

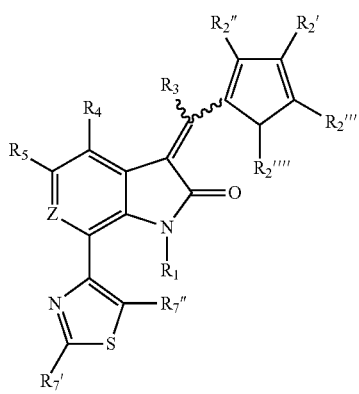

(IV-l)

wherein

Z is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In yet another aspect, the invention generally relates to a compound of Formula V

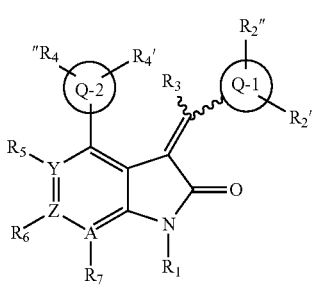

(V)

or an enantiomer, diastereomer, tautomer, or pharmaceutically acceptable salt or solvate thereof, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, —$OR_a$, —$C(O)R_a$, —$C(O)OR_a$, —$NR_aR_b$, $S(O)_2NR_aR_b$;

$R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

Y, Z and A are each independently a carbon or N, with the proviso that the ring in which Y, Z and A exist is aromatic;

Q-1 and Q-2 are each independently is a 5- or 6-membered aromatic or non-aromatic ring or ring system optionally having at least one ring carbon atom substituted with a heteroatom selected from N, O and S;

$R_{2'}$ and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, $R_{7'}$ and $R_{7'''}$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, each of Y, Z and A is carbon.

In certain embodiments, one of Y, Z and A is a heteroatom.

In certain embodiments, the compound has the formula of

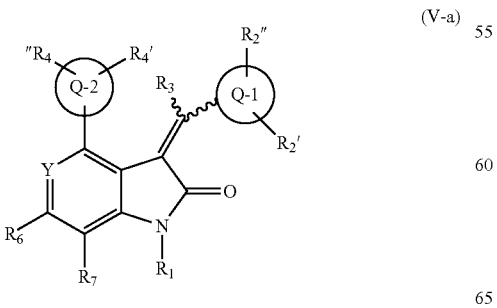

(V-a)

wherein Y is C or N.

In certain embodiments, the compound has the formula of

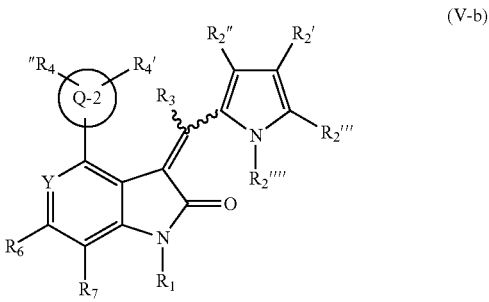

(V-b)

wherein

Y is C or N, $R_{2'}$, $R_{2''}$, and $R_{2'''}$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2Re$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

In certain embodiments, Y is C. In certain embodiments, Y is N.

In certain embodiments, $R_{2''''}$ is H. In certain embodiments, each of $R_2$ and $R_{2'''}$ is H.

In certain embodiments, the compound has the formula of

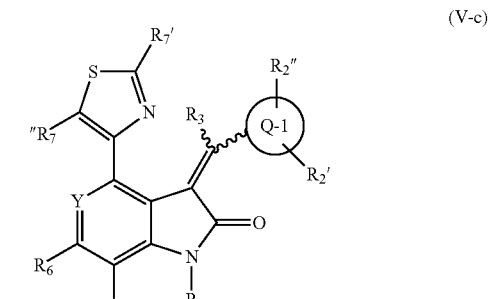

(V-c)

wherein Y is C or N.

In certain embodiments, the compound has the formula of

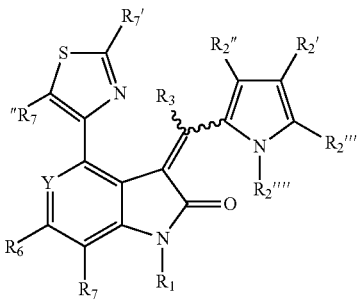

(V-d)

wherein
Y is C or N,
R$_{2'}$, R$_{2''}$, and R$_{2'''}$ are each independently hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)2Re, and
R$_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$.

In certain embodiments, the compound has the formula of

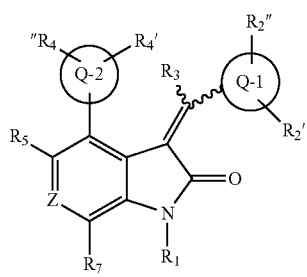

(V-e)

wherein Z is C or N.

In certain embodiments, the compound has the formula of

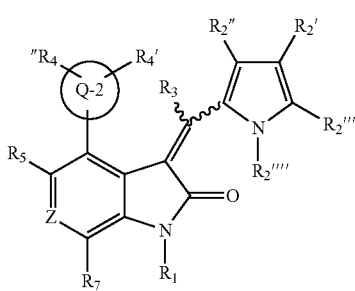

(V-f)

wherein
Z is C or N,
R$_{2'}$, R$_{2''}$, and R$_{2'''}$ are each independently hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)2Re, and
R$_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$.

In certain embodiments, Z is C. In certain embodiments, Z is N.

In certain embodiments, R$_{2'''}$ is H. In certain embodiments, each of R$_2$ and R$_{2'''}$ is H.

In certain embodiments, the compound has the formula of

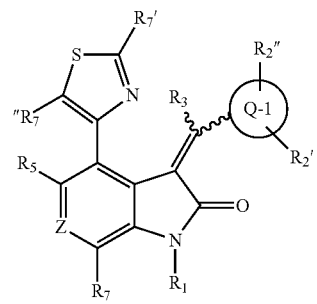

(V-g)

wherein Z is C or N.

In certain embodiments, the compound has the formula of

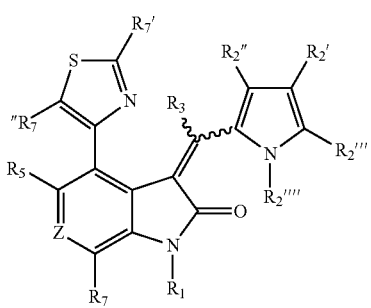

(V-h)

wherein
Z is C or N,
R$_{2'}$, R$_{2''}$, and R$_{2'''}$ are each independently hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)2Re, and R$_{2'''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$.

In certain embodiments, the compound has the formula of

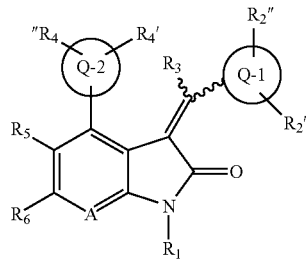

(V-i)

wherein Z is C or N.

In certain embodiments, the compound has the formula of

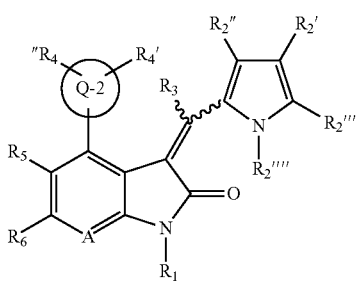

(V-j)

wherein

Z is C or N,

R$_{2'}$, R$_{2''}$, and R$_{2'''}$ are each independently hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)2Re, and R$_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$.

In certain embodiments, Z is C. In certain embodiments, Z is N.

In certain embodiments, R$_{2'''}$ is H. In certain embodiments, each of R$_2$ and R$_{2'''}$ is H.

In certain embodiments, the compound has the formula of

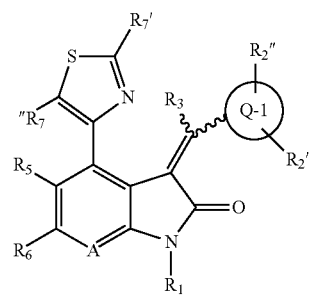

(V-k)

wherein A is C or N.

In certain embodiments, the compound has the formula of

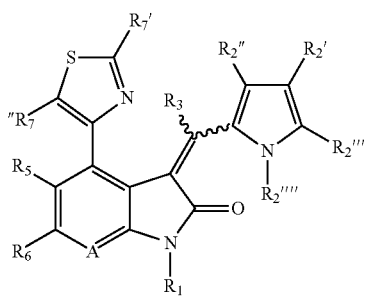

(V-l)

wherein

A is C or N,

R$_{2'}$, R$_{2''}$, and R$_{2'''}$ are each independently hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)2Re, and R$_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$.

In yet another aspect, the invention generally relates to a pharmaceutical composition comprising a compound disclosed herein, or a pharmaceutically acceptable salt, ester or pro-drug thereof, and a pharmaceutically acceptable excipient, carrier, or diluent.

In yet another aspect, the invention generally relates to a method of treating or preventing cancer, or a related disorder or condition thereof in a mammal, including a human, comprising administering to a subject in need thereof a therapeutically effective amount of a pharmaceutical composition comprising a compound disclosed herein, or a pharmaceutically acceptable salt, ester or pro-drug thereof, effective in the treatment or prevention of cancer, or a related disorder or condition thereof in a mammal, including a human, and a pharmaceutically acceptable excipient, carrier, or diluent.

The present invention also provides a method of treating, preventing or ameliorating a protein kinase related disorder in a mammal, comprising administering to the mammal in need thereof a therapeutically effective amount of a pharmaceutical composition comprising a compound of the present invention as described herein. The mammal may be in need of the treatment or the treatment may be administered prophylacticly for prevention or for amelioration of the protein kinase related disorder.

In certain embodiments, the protein kinase related disorder is a cancer such as lung cancer, bladder cancer, head and neck cancer, melanoma, ovarian cancer, prostate cancer, breast cancer, small-cell lung cancer, glioma, colorectal cancer, non-small cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma.

In certain embodiments, the protein kinase is CSCPK. The compounds of the present invention are particularly useful for the treatment, prevention or amelioration of cancer, such as lung cancer, bladder cancer, head and neck cancer, melanoma, ovarian cancer, prostate cancer, breast cancer, small-cell lung cancer, glioma, colorectal cancer, non-small-cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma, by inhibiting CSCPKs.

In yet other embodiments, the protein kinase includes serine-threonine kinases, receptor tyrosine kinases and non-receptor tyrosine kinases.

In yet other embodiments, the protein kinase related disorder includes diabetes, an autoimmune disorder, a hyperproliferation disorder, angiogenesis, an inflammatory disorder, an immunological disorder, a cardiovascular disorder, restenosis, fibrosis, psoriasis, von Heppel-Lindau disease, osteoarthritis, neurodegeneration, infection, and rheumatoid arthritis.

The present invention provides, in part, a method of inhibiting/reducing/diminishing cancer stem cell survival and/or proliferation, self-renewal in a mammal by inhibiting or decreasing unwanted activity of CSCPKs.

The present invention also provides a method of inhibiting cancer stem cell niche, or stromal cell signaling by targeting CSCPKs.

The present invention further provides, in part, a method of treating cancer, inhibiting/reducing/diminishing cancer stem cell survival and/or proliferation.

The present invention also provides a method of modulating the catalytic activity of a protein kinase. The method comprises contacting said protein kinase with a compound of the present invention, or a pharmaceutically-acceptable salt, ester or pro-drug thereof. In certain embodiments, the protein kinase includes a serine-threonine kinase, a receptor tyrosine kinase and a non-receptor tyrosine kinase.

The present invention also provides, in part, a pharmaceutical composition comprising a compound of the present invention as described hereinabove, or an enantiomer, diastereomer, tautomer, or pharmaceutically acceptable salt, ester or pro-drug thereof, and a pharmaceutically-acceptable excipient, carrier, or diluent.

Presently disclosed pharmaceutical compositions can be used in an animal or human. A presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation. The compounds presently disclosed may also be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

The formulations may conveniently be presented in unit dosage form and may be prepared by any methods well known in the art of pharmacy. The amount of active ingredient that can be combined with a carrier material to produce a single dosage form will vary depending upon the mammal being treated and the particular mode of administration. The amount of active ingredient, which can be combined with a carrier material to produce a single dosage form will generally be that amount of the compound which produces a therapeutic effect. Generally, out of 100%, this amount will range, for example, from about 0.1% to about 25% (e.g., 1%, 2%, 5%, 10%, 15%, 20%) of active ingredient.

Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the alcohol or inhibitor according to the invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to the alcohols or inhibitors according to the invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more alcohols or inhibitors according to the invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of an alcohol or other inhibitor according to the invention include powders, sprays, ointments, pastes, creams, lotions, gels, solutions, patches and inhalants. The active compound may be mixed under sterile conditions with a pharmaceutically-acceptable excipient, carrier, or diluent, including any preservatives, buffers, or propellants which may be required.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

The ointments, pastes, creams and gels may contain, in addition to an alcohol or other inhibitor according to the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more alcohols or inhibitors according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the alcohol or inhibitor according to the invention, it is desirable to slow the absorption of the alcohol or inhibitor from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered composition is accomplished by dissolving or suspending the alcohol or inhibitor in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone, or simultaneously, subsequently or sequentially with one or more active agents, other pharmaceutical agents, or with other anti-cancer or cytotoxic agent as described hereinabove, as well as in combination with a pharmaceutically-acceptable excipient, carrier, or diluent as described above.

The amount of pharmacological agent in the oral unit dosage form, with as a single or multiple dosage, is an amount that is effective for treating a neurological disorder. As one of skill in the art will recognize, the precise dose to be employed will depend on a variety of factors, examples of which include the condition itself, the seriousness of the condition being treated, the particular composition used, as well as various physical factors related to the individual being treated. In vitro or in vivo assays can optionally be employed to help identify optimal dosage ranges.

A proposed dose of a presently disclosed compound for oral, parenteral or buccal administration to the average adult human for the treatment or prevention of a disease state herein relevant is about 0.1 mg to about 2000 mg. In certain embodiments, the proposed dose is from about 0.1 mg to about 200 mg (e.g., 1 mg, 5 mg, 10 mg, 20 mg, 50 mg, 75 mg, 100 mg, 150 mg) of the active ingredient per unit dose. Irrespective of the amount of the proposed dose, administration of the compound can occur, for example, 1, 2, 3, or 4 times per day, or 1, 2, 3, 4 or 5 times a week.

Aerosol formulations for the treatment or prevention of the conditions referred to herein the average adult human are preferably arranged so that each metered dose or "puff" of aerosol contains about 20 µg to about 10,000 µg, preferably, about 20 µg to about 1000 µg (e.g., 25 µg, 50 µg, 100 µg, 200 µg, 500 µg, 750 µg) of a presently disclosed compound. The overall daily dose with an aerosol will be within the range from about 100 µg to about 100 mg (e.g., 200 µg, 500 µg, 1 mg, 2 mg, 5 mg, 10 mg, 25 mg, 50 mg, 75 mg). In certain embodiments, the overall daily dose with an aerosol generally will be within the range from about 100 µg to about 10 mg (e.g., 200 µg, 500 µg, 1 mg, 2 mg, 5 mg, 7.5 mg). Administration may be several times daily, for example 1, 2, 3, 4, 5 or 8 times, giving for example, 1, 2 or 3 doses each time.

The compounds of the present invention can be prepared using the methods described below, together with synthetic methods known to one skilled in the art of organic synthesis, medicinal chemistry and related fields, or variations thereon. The reactions are performed in solvents where appropriate to the reagents and materials employed and are suitable for transformations being effected. The starting materials for the examples contained herein are either commercially available or are readily prepared by standard methods from known materials. For example, the following reactions are illustrations but not limitations of the preparation of some of the starting materials and examples used herein.

EXAMPLES

Chemical Synthesis

Example 1

Preparation of Compound 332

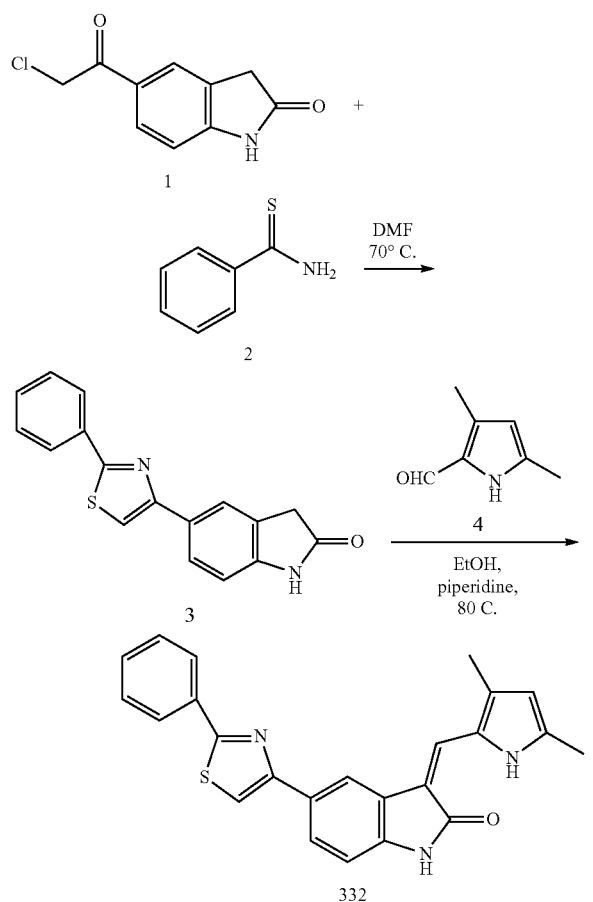

Step 1

A suspension of 5-chloroacetyloxindole 1 (838 mg, 4 mmol) and thiobenzamide 2 (550 mg, 4 mmol) in DMF (8 mL) was heated at 70° C. for 16 h and then cooled down to room temperature. At 0° C., while stirring, Na2CO3 aq (1N, 8 mL) was added drop wise to the reaction mixture. The mixture was stirred at room temperature for 20 min, filtrated, and washed with H2O 2O (5 mL×2). The cake was put into a flask and EtOH (5 mL) was added. The mixture was stirred at room temperature for 30 min, filtrated, and washed with EtOH (2 mL×2). The collected solid was dried down under vacuum to yield a light brown solid 3 (1.0 g, 85%).

Step 2

To a suspension of 3 (58 mg, 0.2 mmol) in EtOH (3 mL) was added 4 (28 mg, 0.2 mmol) and piperidine (a drop). The resulted mixture was heated at 80 C for 16 h before cooled down. The reaction mixture was concentrated. The residue was purified by pre-HPLC to get product 332 (20 mg). m/z 398 [M+1]

Example 2

Preparation of Compound 333

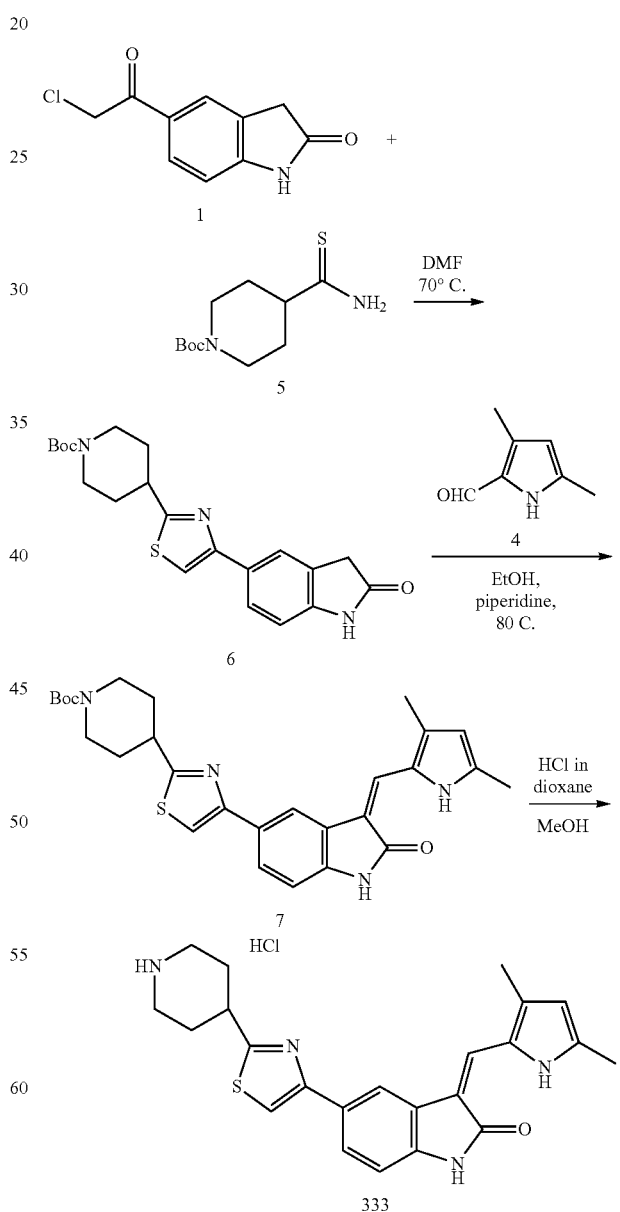

Step 1

A suspension of 5-chloroacetyloxindole 1 (419 mg, 2 mmol) and thiamide 5 (489 mg, 2 mmol) in DMF (10 mL) was heated at 80 C for 16 h and then cooled down to room temperature. The mixture was concentrated, and the residue was partitioned in EtOAc and 1N NaHCO3 aq. The organic layer was washed with H2O, and brine, dried over Na2SO4, and concentrated in vacuo. The residue was purified by pre-HPLC to get product 6.

Step 2

To a suspension of 6 (80 mg, 0.2 mmol) in EtOH (3 mL) was added 4 (28 mg, 0.2 mmol) and piperidine (0.1 mL). The resulted mixture was heated at 80 C for 2 h before cooled down. The reaction mixture was concentrated. The residue was partitioned in EtOAc and H2O. The organic layer was washed with H2O, and brine, dried over Na2SO4, and concentrated in vacuo. The residue was purified by pre-HPLC to get product 7.

Step 3

To a solution of 7 (65 mg, 0.13 mmol) in MeOH (5 mL) was added HCl (4N in dioxane, 1 mL). The resulted mixture was stirred at room temperature for over night. The reaction mixture was concentrated. The residue was purified by pre-HPLC to get product 333 (37 mg). m/z 405 [M+1]

Example 3

Preparation of Compound 334

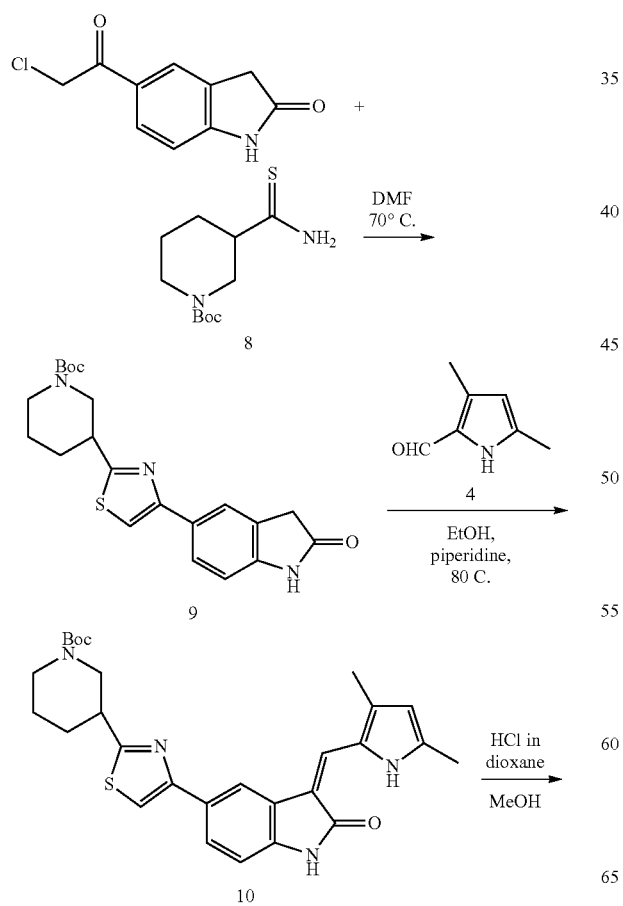

-continued

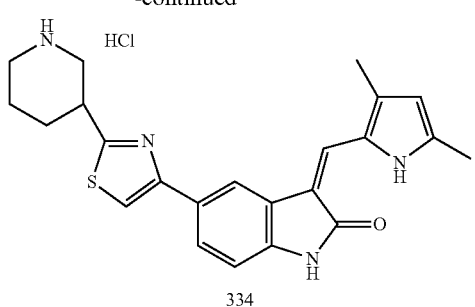

334

Step 1

A suspension of 5-chloroacetyloxindole 1 (419 mg, 2 mmol) and thiamide 8 (489 mg, 2 mmol) in DMF (10 mL) was heated at 80 C for 16 h and then cooled down to room temperature. The mixture was concentrated, and the residue was partitioned in EtOAc and 1N NaHCO3 aq. The organic layer was washed with H2O, and brine, dried over Na2SO4, and concentrated in vacuo. The residue was purified by pre-HPLC to get product 9.

Step 2

To a suspension of 9 (80 mg, 0.2 mmol) in EtOH (3 mL) was added 4 (28 mg, 0.2 mmol) and piperidine (0.1 mL). The resulted mixture was heated at 80 C for 2 h before cooled down. The reaction mixture was concentrated. The residue was partitioned in EtOAc and H2O. The organic layer was washed with H2O, and brine, dried over Na2SO4, and concentrated in vacuo. The residue was purified by pre-HPLC to get product 10.

Step 3

To a solution of 10 (70 mg, 0.14 mmol) in MeOH (5 mL) was added HCl (4N in dioxane, 1 mL). The resulted mixture was stirred at room temperature for over night. The reaction mixture was concentrated. The residue was purified by pre-HPLC to get product 334 (21 mg). m/z 405 [M+1]

Example 4

Preparation of Compound 335

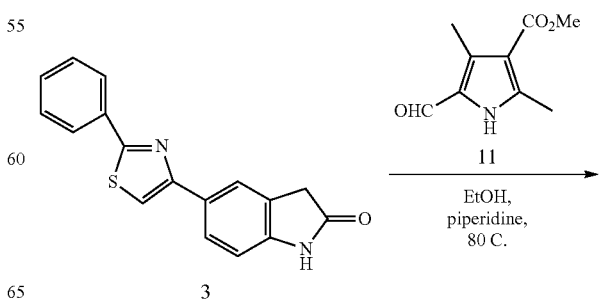

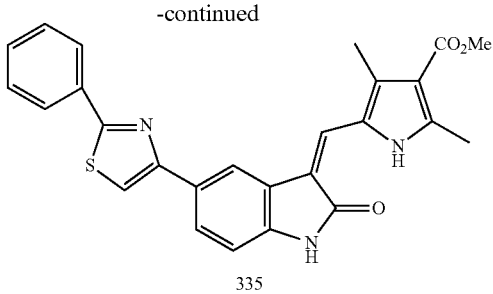

335

Step 1

To a suspension of 3 (58 mg, 0.2 mmol) in EtOH (3 mL) was added 11 (40 mg, 0.22 mmol) and piperidine (one drop). The resulted mixture was heated at 80 C for 16 h before cooled down. The reaction mixture was concentrated. The residue was purified by pre-HPLC to get product 335 (81 mg). m/z 456 [M+1]

Example 5

Preparation of Compound 336

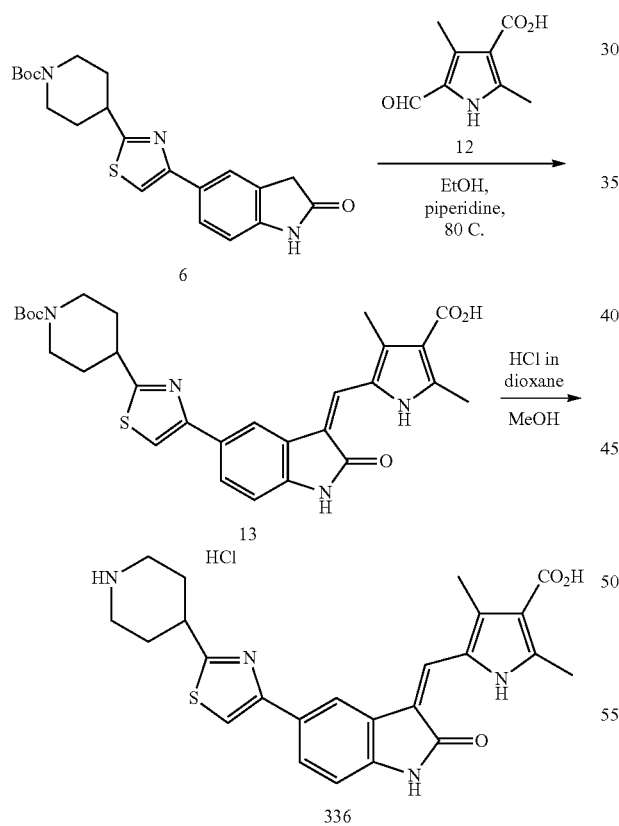

Step 1

To a suspension of 6 (80 mg, 0.2 mmol) in EtOH (3 mL) was added 12 (34 mg, 0.2 mmol) and piperidine (0.1 mL). The resulted mixture was heated at 80 C for 2 h before cooled down. The reaction mixture was concentrated. The residue was partitioned in EtOAc and H2O, adjusted pH to 5. The organic layer was dried over Na2SO4, and concentrated in vacuo. The residue was purified by pre-HPLC to get product 13.

Step 2

To a solution of 13 (35 mg, 0.064 mmol) in MeOH (5 mL) was added HCl (4N in dioxane, 1 mL). The resulted mixture was stirred at room temperature for over night. The reaction mixture was concentrated. The residue was purified by pre-HPLC to get product 336 (19 mg). m/z 449 [M+1]

Example 6

Preparation of Compound 337

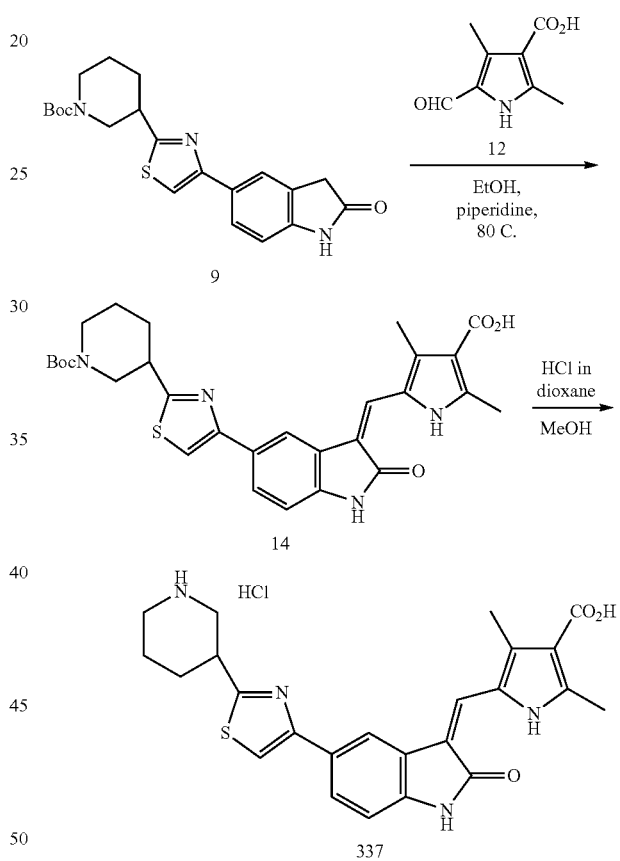

Step 1

To a suspension of 9 (80 mg, 0.2 mmol) in EtOH (3 mL) was added 12 (34 mg, 0.2 mmol) and piperidine (0.1 mL). The resulted mixture was heated at 80 C for 2 h before cooled down. The reaction mixture was concentrated. The residue was partitioned in EtOAc and H2O, adjusted pH to ~5. The organic layer was dried over Na2SO4, and concentrated in vacuo. The residue was purified by pre-HPLC to get product 14.

Step 2

To a solution of 14 (31 mg, 0.06 mmol) in MeOH (5 mL) was added HCl (4N in dioxane, 1 mL). The resulted mixture was stirred at room temperature for over night. The reaction mixture was concentrated. The residue was purified by pre-HPLC to get product 337 (15 mg). m/z 449 [M+1]

Example 7

Preparation of Compound 338

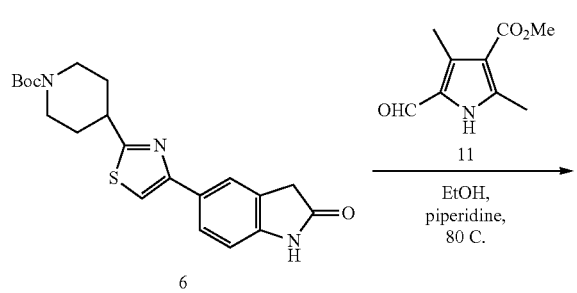

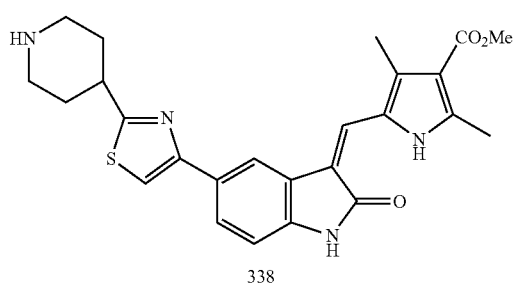

Step 1

To a suspension of 6 (80 mg, 0.2 mmol) in EtOH (3 mL) was added 11 (40 mg, 0.22 mmol) and piperidine (one drop). The resulted mixture was heated at 80 C for 16 h before cooled down. The reaction mixture was concentrated. The residue was purified by pre-HPLC to get product 15.

Step 2

To a solution of 15 (56 mg, 0.1 mmol) in MeOH (5 mL) was added HCl (4N in dioxane, 1 mL). The resulted mixture was stirred at rt for overnight. The reaction mixture was concentrated. The residue was purified by pre-HPLC to get product 338 (45 mg). m/z 463 [M+1]

Example 8

Preparation of Compound 339

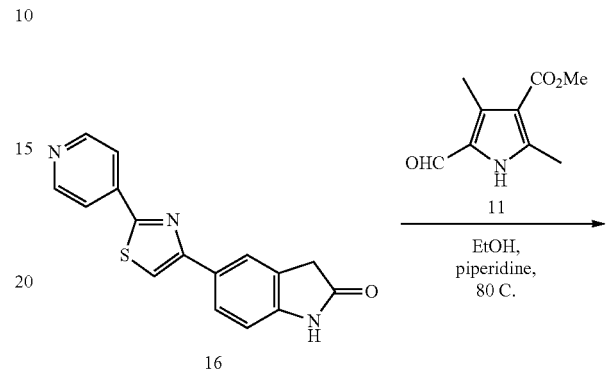

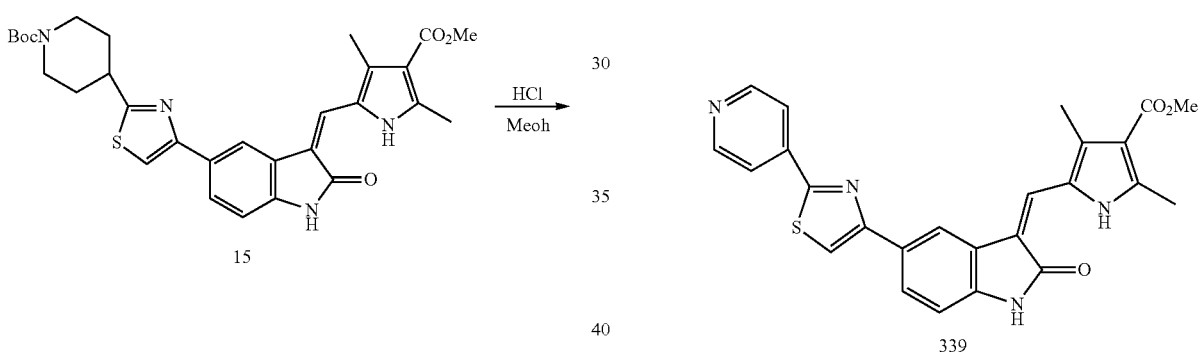

Step 1

To a suspension of 16 (80 mg, 0.2 mmol) in EtOH (3 mL) was added 11 (40 mg, 0.22 mmol) and piperidine (one drop). The resulted mixture was heated at 80 C for 16 h before cooled down. The reaction mixture was concentrated. The residue was purified by pre-HPLC to get product 339 (55 mg). m/z 457 [M+1]

Example 9

Preparation of Compound 340

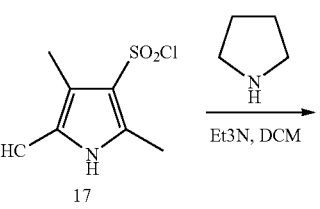

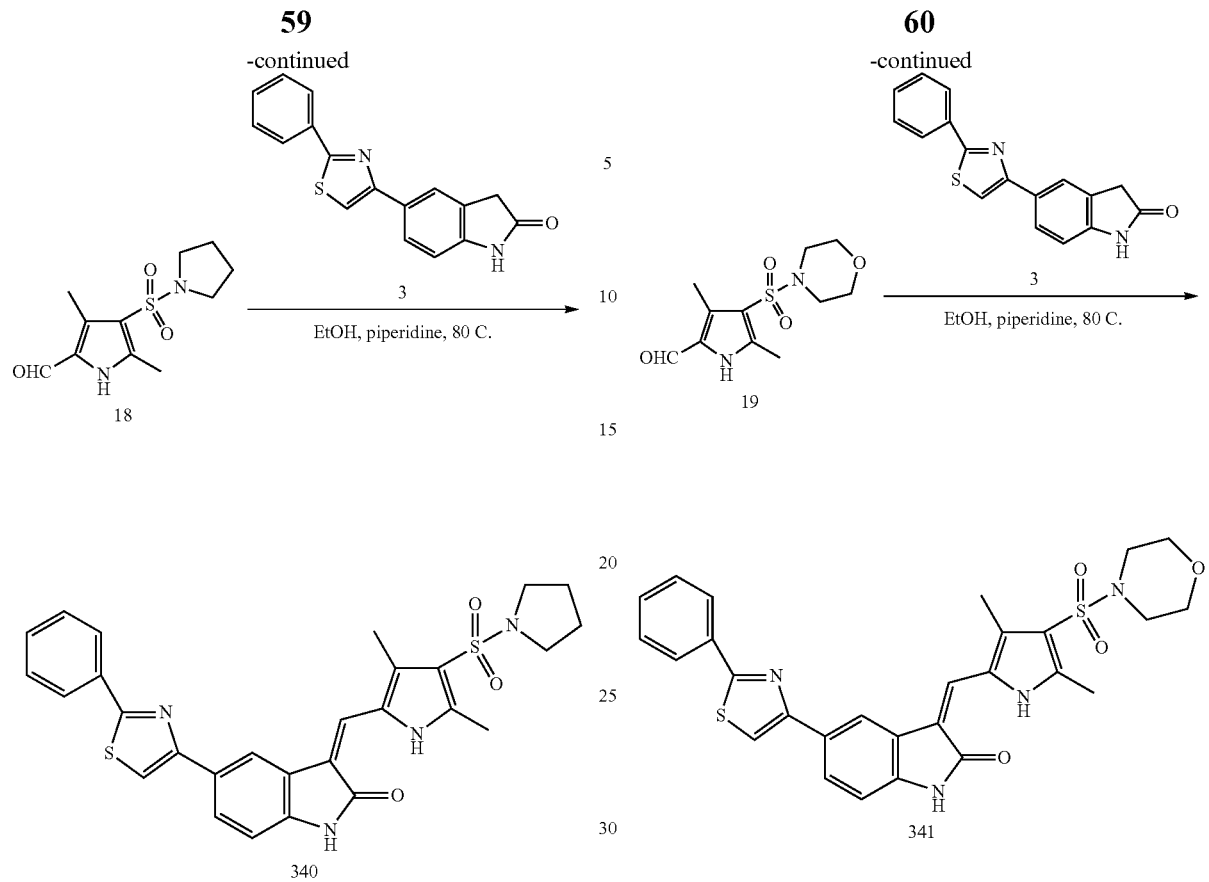

Step 1

To a solution of 17 (66 mg, 0.3 mmol) in dichloromethane (2 mL) at 0 C was added pyrrolidine (50 ul) and then Et3N (200 ul). The reaction mixture was stirred for 2 h before quenching with aq NH4Cl then regular aqueous work-up. The residue was purified by pre-HPLC to get product to get product 18.

Step 2

To a suspension of 3 (58 mg, 0.2 mmol) in EtOH (3 mL) was added 18 (54 mg, 0.21 mmol) and piperidine (a drop). The resulted mixture was heated at 80 C for 16 h before cooled down. The reaction mixture was concentrated. The residue was purified by pre-HPLC to get product 340 (85 mg). m/z 531 [M+1]

Step 1

To a solution of 17 (66 mg, 0.3 mmol) in dichloromethane (2 mL) at 0 C was added morphline (50 ul) and then Et3N (200 ul). The reaction mixture was stirred for 2 h before quenching with aq NH4Cl then regular aqueous work-up. The residue was purified by pre-HPLC to get product to get product 19.

Step 2

To a suspension of 3 (58 mg, 0.2 mmol) in EtOH (3 mL) was added 19 (59 mg, 0.21 mmol) and piperidine (a drop). The resulted mixture was heated at 80 C for 16 h before cooled down. The reaction mixture was concentrated. The residue was purified by pre-HPLC to get product 341 (98 mg). m/z 547 [M+1]

Example 10

Preparation of Compound 341

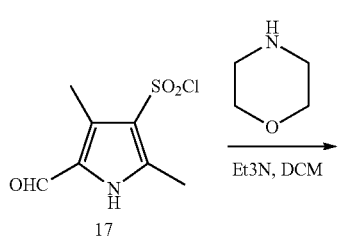

Example 11

Preparation of Compound 342

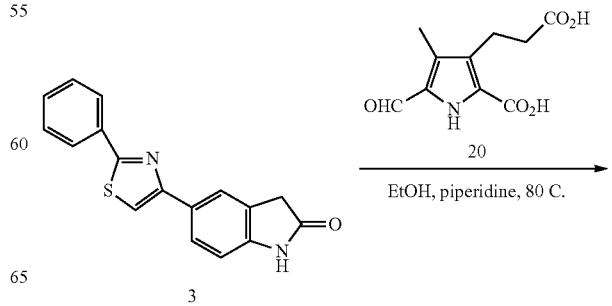

61

-continued

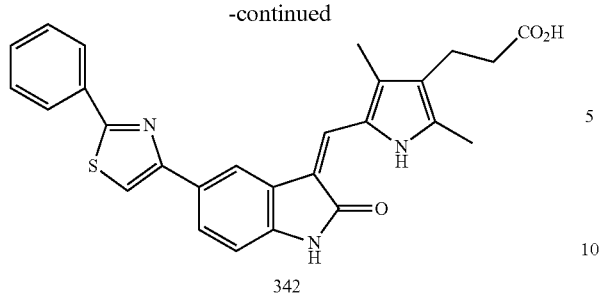

342

Step 1

To a suspension of 3 (58 mg, 0.2 mmol) in EtOH (3 mL) was added 20 (42 mg, 0.22 mmol) and piperidine (one drop). The resulted mixture was heated at 80 C for 16 h before cooled down. The reaction mixture was concentrated and neutralized to pH=4-5. The residue was purified by pre-HPLC to get product 342 (20 mg). m/z 470 [M+1]

Example 12

Preparation of Compound 343

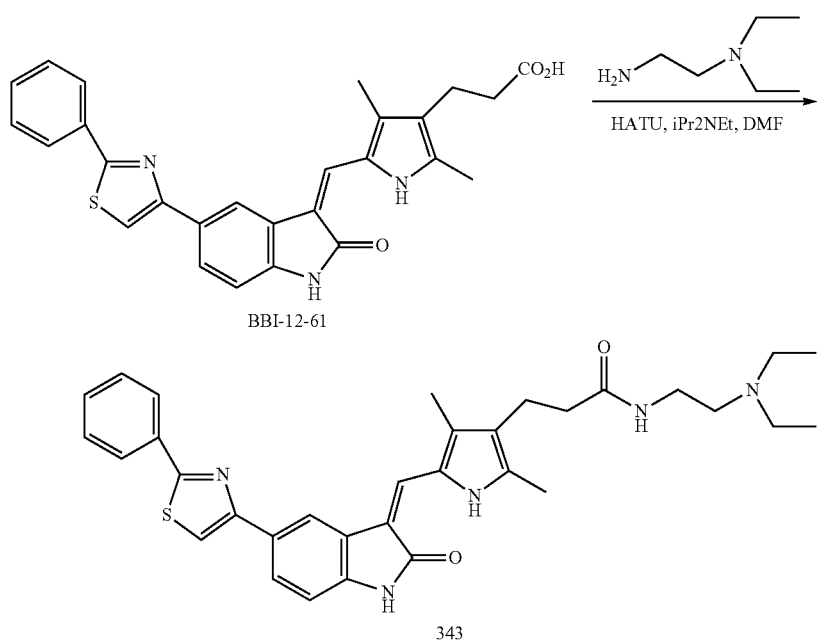

Step 1

To a solution of BBI-12-61 (41 mg, 0.088 mmol) in DMF (1.5 mL) was added HATU (67 mg), diisopropylethylamine (500 uL), and diethylethylenediamine (25 mg). The mixture was stirred at room temperature for 16 hours then concentrated in vacuo. The residue was added $CH_2Cl_2$ and washed with $H_2O$. The organic layer was dried over $Na_2SO_4$ and concentrated in vacuo. The residue was purified by pre-HPLC to get product 343 (40 mg). m/z 568 [M+1]

62

Example 13

Preparation of Compound 344

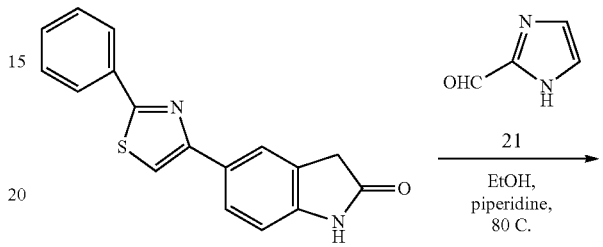

-continued

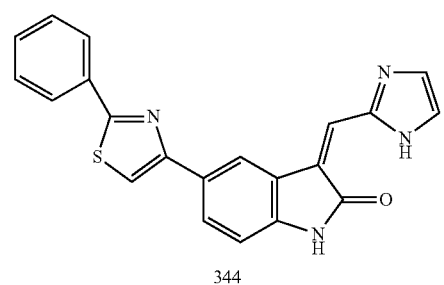

344

Step 1

To a suspension of 3 (58 mg, 0.2 mmol) in EtOH (3 mL) was added 21 (21 mg, 0.22 mmol) and piperidine (one drop). The resulted mixture was heated at 80 C for 16 h before cooled down. The reaction mixture was concentrated. The residue was purified by pre-HPLC to get product 344 (42 mg). m/z 371 [M+1]

Example 14

Preparation of Compound 345

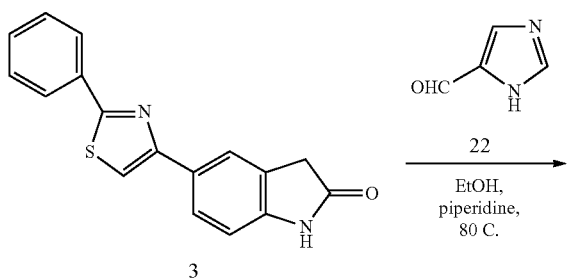

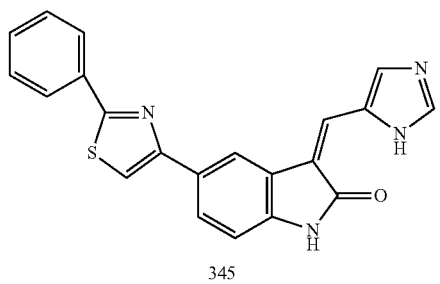

345

Step 1

To a suspension of 3 (58 mg, 0.2 mmol) in EtOH (3 mL) was added 22 (21 mg, 0.22 mmol) and piperidine (one drop). The resulted mixture was heated at 80 C for 16 h before cooled down. The reaction mixture was concentrated. The residue was purified by pre-HPLC to get product 345 (45 mg). m/z 371 [M+1]

Example 15

Preparation of Compound 346

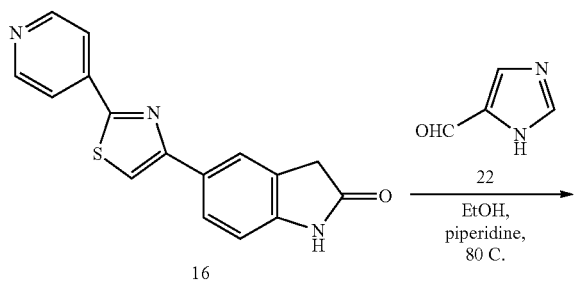

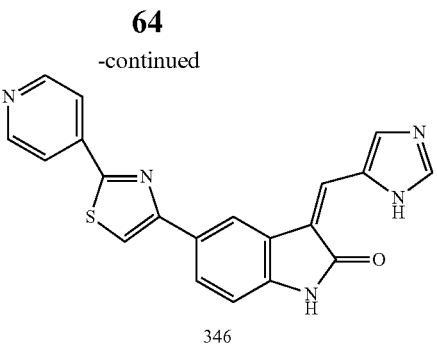

346

Step 1

To a suspension of 16 (59 mg, 0.2 mmol) in EtOH (3 mL) was added 22 (21 mg, 0.22 mmol) and piperidine (one drop). The resulted mixture was heated at 80 C for 16 h before cooled down. The reaction mixture was concentrated. The residue was purified by pre-HPLC to get product 346 (38 mg). m/z 372 [M+1]

Example 16

Preparation of Compound 347

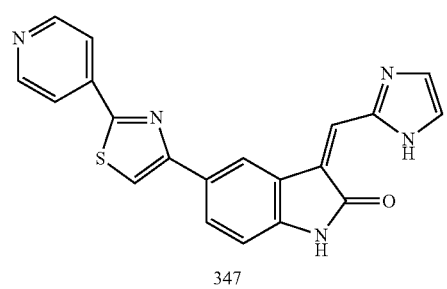

347

Step 1

To a suspension of 16 (59 mg, 0.2 mmol) in EtOH (3 mL) was added 22 (21 mg, 0.22 mmol) and piperidine (one drop). The resulted mixture was heated at 80 C for 16 h before cooled down. The reaction mixture was concentrated. The residue was purified by pre-HPLC to get product 347 (23 mg). m/z 372 [M+1]

Example 17

Preparation of Compound 348

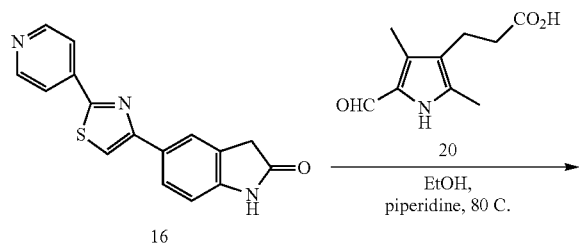

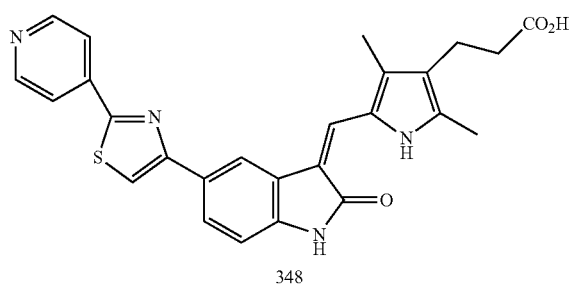

Step 1

To a suspension of 16 (59 mg, 0.2 mmol) in EtOH (3 mL) was added 20 (42 mg, 0.22 mmol) and piperidine (one drop). The resulted mixture was heated at 80 C for 16 h before cooled down. The reaction mixture was concentrated and neutralized to pH=4-5. The residue was purified by pre-HPLC to get product 348 (25 mg). m/z 471 [M+1]

Example 18

Preparation of Compound 349

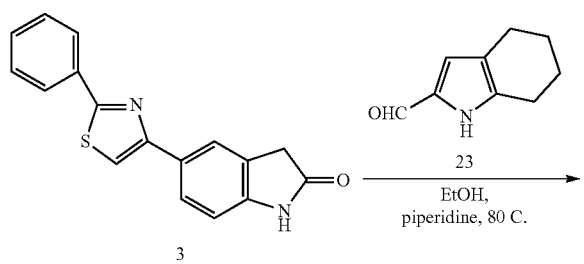

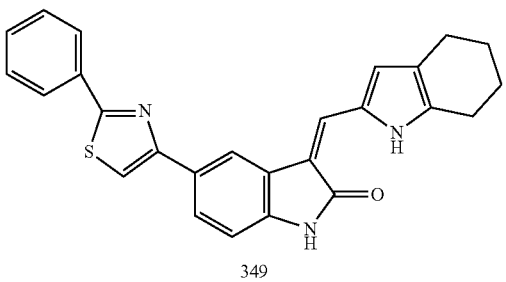

Step 1

To a suspension of 3 (58 mg, 0.2 mmol) in EtOH (3 mL) was added 23 (33 mg, 0.22 mmol) and piperidine (one drop). The resulted mixture was heated at 80 C for 16 h before cooled down. The reaction mixture was concentrated. The residue was purified by pre-HPLC to get product 349 (20 mg). m/z 424 [M+1]

Example 19

Preparation of Compound 350

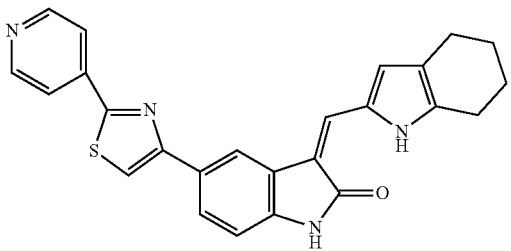

Step 1

To a suspension of 16 (59 mg, 0.2 mmol) in EtOH (3 mL) was added 23 (33 mg, 0.22 mmol) and piperidine (one drop). The resulted mixture was heated at 80 C for 16 h before cooled down. The reaction mixture was concentrated. The residue was purified by pre-HPLC to get product 350 (65 mg). m/z 425 [M+1]

Example 20

Preparation of Compound 351

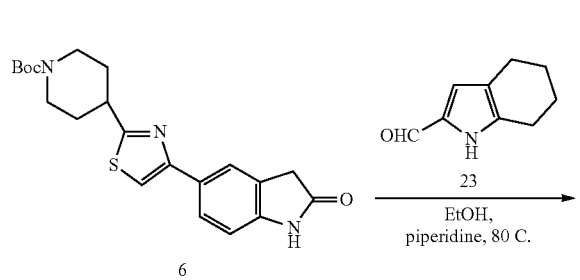

6

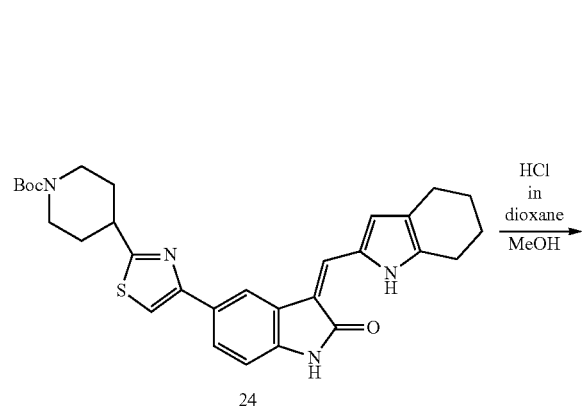

24

351

Step 1

To a suspension of 6 (80 mg, 0.2 mmol) in EtOH (3 mL) was added 23 (33 mg, 0.22 mmol) and piperidine (0.1 mL). The resulted mixture was heated at 80 C for 2 h before cooled down. The reaction mixture was concentrated. The residue was partitioned in EtOAc and H2O. The organic layer was washed with H2O, and brine, dried over Na2SO4, and concentrated in vacuo. The residue was purified by pre-HPLC to get product 24.

Step 2

To a solution of 24 (53 mg, 0.13 mmol) in MeOH (5 mL) was added HCl (4N in dioxane, 1 mL). The resulted mixture was stirred at room temperature for over night. The reaction mixture was concentrated. The residue was purified by pre-HPLC to get product 351 (13 mg). m/z 431 [M+1]

Example 21

Preparation of Compound 352

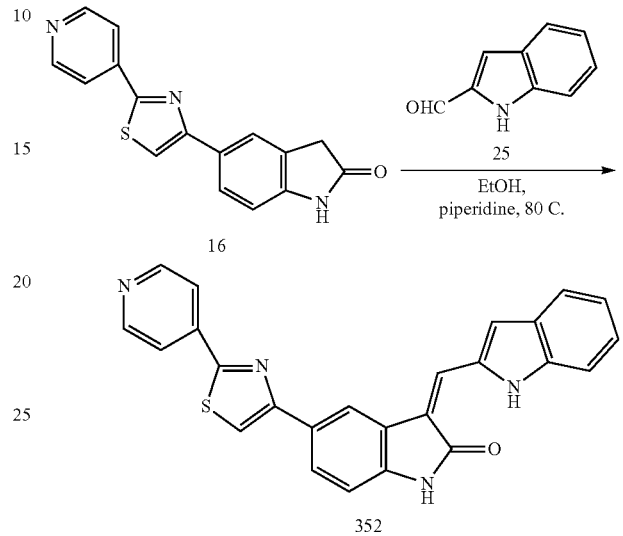

16

352

Step 1

To a suspension of 16 (59 mg, 0.2 mmol) in EtOH (3 mL) was added 25 (31 mg, 0.22 mmol) and piperidine (one drop). The resulted mixture was heated at 80 C for 16 h before cooled down. The reaction mixture was concentrated. The residue was purified by pre-HPLC to get product 352 (48 mg). m/z 421 [M+1]

Example 22

Preparation of Compound 353

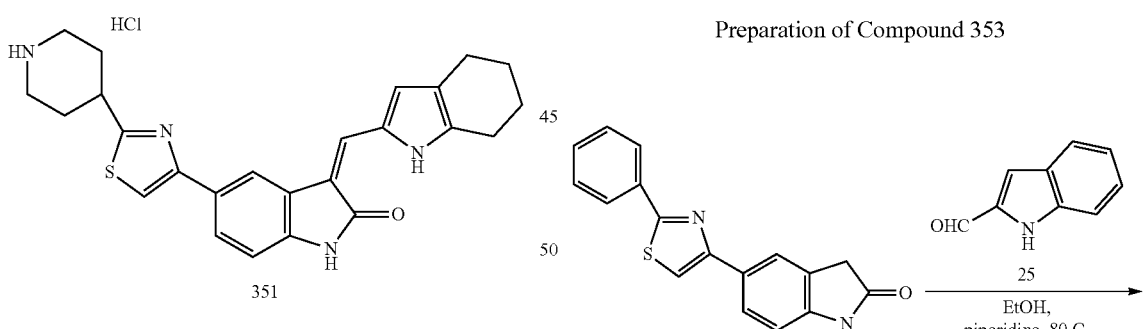

3

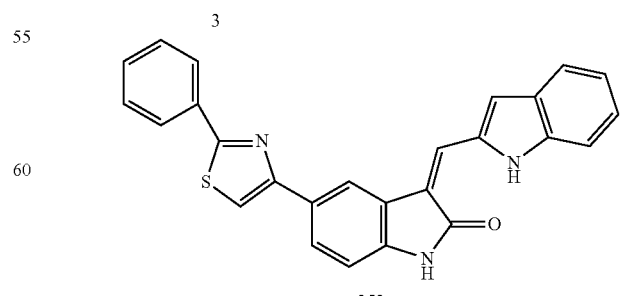

353

Step 1

To a suspension of 3 (58 mg, 0.2 mmol) in EtOH (3 mL) was added 25 (31 mg, 0.22 mmol) and piperidine (one drop). The resulted mixture was heated at 80 C for 16 h before cooled down. The reaction mixture was concentrated. The residue was purified by pre-HPLC to get product 353 (26 mg). m/z 420 [M+1]

Example 23

Preparation of Compound 354

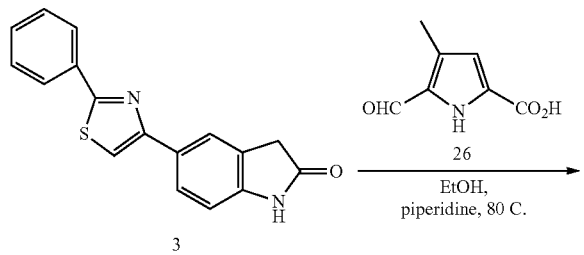

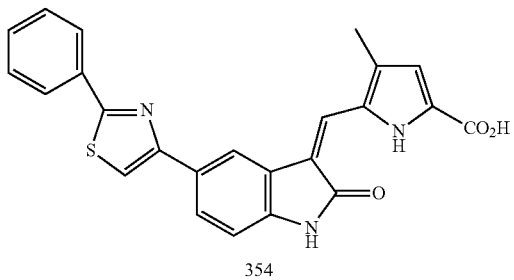

354

Step 1

To a suspension of 3 (58 mg, 0.2 mmol) in EtOH (3 mL) was added 26 (33 mg, 0.22 mmol) and piperidine (one drop). The resulted mixture was heated at 80 C for 16 h before cooled down. The reaction mixture was adjusted pH to 5 and concentrated. The residue was purified by pre-HPLC to get product 354 (35 mg). m/z 428 [M+1]

Example 24

Preparation of Compound 355

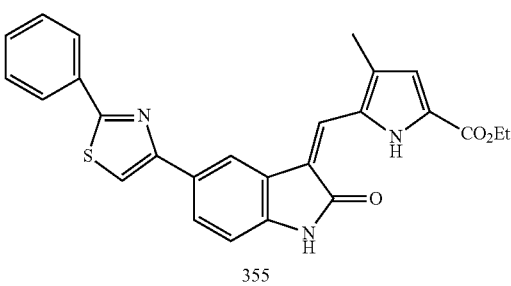

-continued

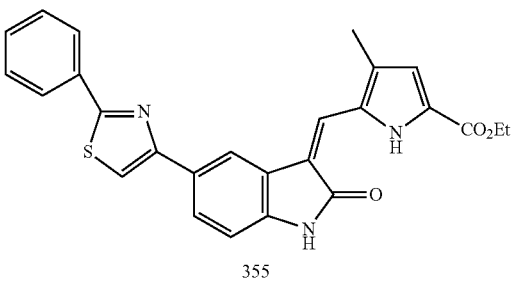

355

Step 1

To a suspension of 3 (58 mg, 0.2 mmol) in EtOH (3 mL) was added 27 (41 mg, 0.22 mmol) and piperidine (one drop). The resulted mixture was heated at 80 C for 16 h before cooled down. The reaction mixture was concentrated. The residue was purified by pre-HPLC to get product 355 (41 mg). m/z 456 [M+1]

Example 25

Preparation of Compound 356

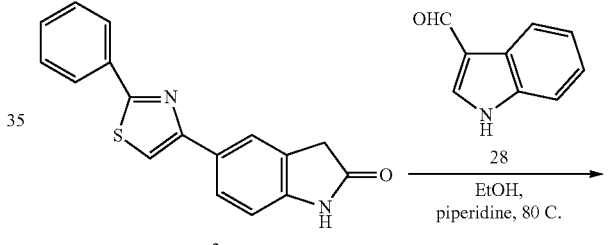

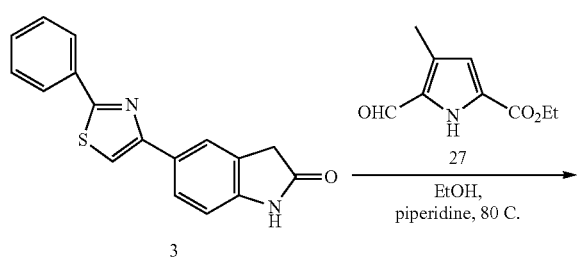

356

Step 1

To a suspension of 3 (58 mg, 0.2 mmol) in EtOH (3 mL) was added 28 (31 mg, 0.22 mmol) and piperidine (one drop). The resulted mixture was heated at 80 C for 16 h before cooled down. The reaction mixture was concentrated. The residue was purified by pre-HPLC to get product 356 (35 mg). m/z 420 [M+1]

Example 26

Preparation of Compound 357

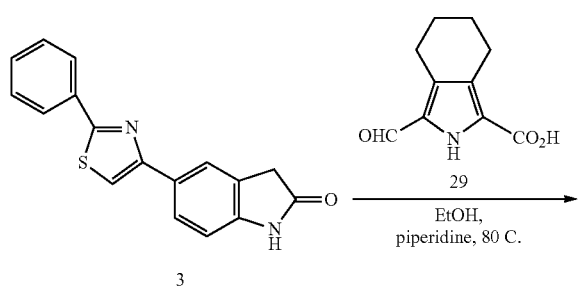

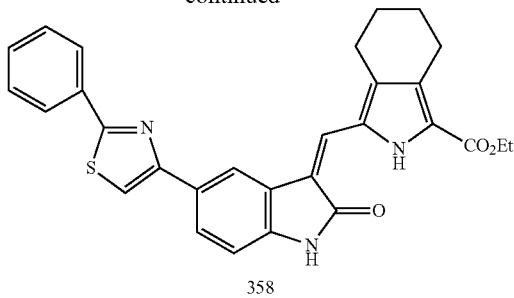
358

Step 1
To a suspension of 3 (58 mg, 0.2 mmol) in EtOH (3 mL) was added 30 (46 mg, 0.22 mmol) and piperidine (one drop). The resulted mixture was heated at 80 C for 16 h before cooled down. The reaction mixture was concentrated. The residue was purified by pre-HPLC to get product 358 (40 mg). m/z 496 [M+1]

Example 28

Preparation of Compound 362

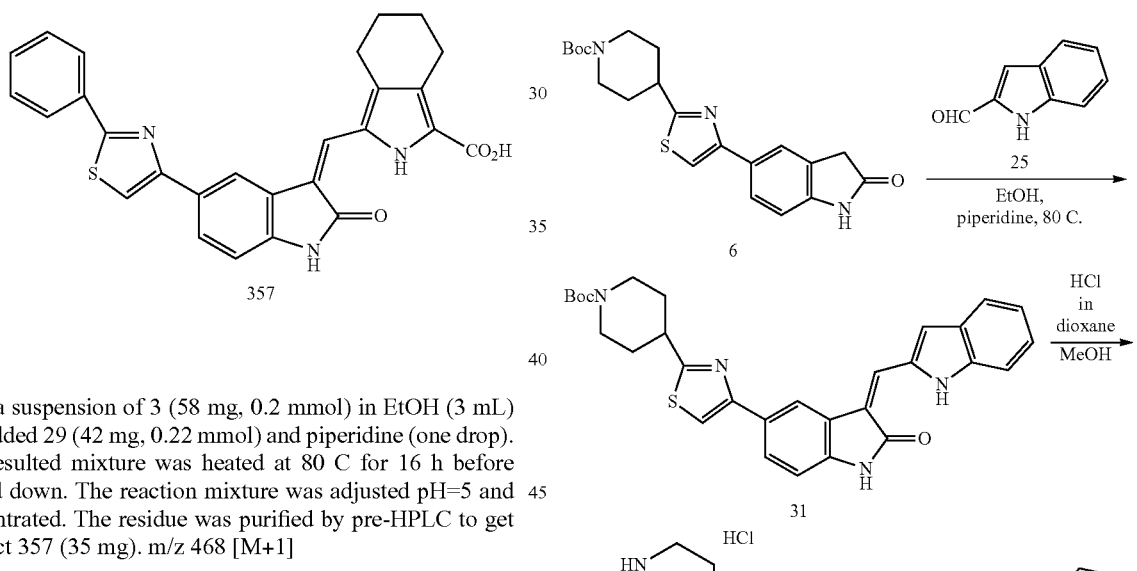

Step 1
To a suspension of 3 (58 mg, 0.2 mmol) in EtOH (3 mL) was added 29 (42 mg, 0.22 mmol) and piperidine (one drop). The resulted mixture was heated at 80 C for 16 h before cooled down. The reaction mixture was adjusted pH=5 and concentrated. The residue was purified by pre-HPLC to get product 357 (35 mg). m/z 468 [M+1]

Example 27

Preparation of Compound 358

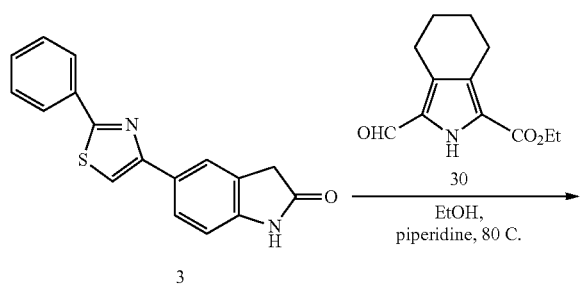

Step 1
To a suspension of 6 (80 mg, 0.2 mmol) in EtOH (3 mL) was added 23 (32 mg, 0.22 mmol) and piperidine (0.1 mL). The resulted mixture was heated at 80 C for 2 h before cooled down. The reaction mixture was concentrated. The residue was partitioned in EtOAc and H2O. The organic layer was washed with H2O, and brine, dried over Na2SO4, and concentrated in vacuo. The residue was purified by pre-HPLC to get product 31.

Step 2

To a solution of 31 (25 mg, 0.05 mmol) in MeOH (5 mL) was added HCl (4N in dioxane, 1 mL). The resulted mixture was stirred at rt for overnight and concentrated. The residue was purified by pre-HPLC to get product 362 (18 mg). m/z 427 [M+1]

Example 29

Preparation of Compound 359

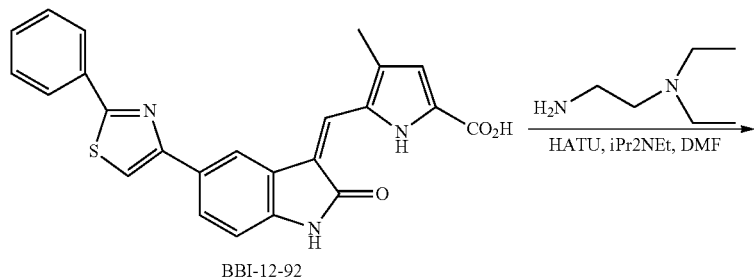
BBI-12-92

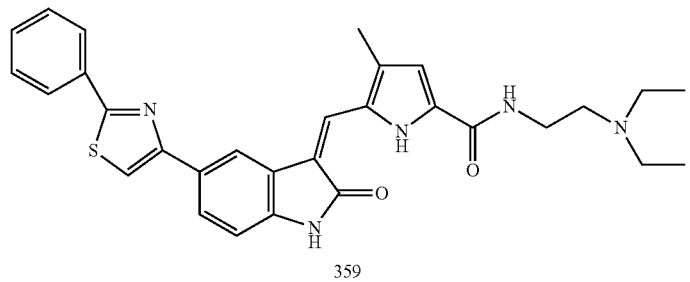
359

Step 1

To a solution of BBI-12-92 (43 mg, 0.1 mmol) in DMF (2 mL) was added HATU (69 mg), diisopropylethylamine (500 uL), and diethylethylenediamine (25 mg). The mixture was stirred at room temperature for 16 hours then concentrated in vacuo. The residue was added $CH_2Cl_2$ and washed with $H_2O$. The organic layer was dried over $Na_2SO_4$ and concentrated in vacuo. The residue was purified by pre-HPLC to get product 359 (35 mg). m/z 526 [M+1]

Example 30

Preparation of Compound 360

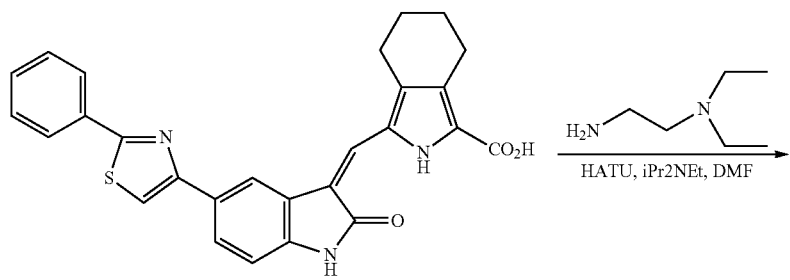
BBI-12-93

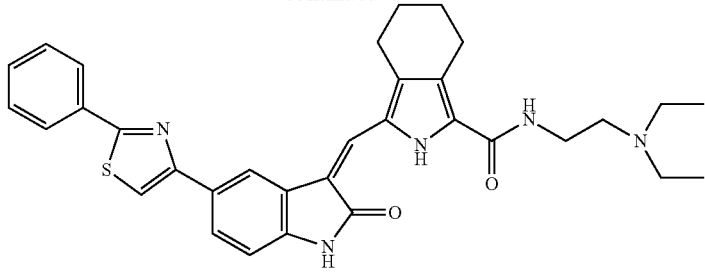

360

Step 1

To a solution of BBI-12-92 (47 mg, 0.1 mmol) in DMF (2 mL) was added HATU (69 mg), diisopropylethylamine (500 uL), and diethylethylenediamine (25 mg). The mixture was stirred at room temperature for 16 hours then concentrated in vacuo. The residue was added $CH_2Cl_2$ and washed with $H_2O$. The organic layer was dried over $Na_2SO_4$ and concentrated in vacuo. The residue was purified by pre-HPLC to get product 360 (37 mg). m/z 566 [M+1]

Example 31

Preparation of Compound 361

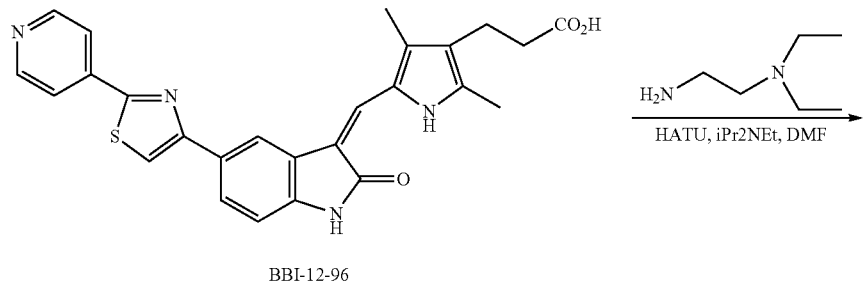

BBI-12-96

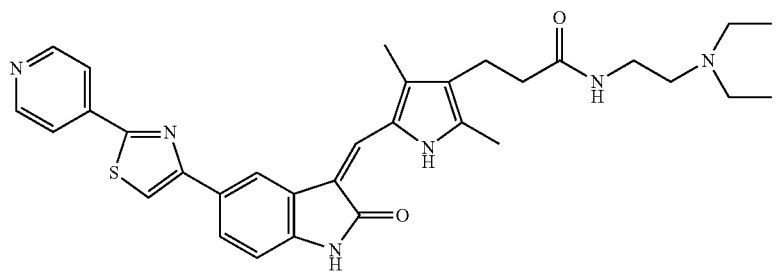

361

Step 1

To a solution of BBI-12-96 (47 mg, 0.1 mmol) in DMF (2 mL) was added HATU (69 mg), diisopropylethylamine (500 uL), diethylethylenediamine (25 mg). The mixture was stirred at room temperature for 16 hours then concentrated in vacuo. The residue was added $CH_2Cl_2$ and washed with $H_2O$. The organic layer was dried over $Na_2SO_4$ and concentrated in vacuo. The residue was purified by pre-HPLC to get product 361 (18 mg). m/z 569 [M+1]

Example 32

Preparation of Compound 364

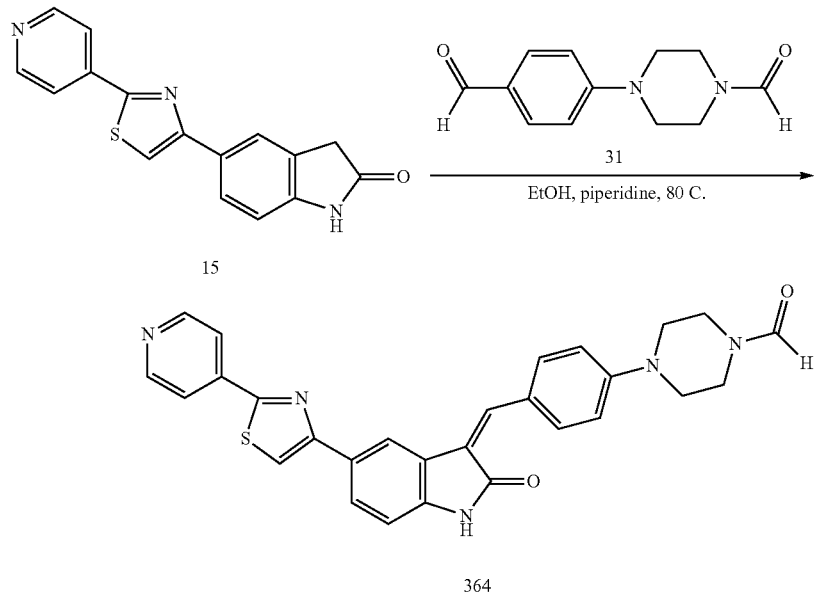

Step 1

To a suspension of 15 (59 mg, 0.2 mmol) in EtOH (3 mL) was added 31 (47 mg, 0.22 mmol) and piperidine (0.1 mL). The resulted mixture was heated at 80 C for 16 h before cooled down. The reaction mixture was concentrated. The residue was purified by pre-HPLC to get product 364 (43 mg). m/z 494 [M+1]

Example 33

Preparation of Compound 365

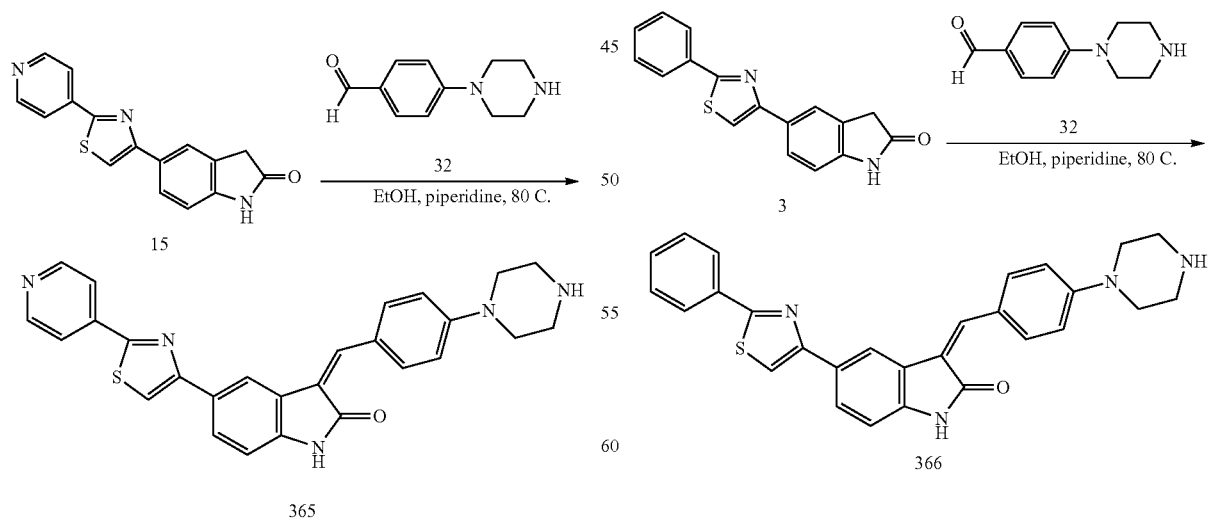

Step 1

To a suspension of 15 (59 mg, 0.2 mmol) in EtOH (3 mL) was added 32 (42 mg, 0.22 mmol) and piperidine (0.1 mL). The resulted mixture was heated at 80 C for 16 h before cooled down. The reaction mixture was concentrated. The residue was purified by pre-HPLC to get product 365 (25 mg). m/z 466 [M+1]

Example 34

Preparation of Compound 366

Step 1

To a suspension of 3 (58 mg, 0.2 mmol) in EtOH (3 mL) was added 32 (42 mg, 0.22 mmol) and piperidine (0.1 mL). The resulted mixture was heated at 80 C for 16 h before cooled down. The reaction mixture was concentrated. The residue was purified by pre-HPLC to get product 366 (26 mg). m/z 465 [M+1]

Example 35

Preparation of Compound 367

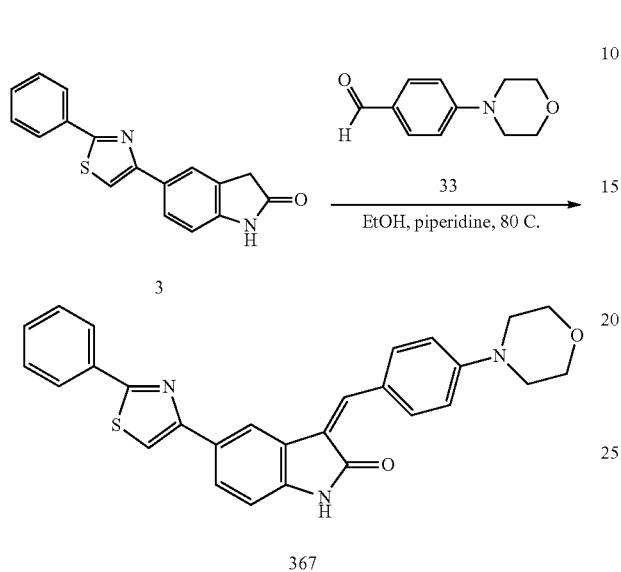

Step 1

To a suspension of 3 (58 mg, 0.2 mmol) in EtOH (3 mL) was added 32 (42 mg, 0.22 mmol) and piperidine (0.1 mL). The resulted mixture was heated at 80 C for 16 h before cooled down. The reaction mixture was concentrated. The residue was purified by pre-HPLC to get product 367 (42 mg). m/z 466 [M+1]

Example 36

Preparation of Compound 368

Step 1

To a suspension of 15 (59 mg, 0.2 mmol) in EtOH (3 mL) was added 32 (42 mg, 0.22 mmol) and piperidine (0.1 mL). The resulted mixture was heated at 80 C for 16 h before cooled down. The reaction mixture was concentrated. The residue was purified by pre-HPLC to get product 368 (39 mg). m/z 467 [M+1]

Example 37

Preparation of Compound 369

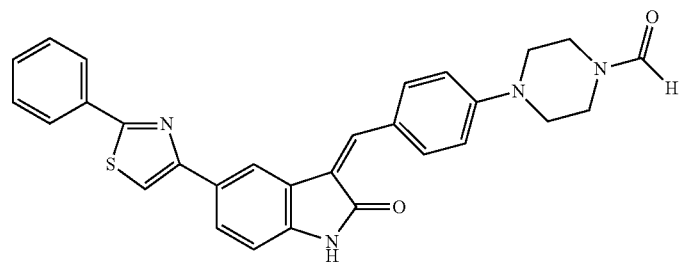

Step 1

To a suspension of 15 (59 mg, 0.2 mmol) in EtOH (3 mL) was added 31 (47 mg, 0.22 mmol) and piperidine (0.1 mL). The resulted mixture was heated at 80 C for 16 h before cooled down. The reaction mixture was concentrated. The residue was purified by pre-HPLC to get product BBI-12-124 (37 mg). m/z 494 [M+1]

Example 38

Preparation of Compound 370

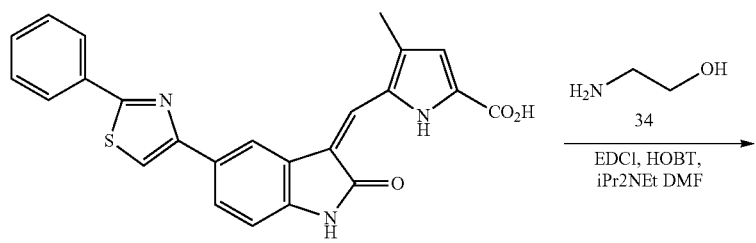

BBI-12-92

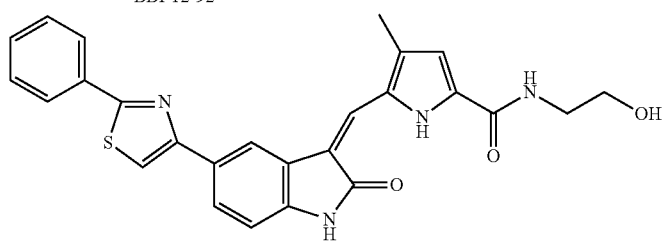

370

Step 1

To a solution of BBI-12-92 (64 mg, 0.15 mmol) in DMF (2 mL) was added EDCI (58 mg, 0.3 mmol), HOBT (41 mg, 0.3 mmol), diisopropylethylamine (78 uL, 0.45 mmol), and amine 34 (68 uL). The mixture was stirred at room temperature for 24 hours then was added CH$_2$Cl$_2$ (20 mL) and washed with H$_2$O. The organic layer was dried over Na$_2$SO$_4$ and concentrated in vacuo. The residue was purified by pre-HPLC to get product 370 (19 mg). m/z 471 [M+1]

Example 39

Preparation of Compound 371

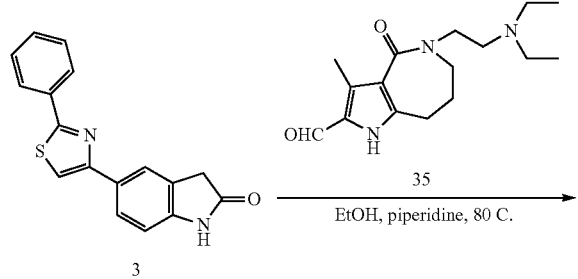

-continued

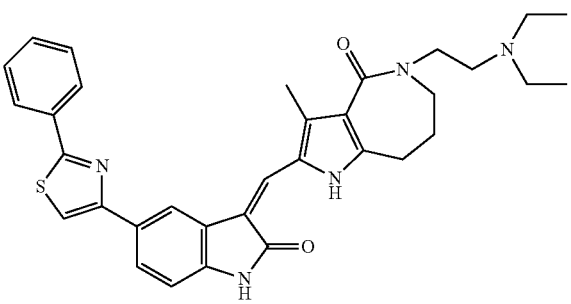

371

Step 1

To a suspension of 3 (58 mg, 0.2 mmol) in EtOH (3 mL) was added 35 (65 mg, 0.22 mmol) and piperidine (0.1 mL). The resulted mixture was heated at 80 C for 16 h before cooled down. The reaction mixture was concentrated. The residue was purified by pre-HPLC to get product 371 (25 mg). m/z 566 [M+1]

Example 40

Preparation of Compound 372

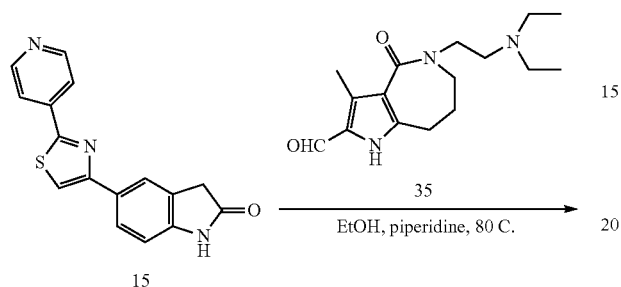

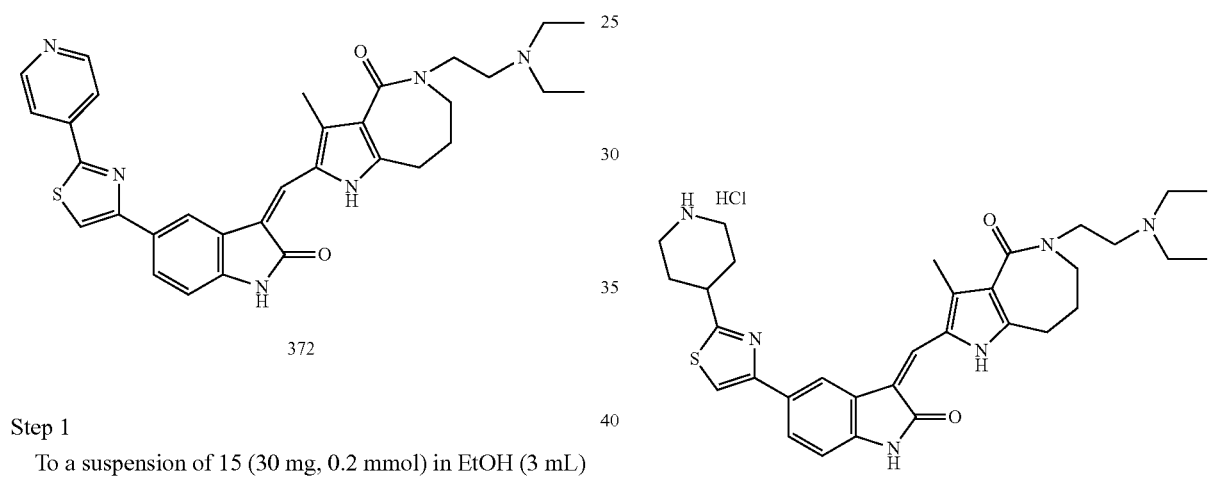

Step 1

To a suspension of 15 (30 mg, 0.2 mmol) in EtOH (3 mL) was added 35 (38 mg, 0.22 mmol) and piperidine (0.1 mL). The resulted mixture was heated at 80 C for 16 h before cooled down. The reaction mixture was concentrated. The residue was purified by pre-HPLC to get product 372 (11 mg). m/z 567 [M+1]

Example 41

Preparation of Compound 373

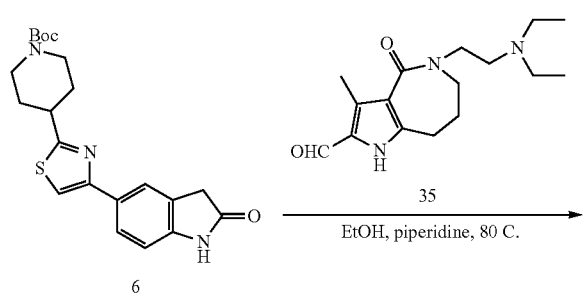

Step 1

To a suspension of 6 (40 mg, 0.1 mmol) in EtOH (3 mL) was added 35 (40 mg, 0.13 mmol) and piperidine (0.1 mL). The resulted mixture was heated at 80 C for 16 h before cooled down. The reaction mixture was concentrated. The residue was purified by pre-HPLC to get product 36.

Step 2

To a solution of 36 (34 mg, 0.1 mmol) in MeOH (5 mL) was added HCl (4N in dioxane, 1 mL). The resulted mixture was stirred at room temperature for overnight. The reaction mixture was concentrated. The residue was purified by pre-HPLC to get product 373 (28 mg). m/z 573 [M+1]

Example 42

Preparation of Compound 233 and 234

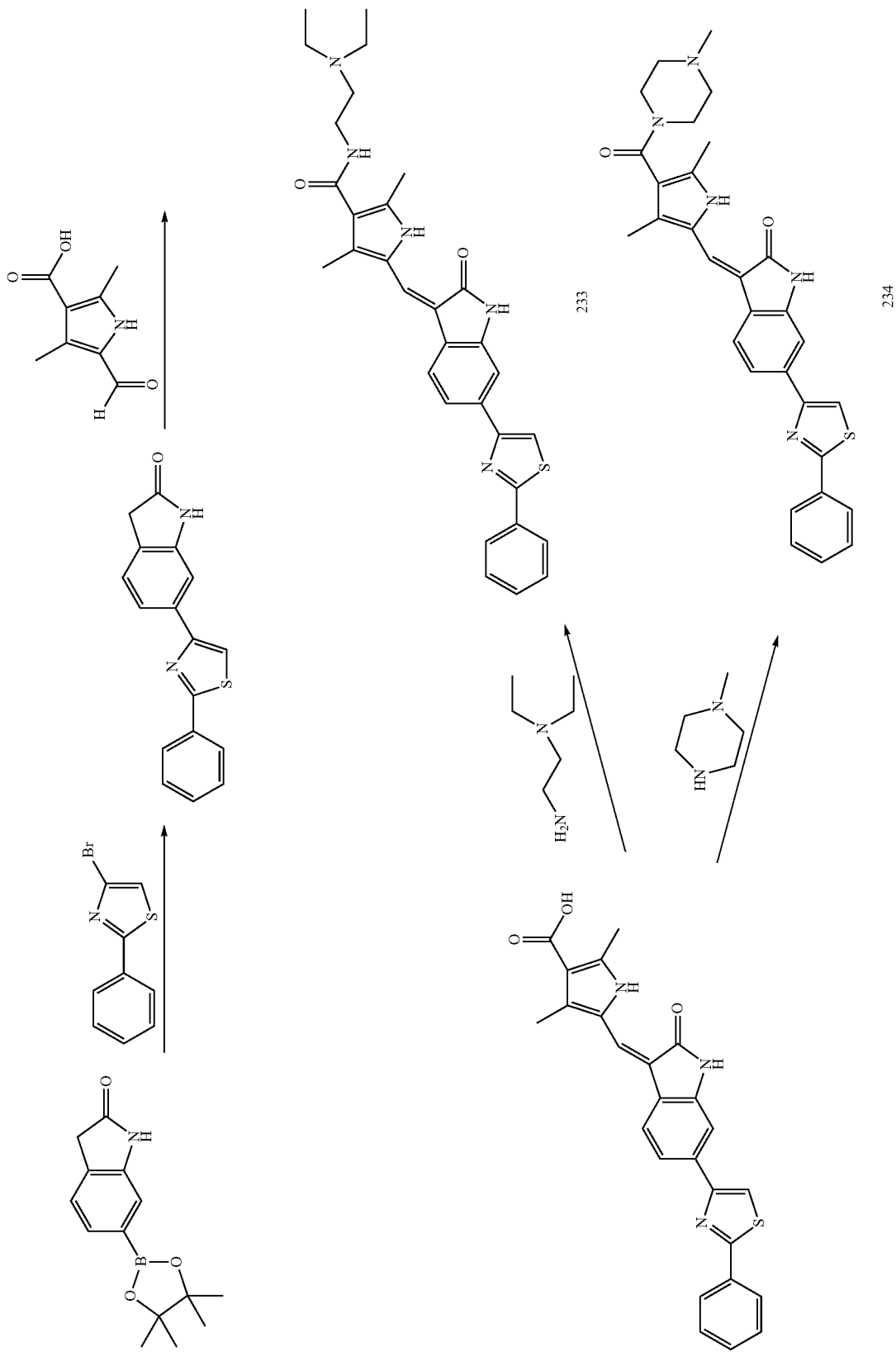

Example 43
Preparation of Compound 235 and 236
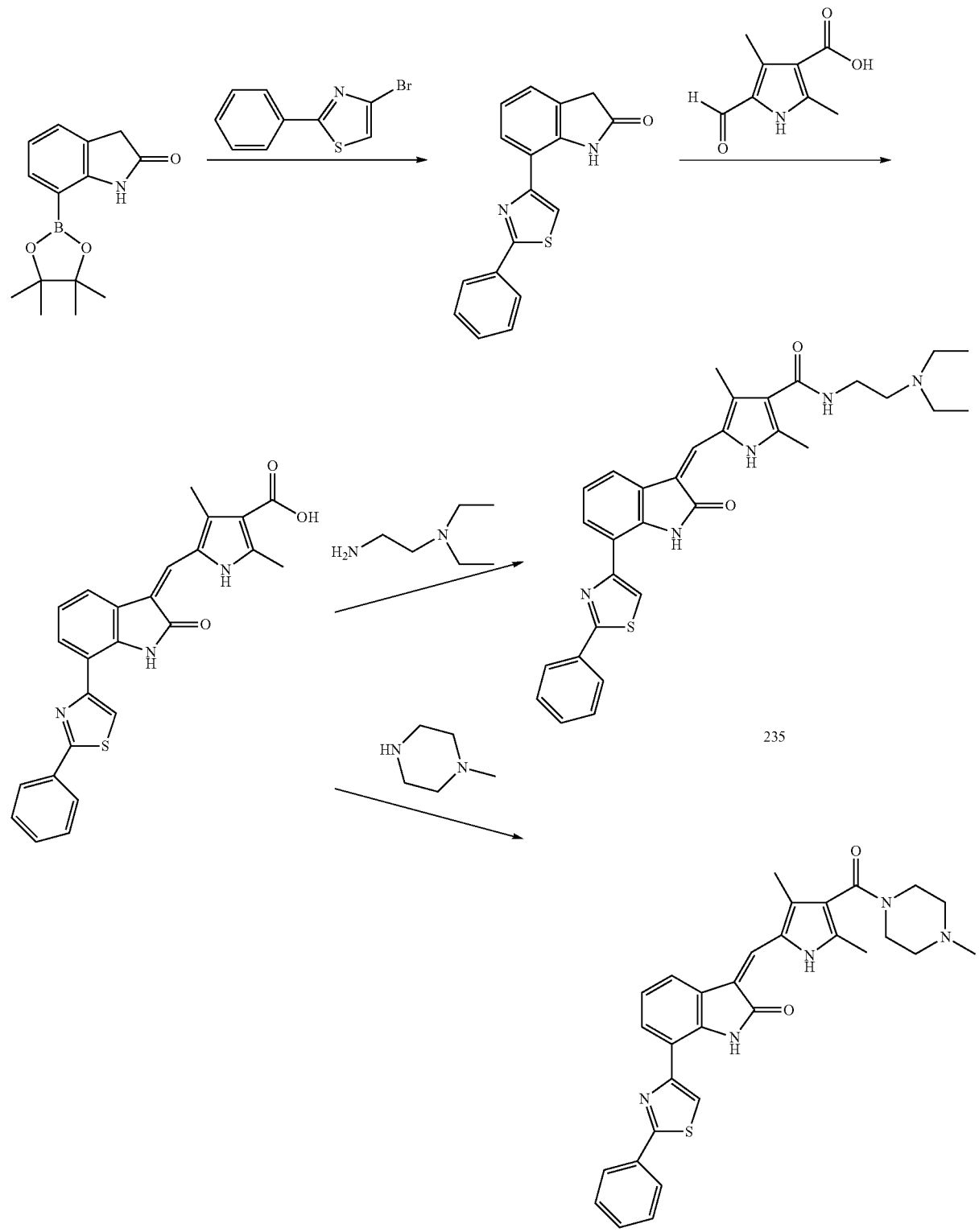

Example 44
Preparation of Compound 238, 239, 243 and 241
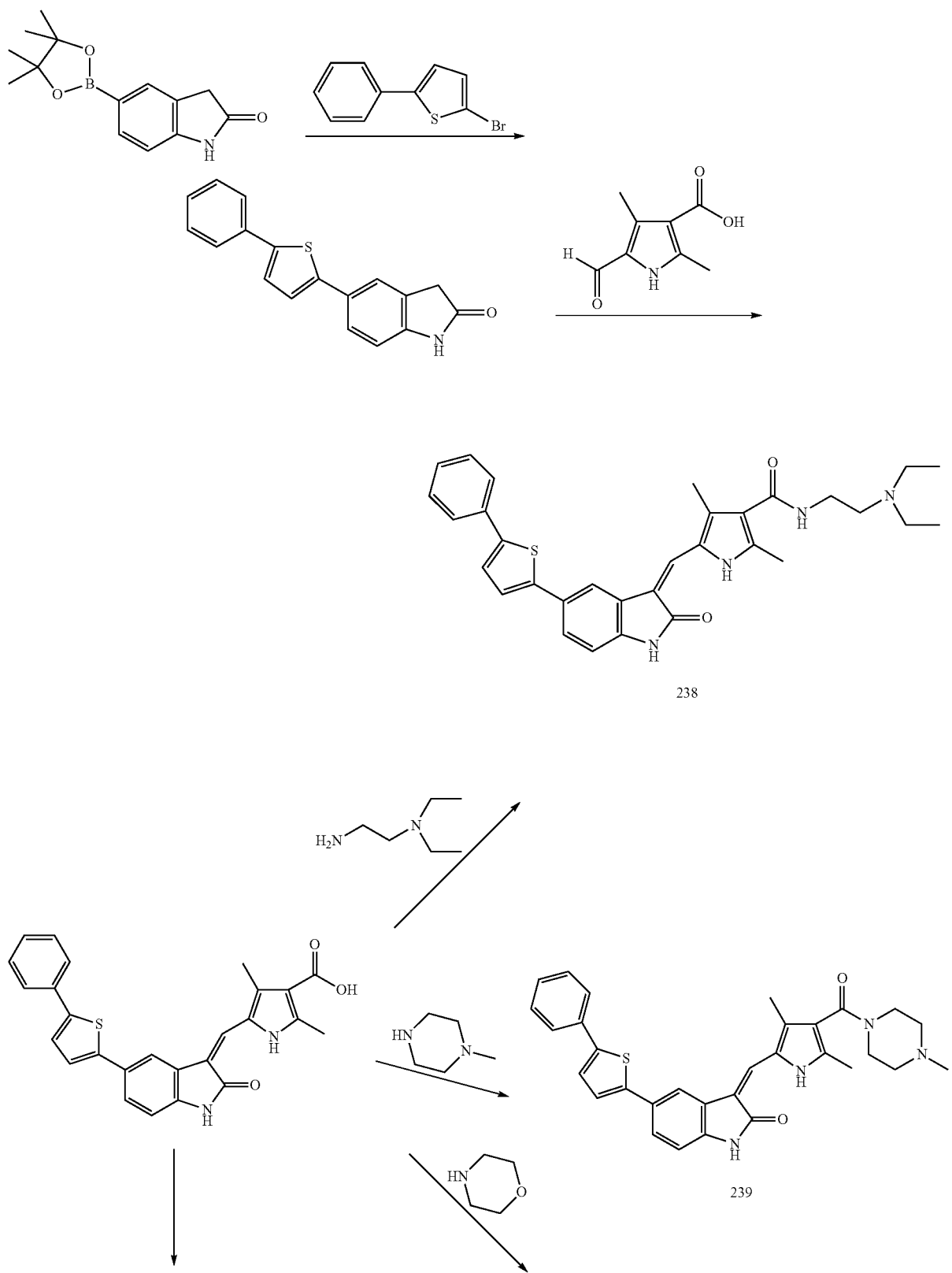

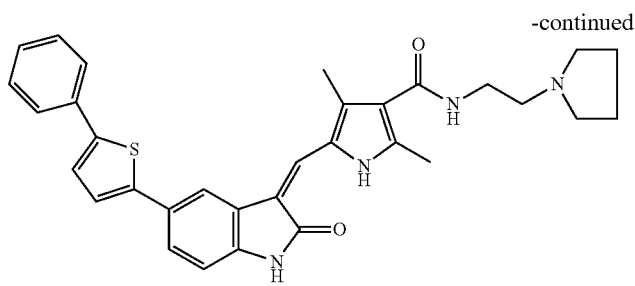
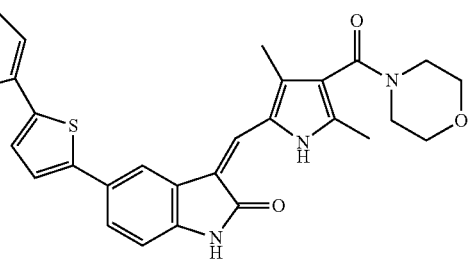
Example 45
Preparation of Compound DSR-240, and 242
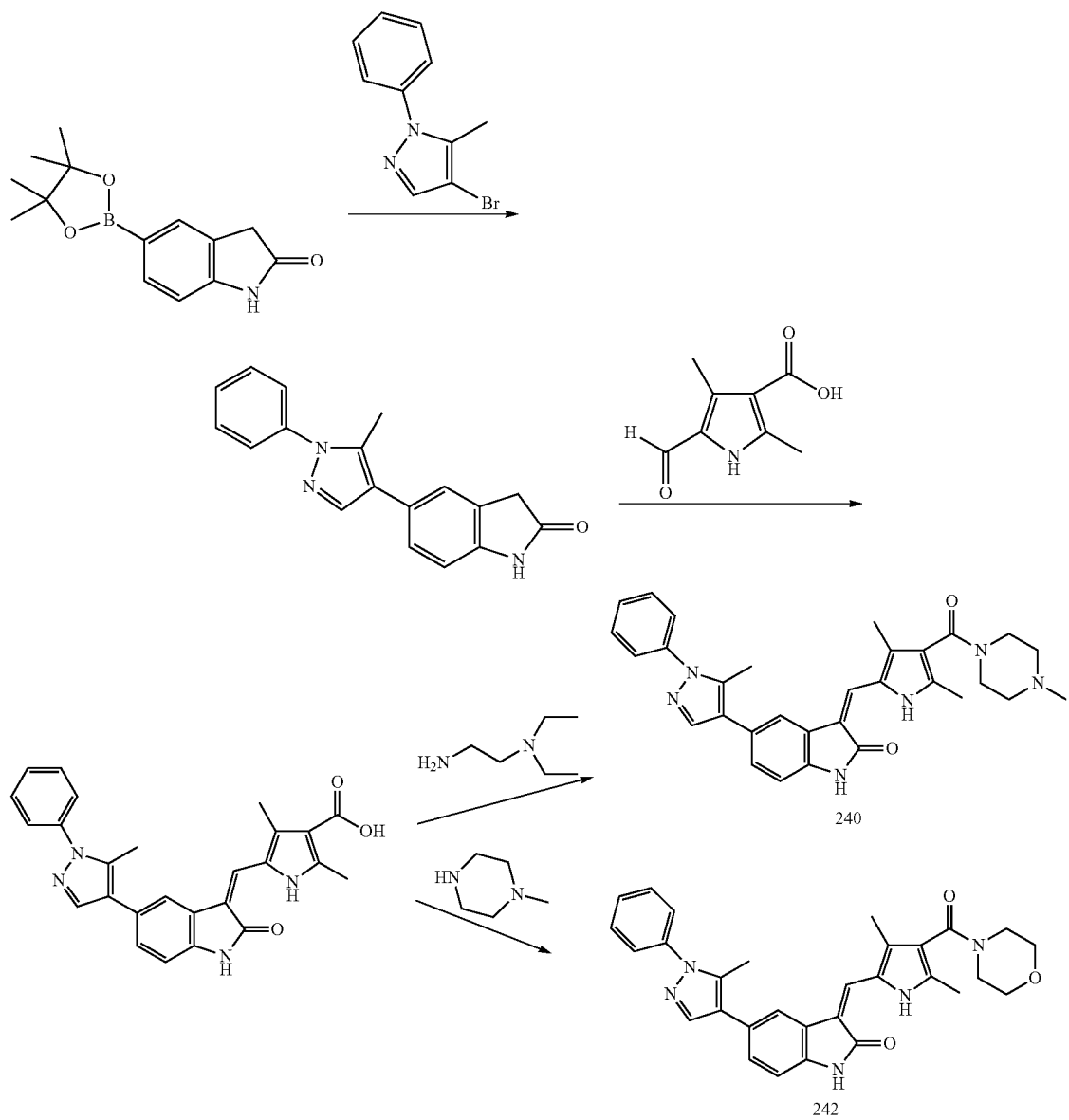

Example 46
Preparation of Compound 244
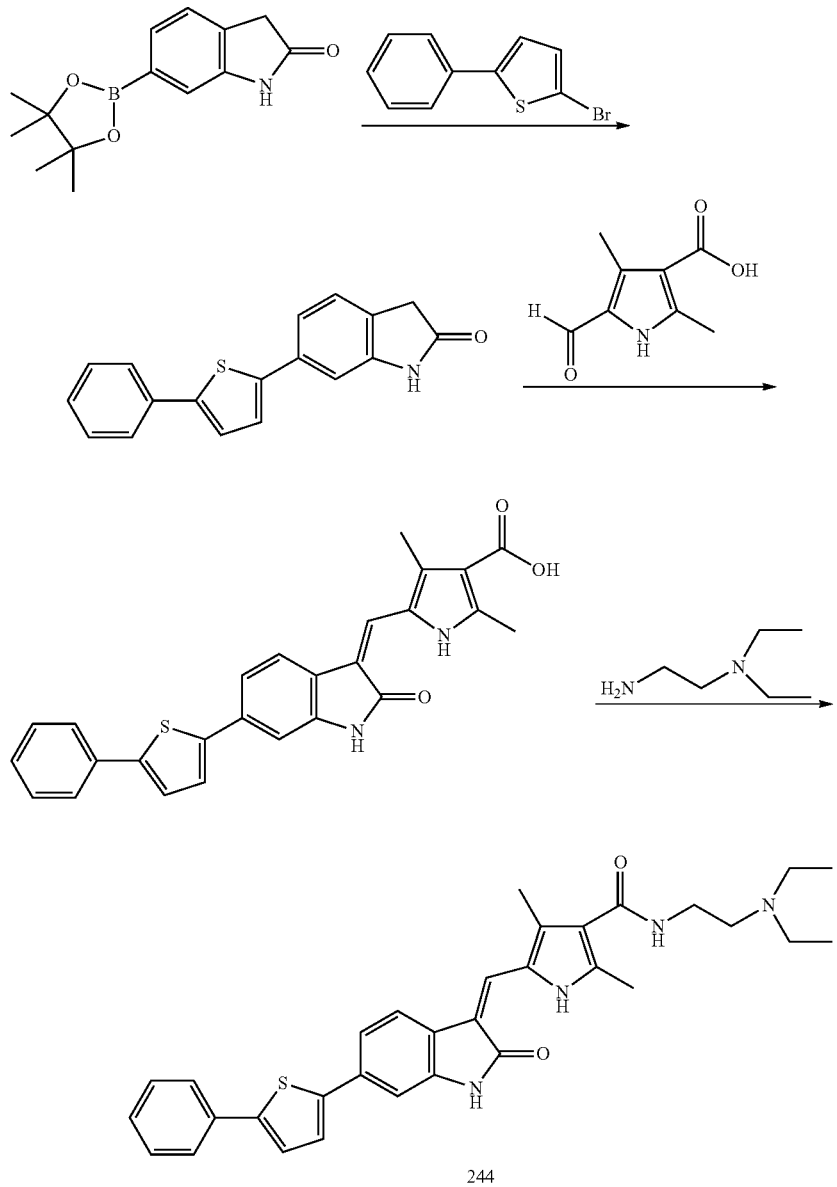
244
Example 47
Preparation of Compound 245 and 246
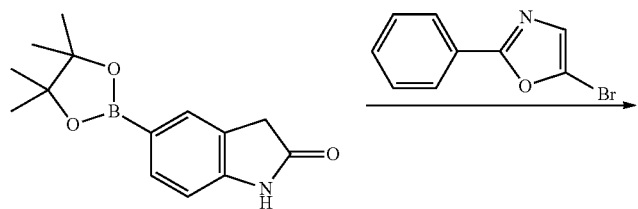

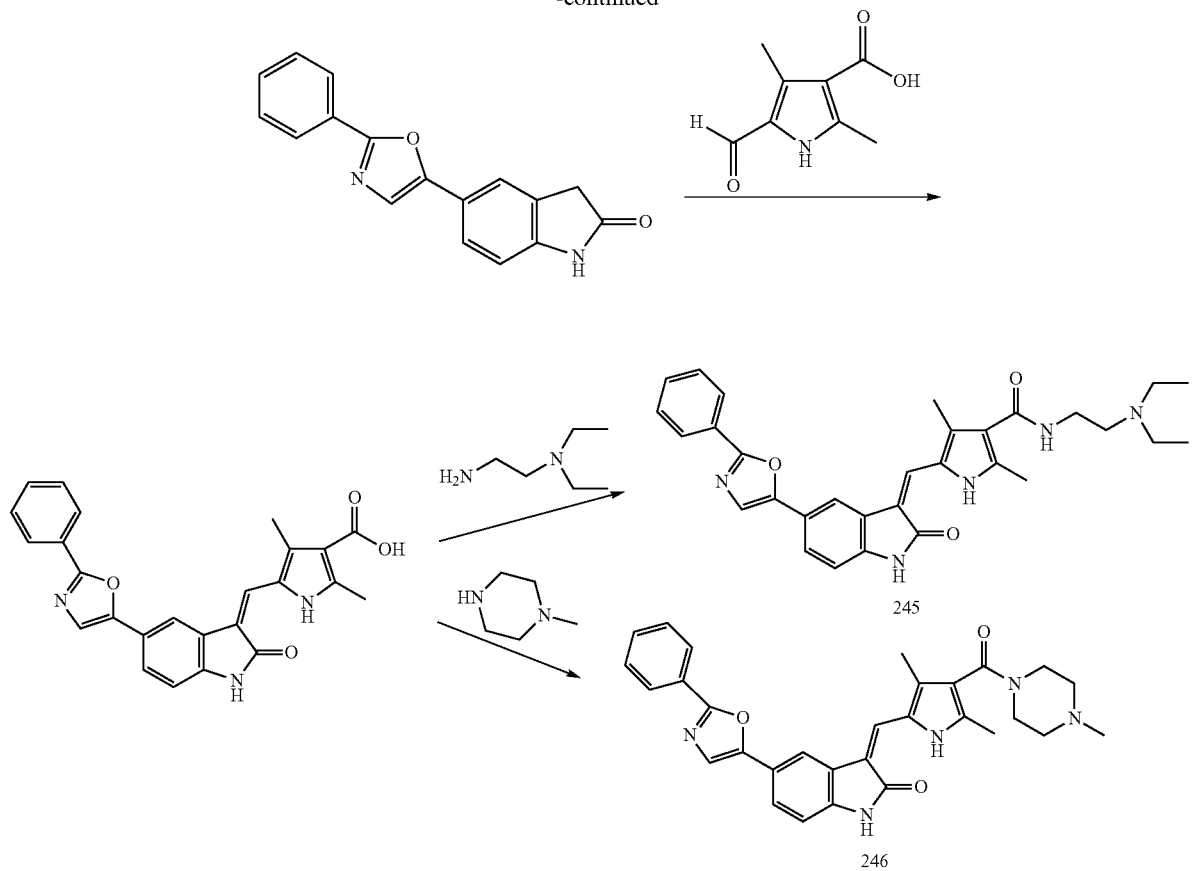
Example 48
Preparation of Compound 247, 248 and 249
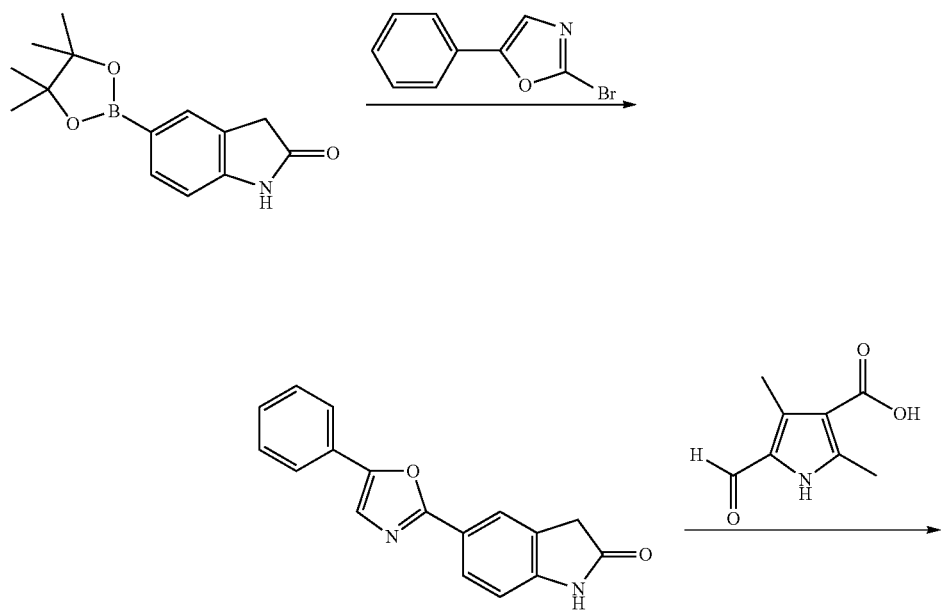

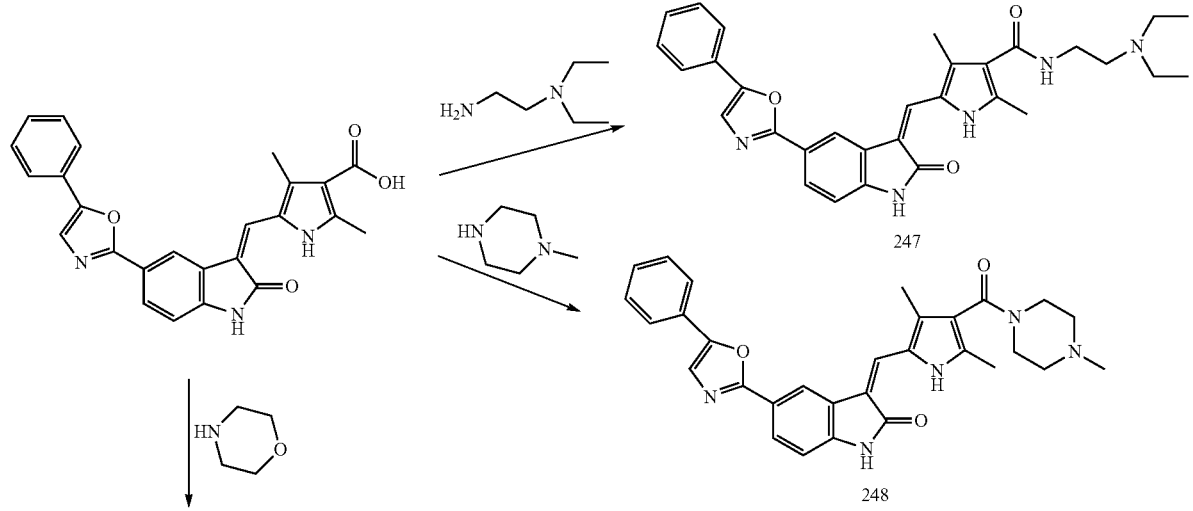
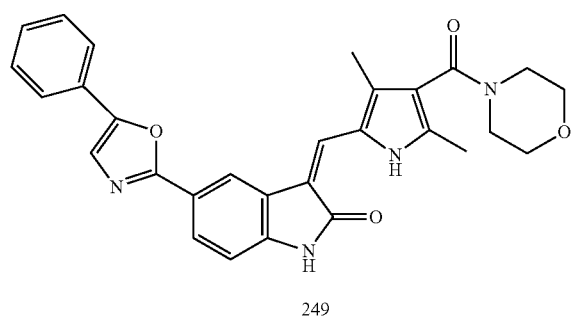
Example 49
Preparation of Compound 250
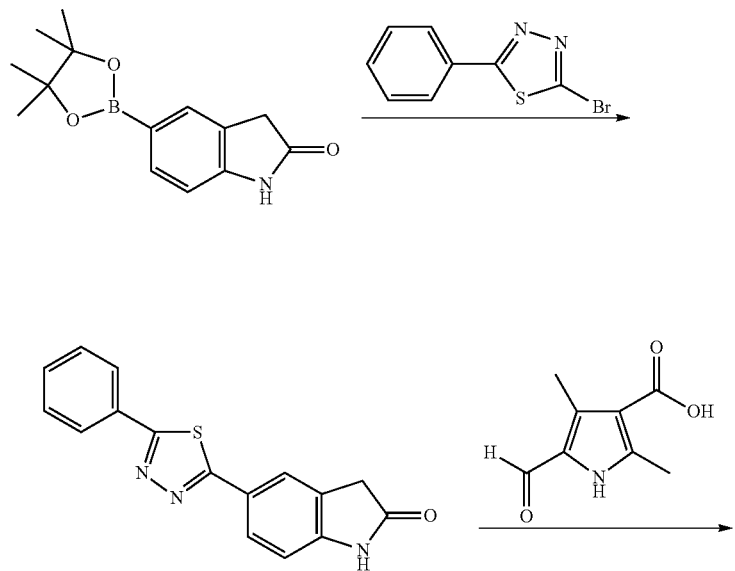

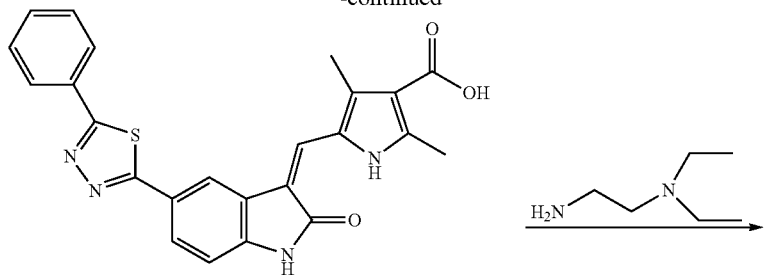
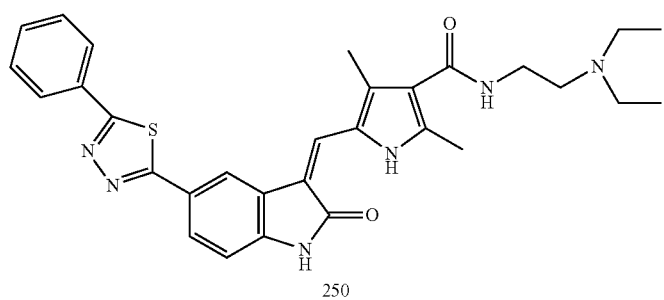
250
Example 50
Preparation of Compound 251 and 252
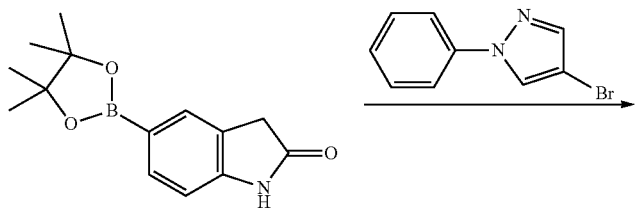
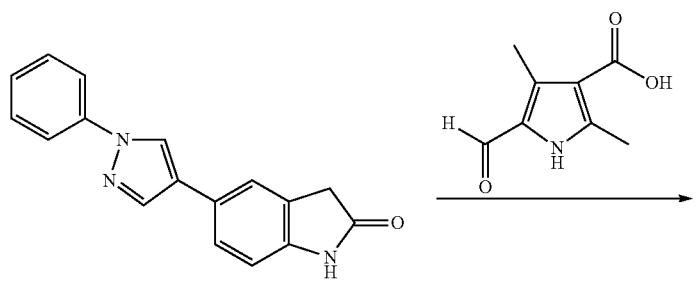

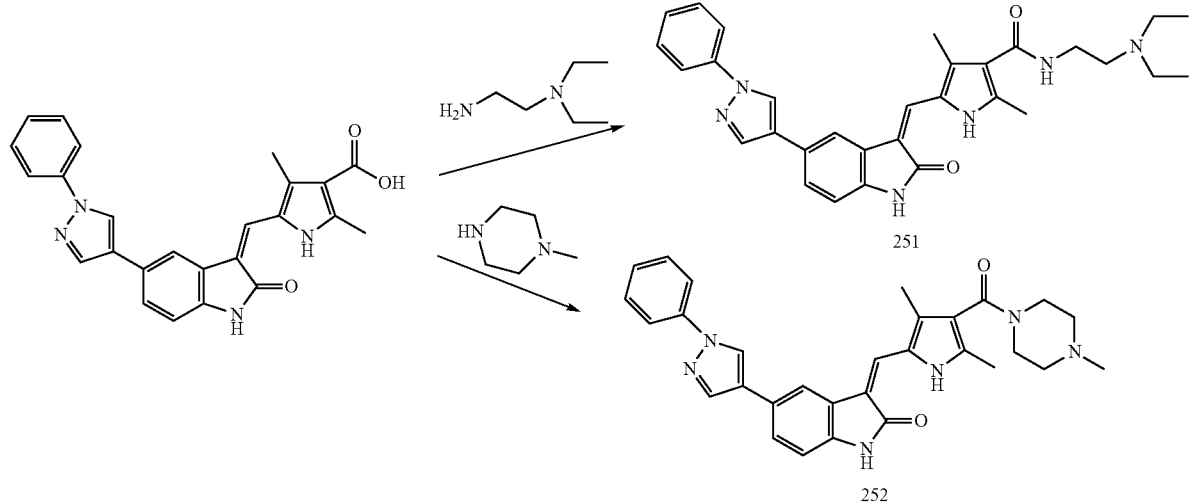
Example 51
Preparation of Compound 253 and 254
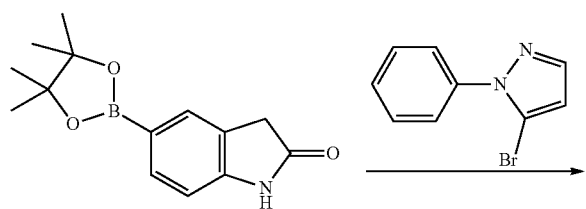
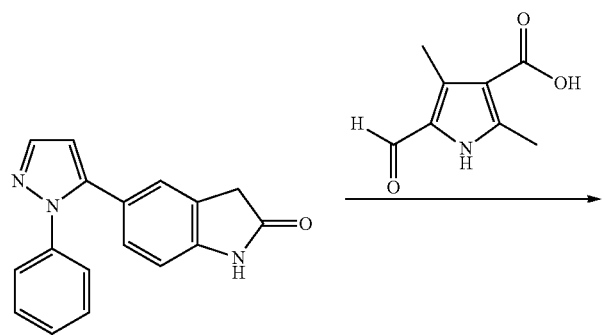

-continued
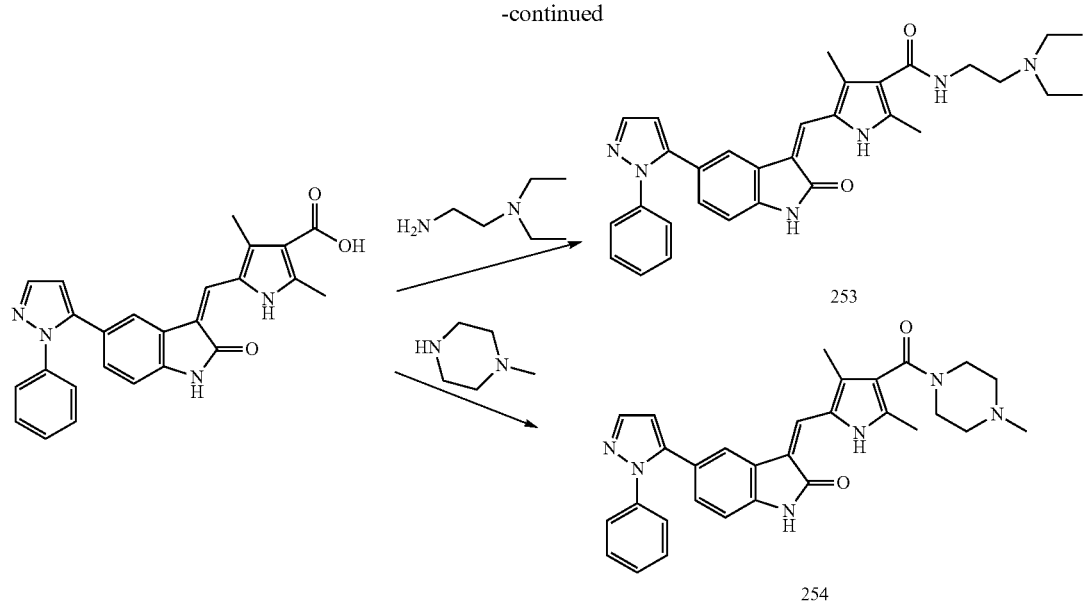
Example 52
Preparation of Compound 256 and 255
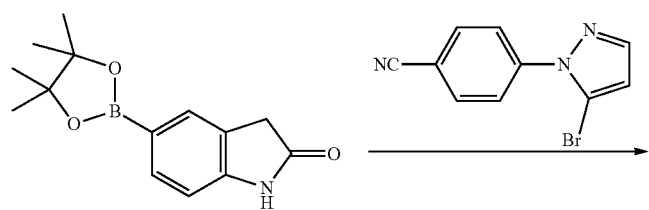
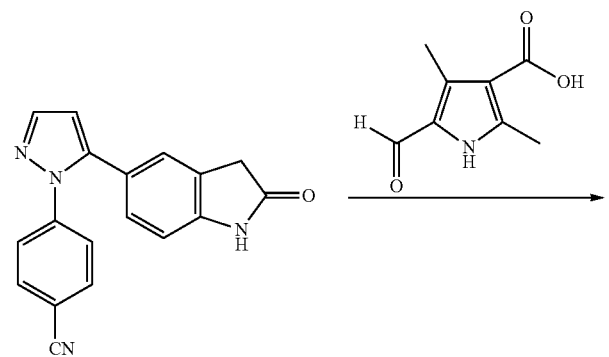

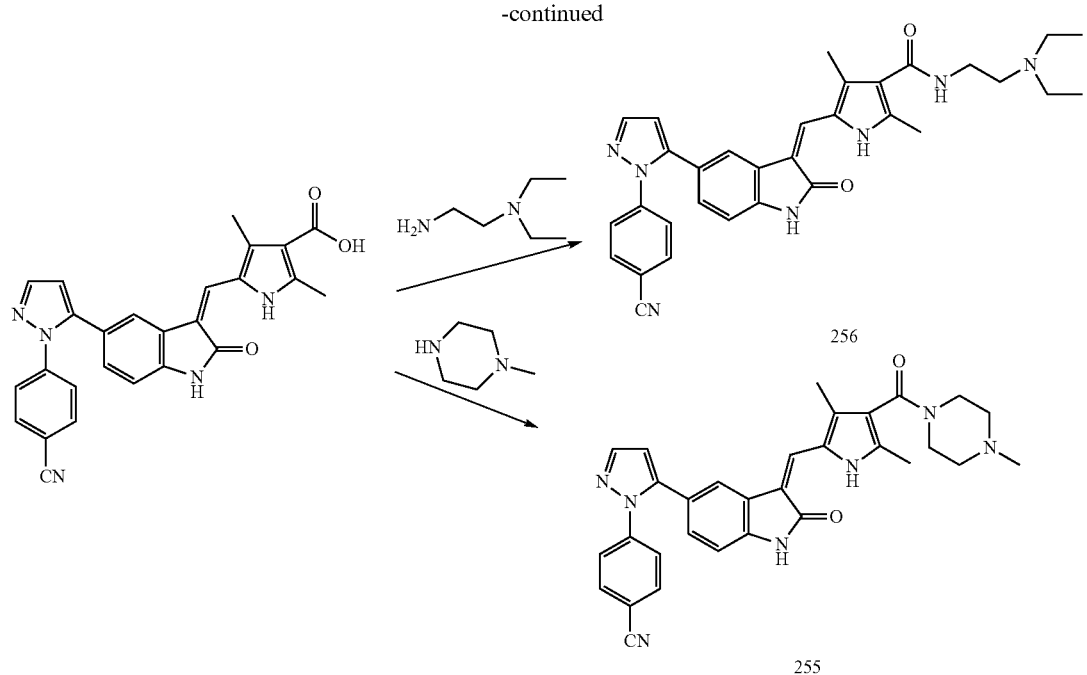
Example 53
Preparation of Compound 257 and 258
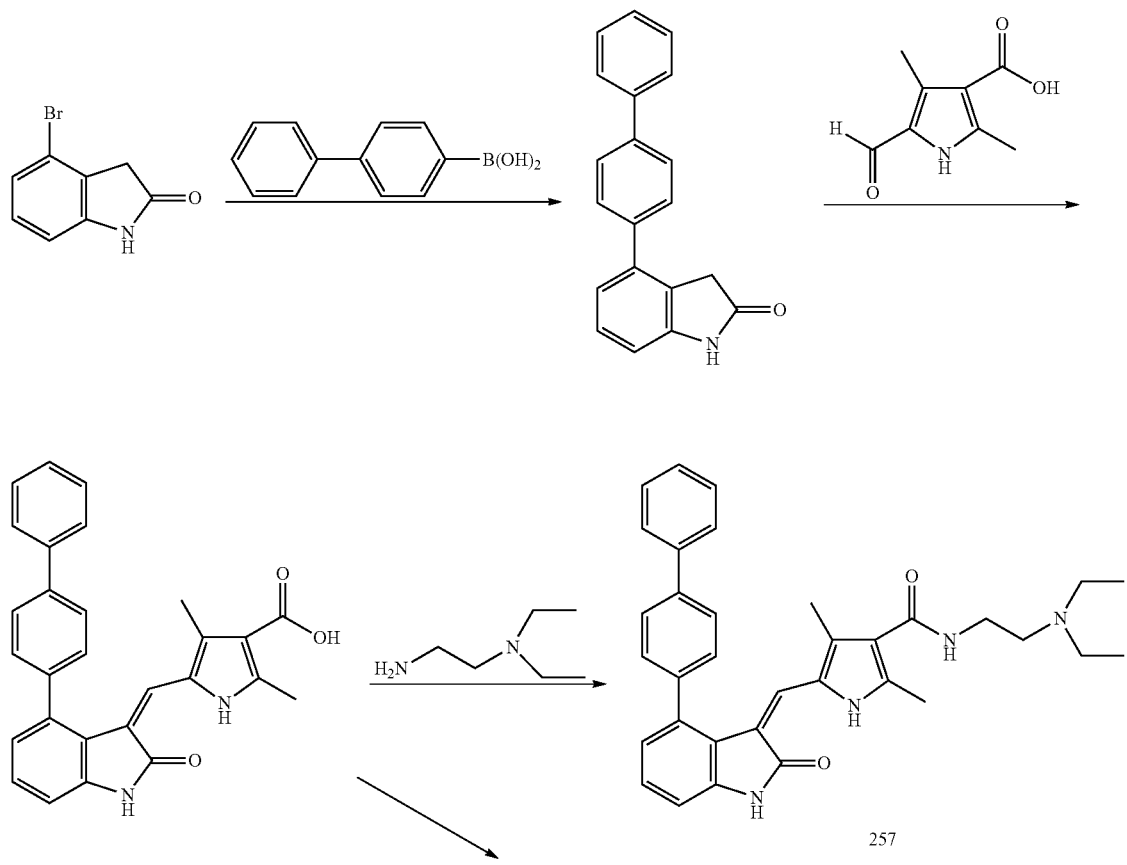

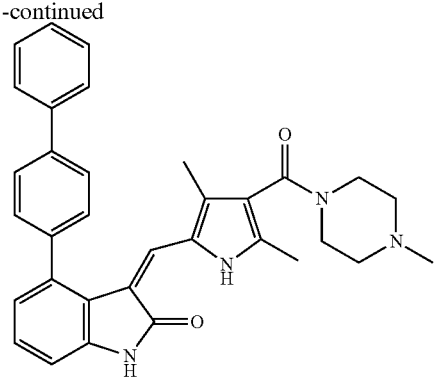
258
Example 54
Preparation of Compound 259 and 260
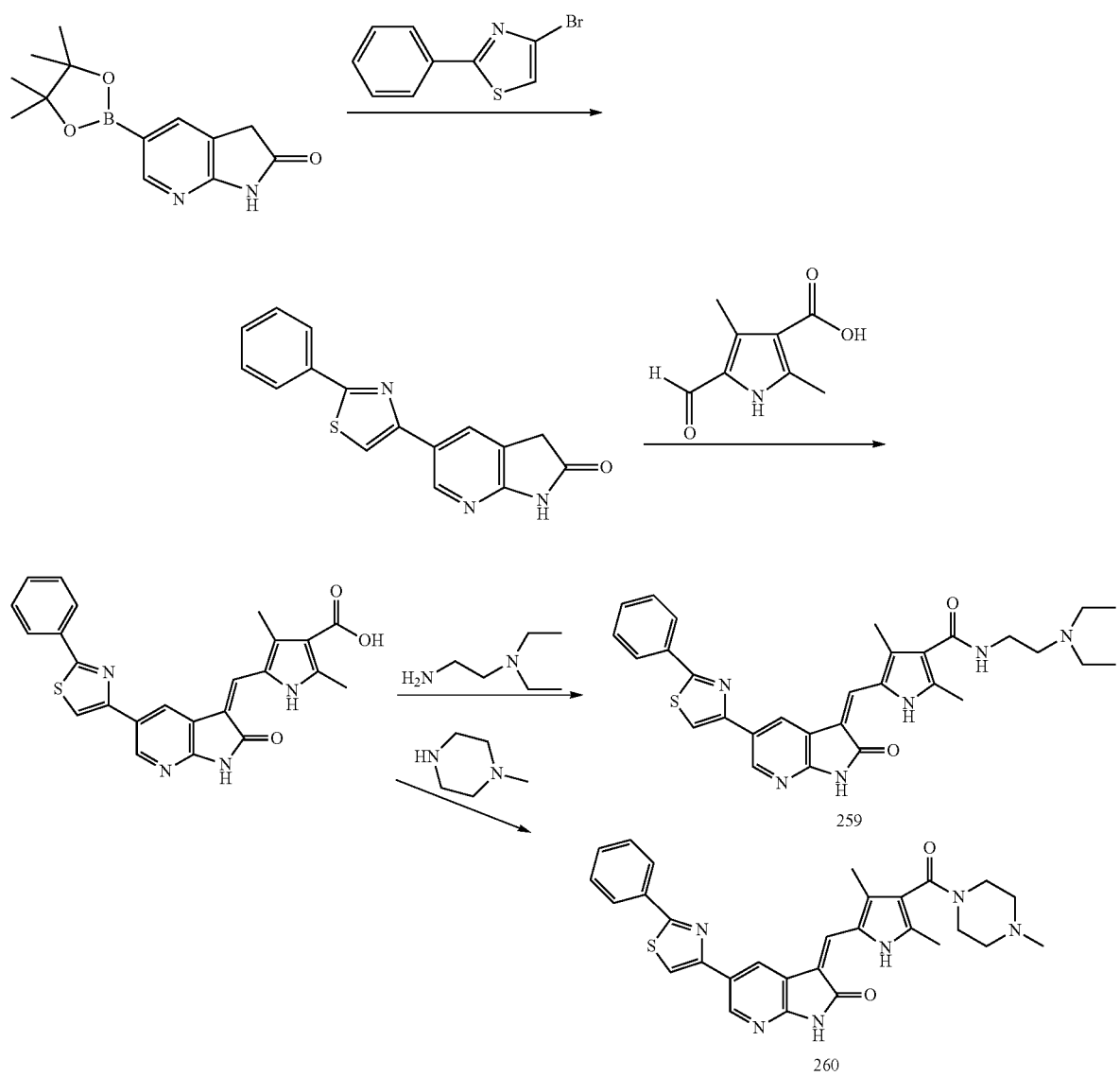
259
260

Example 55
Preparation of Compound 261 and 262
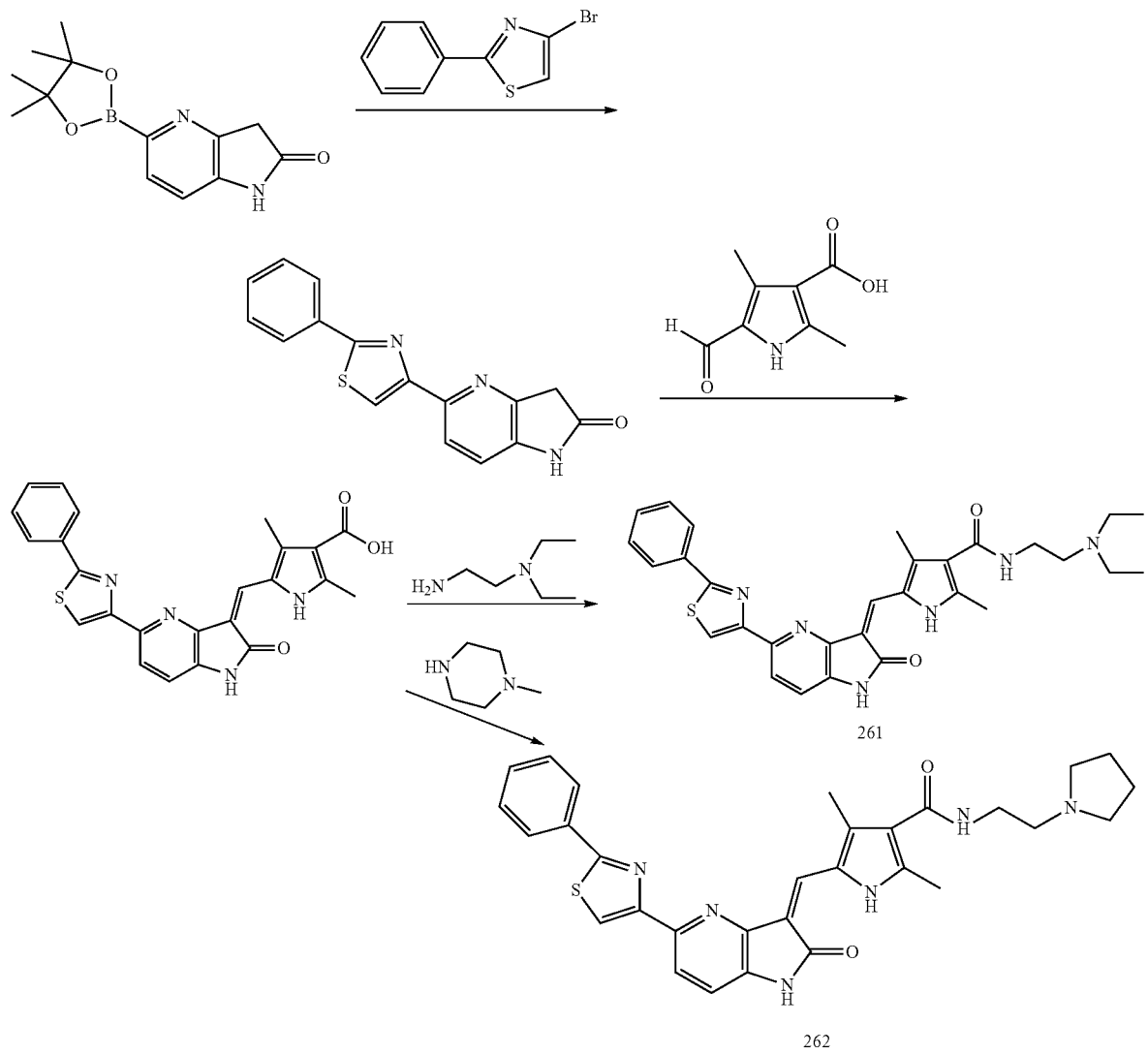
Example 56
Preparation of Compound 263, 264 and 265
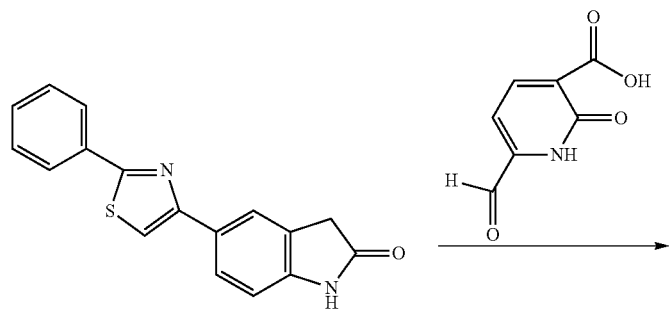

111
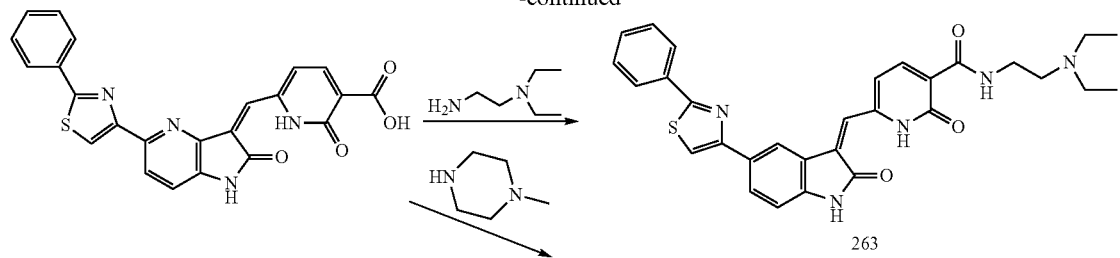
112
-continued
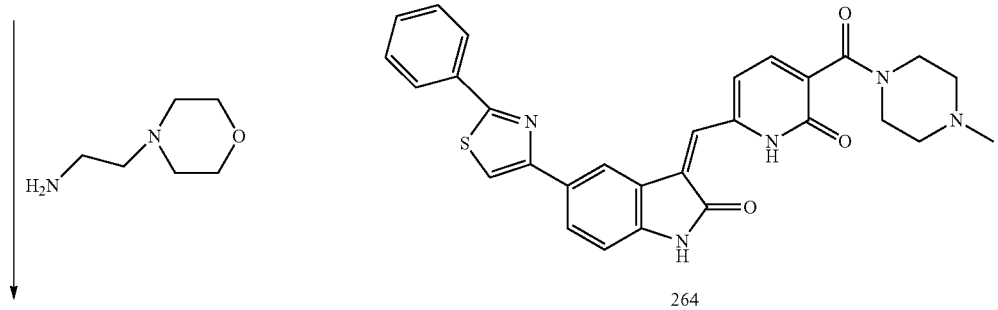
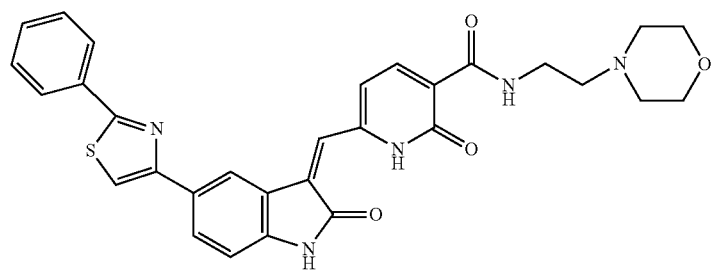
265
Example 57
Preparation of Compound 268
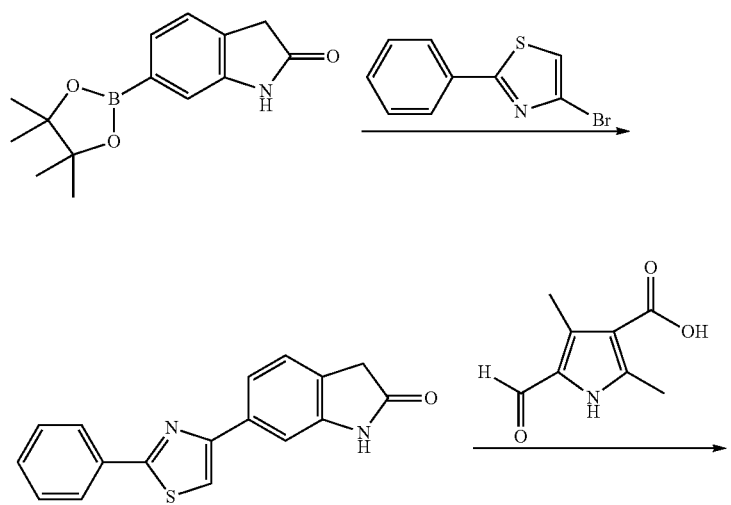

-continued
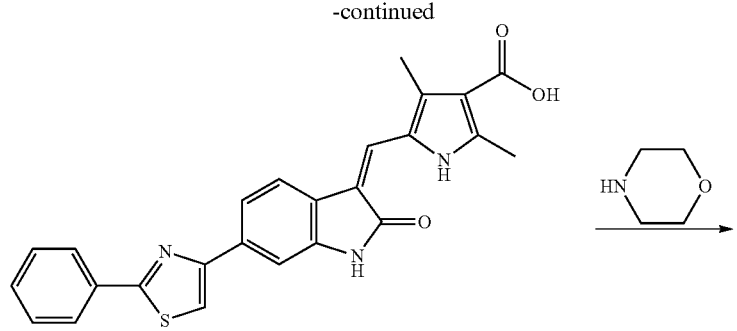
268
Example 58
Preparation of Compound 273
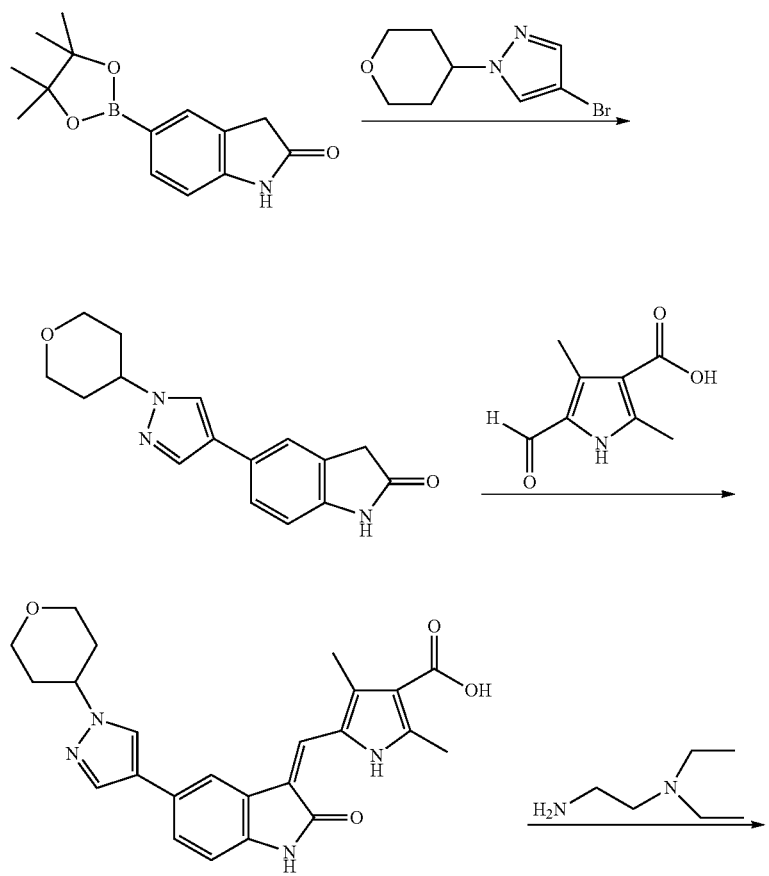

-continued
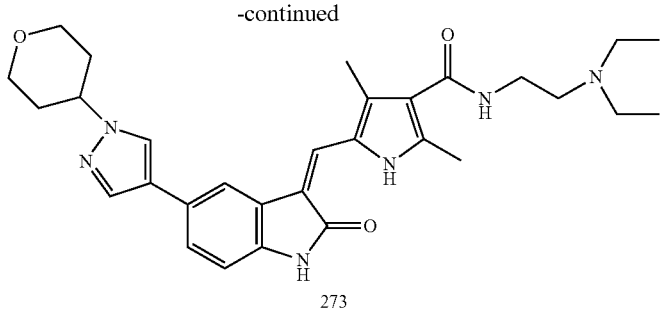
273
Example 59
Preparation of Compound 274, 276 and 275
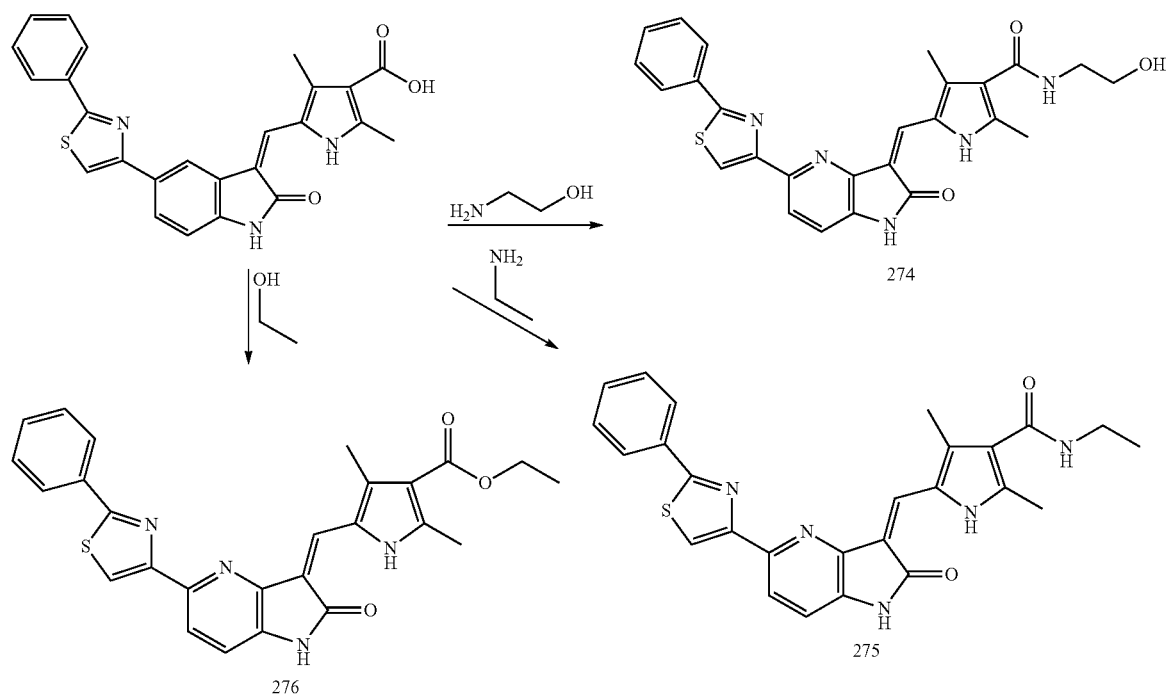
Example 60
Preparation of Compound 277
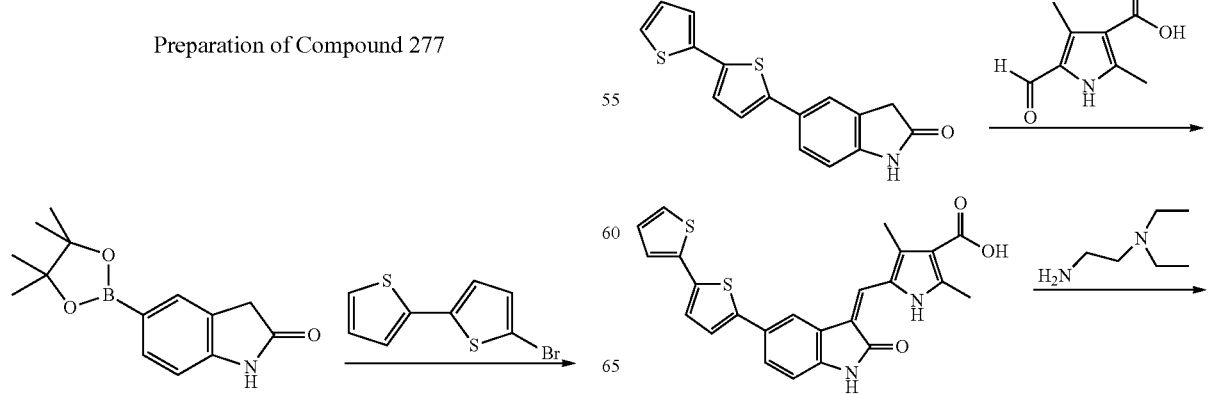

117
-continued
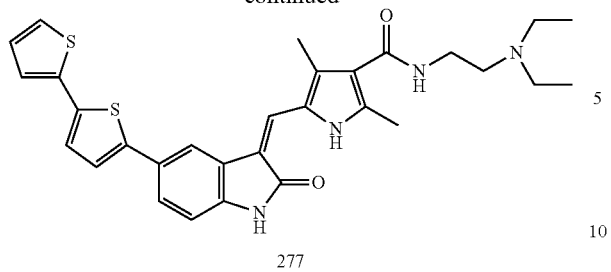
277
Example 61
Preparation of Compound 278, 281, and 280
118
Example 62
Preparation of Compound 279
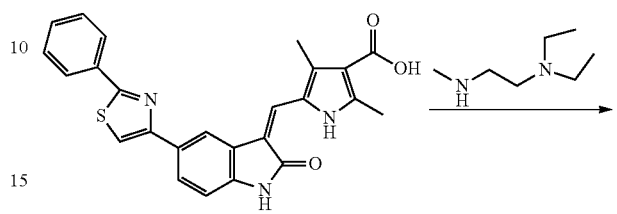
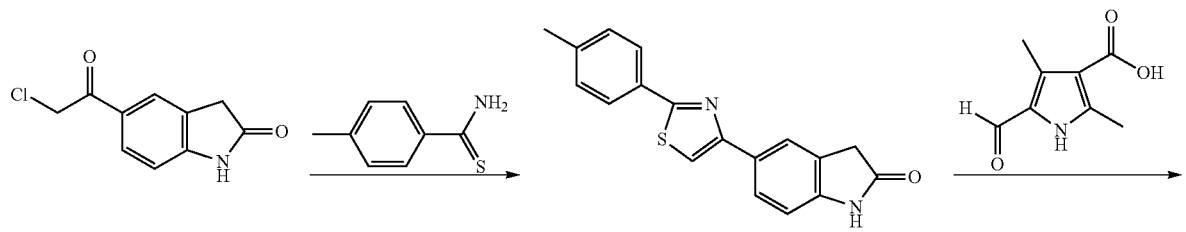
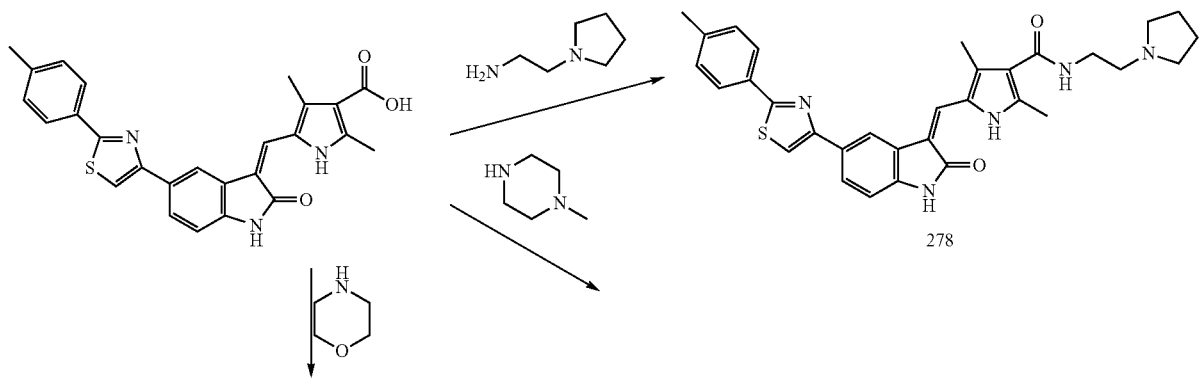
278
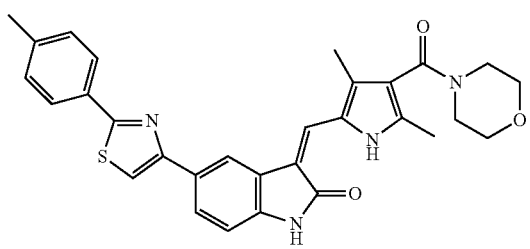
281
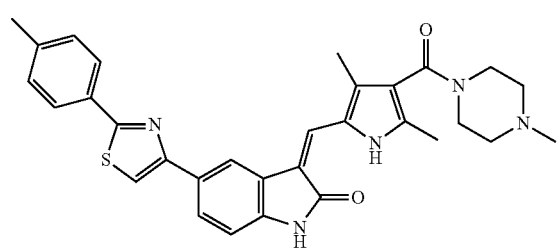
280

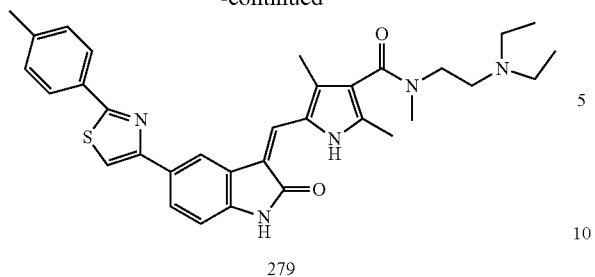
279
Example 63
Preparation of Compound 282
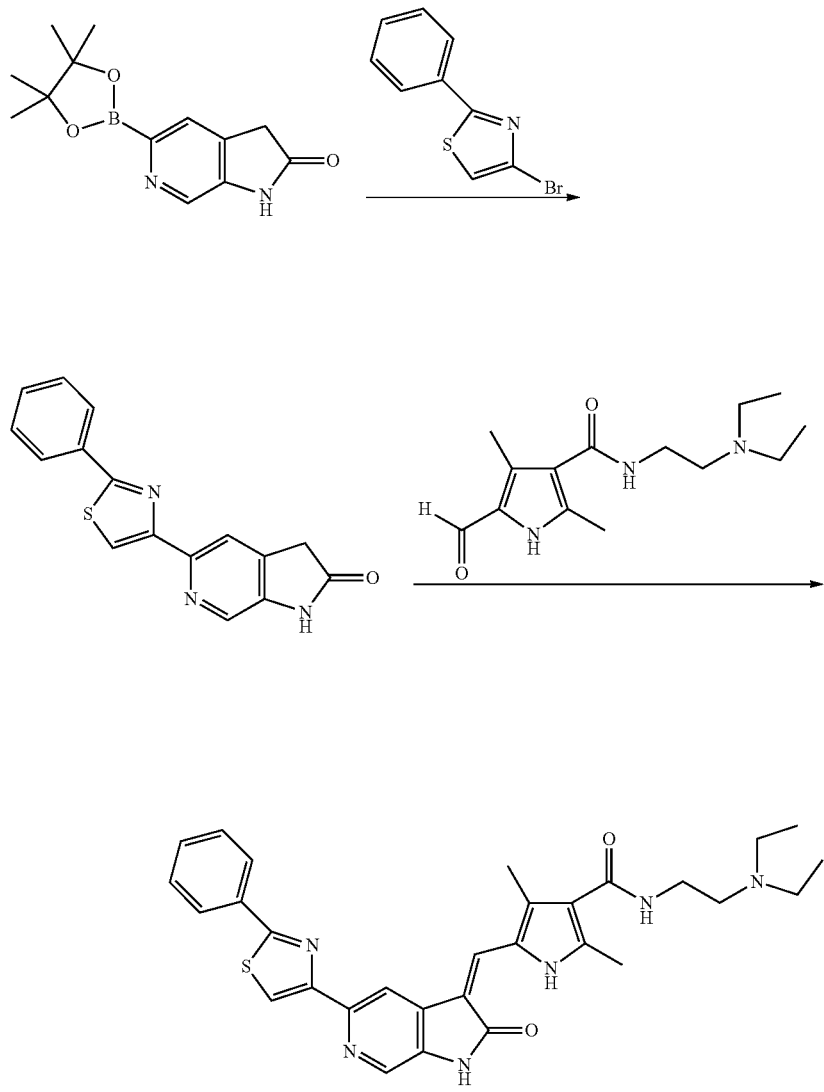
282

Example 64
Preparation of Compound 283
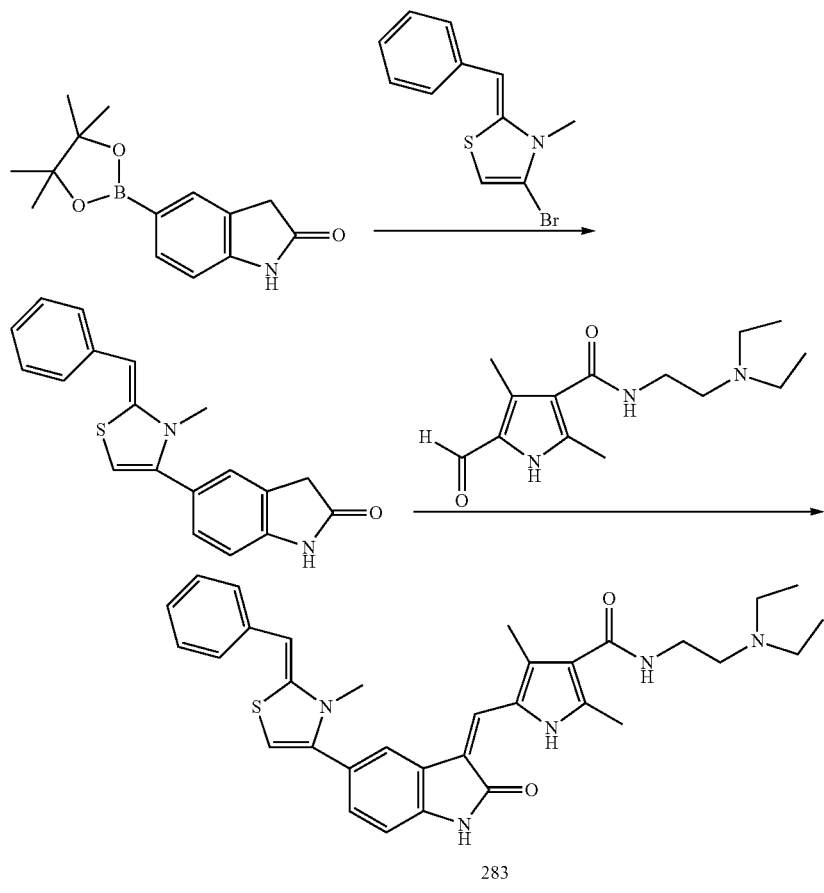
Example 65
Preparation of Compound 284
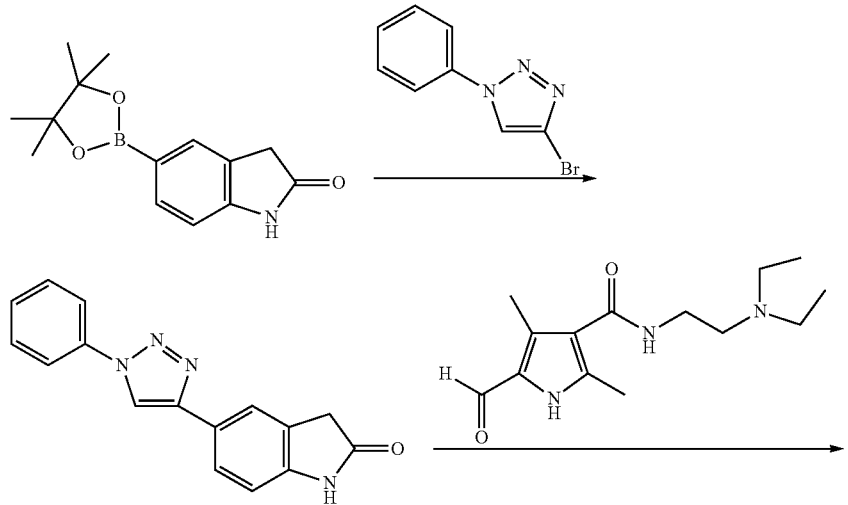

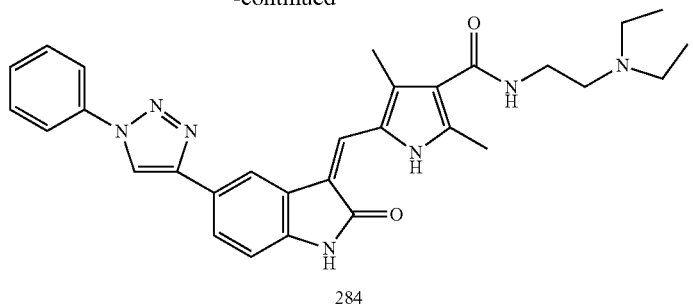
284
Example 66
Preparation of Compound 285
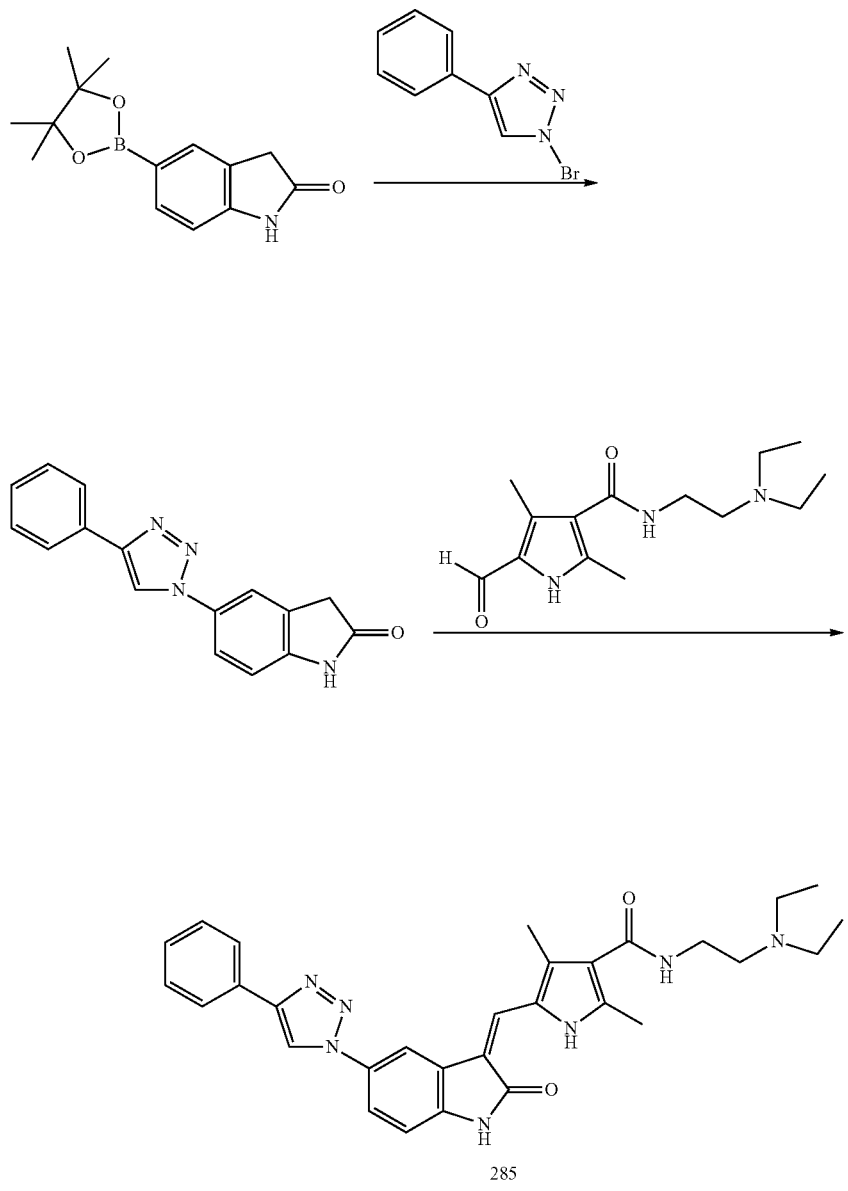
285

Example 67
Preparation of Compound 287 and 286
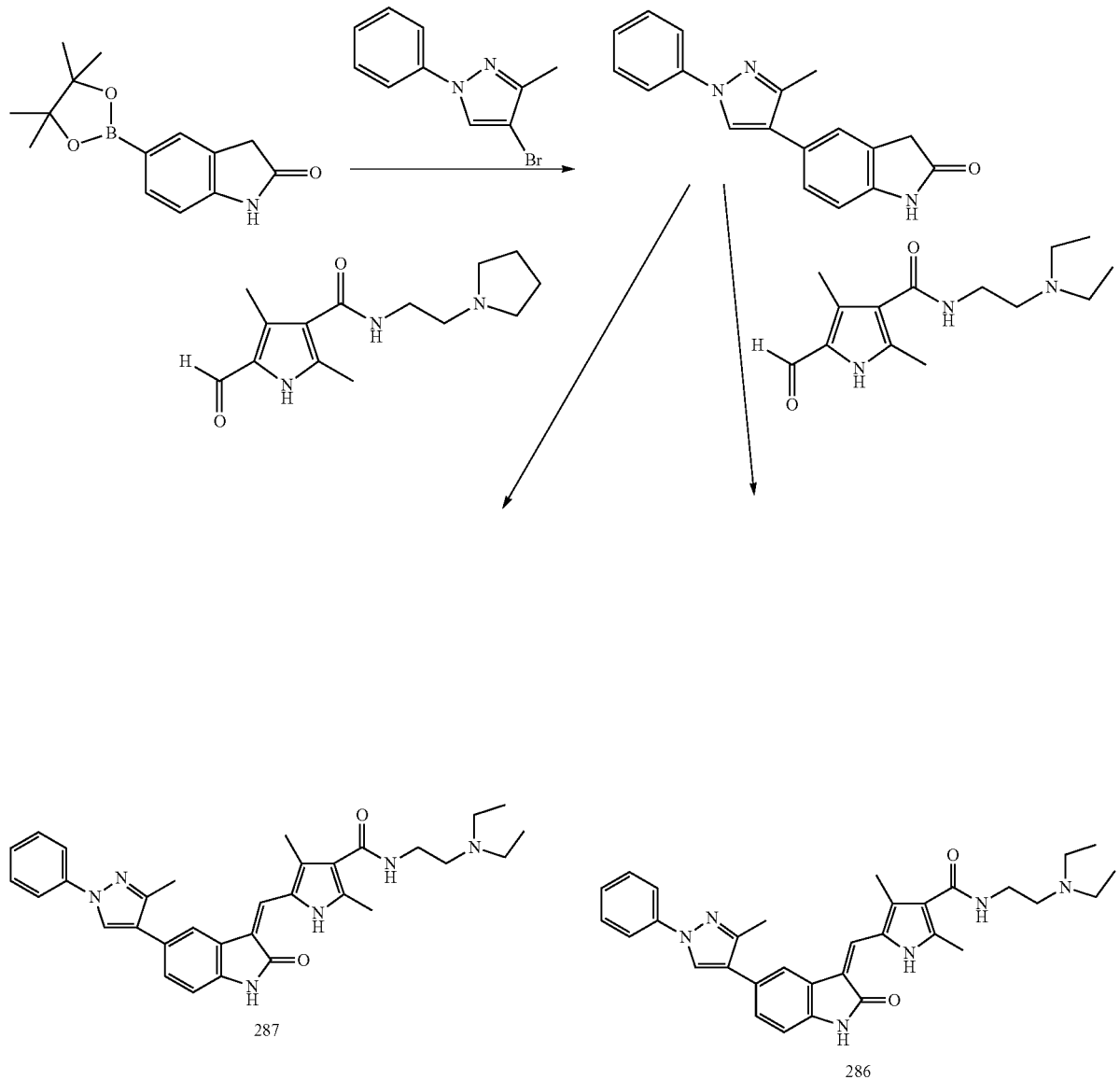
Example 68
Preparation of Compound 288
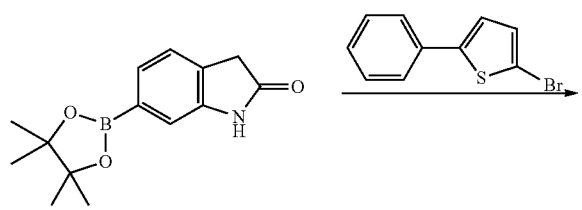

-continued
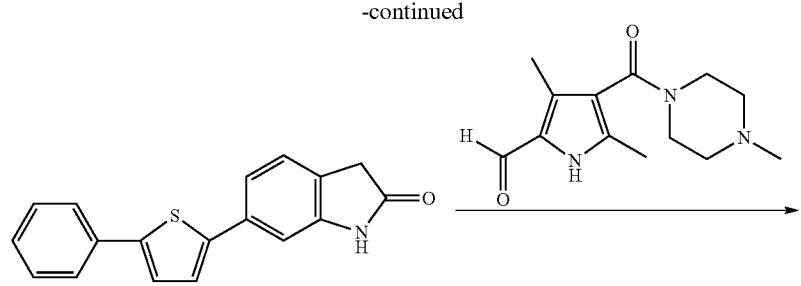
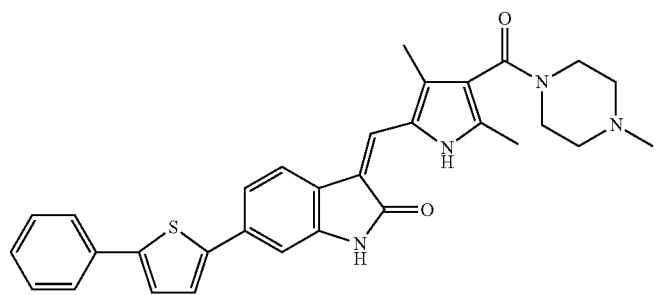
288
Example 69
Preparation of Compound 293, 289, and 290
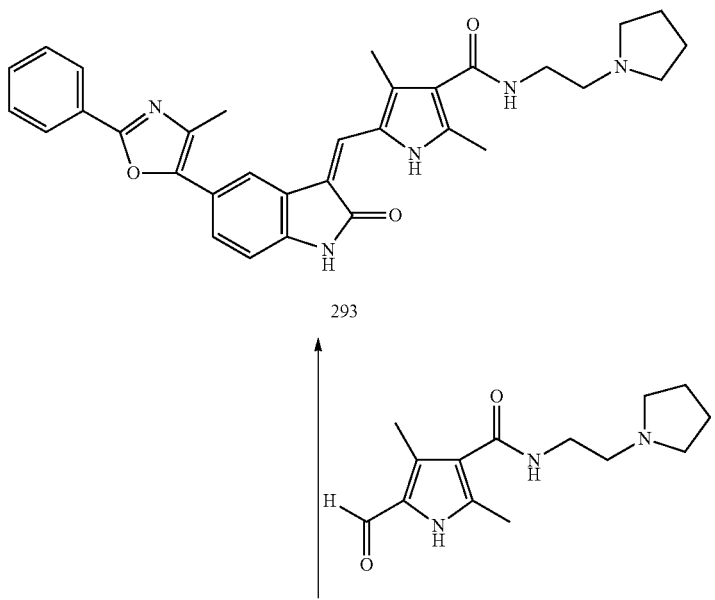

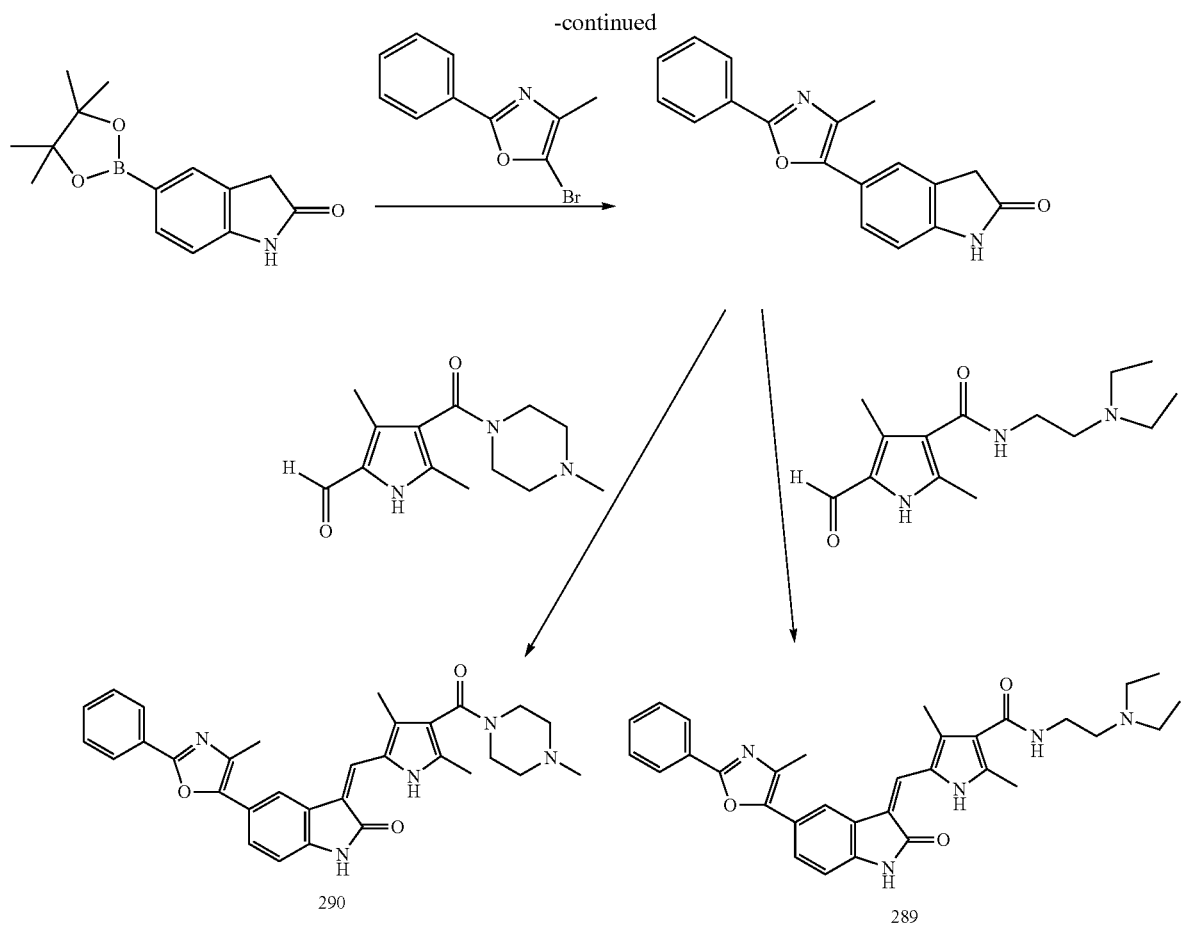
Example 70
Preparation of Compound 292 and 291
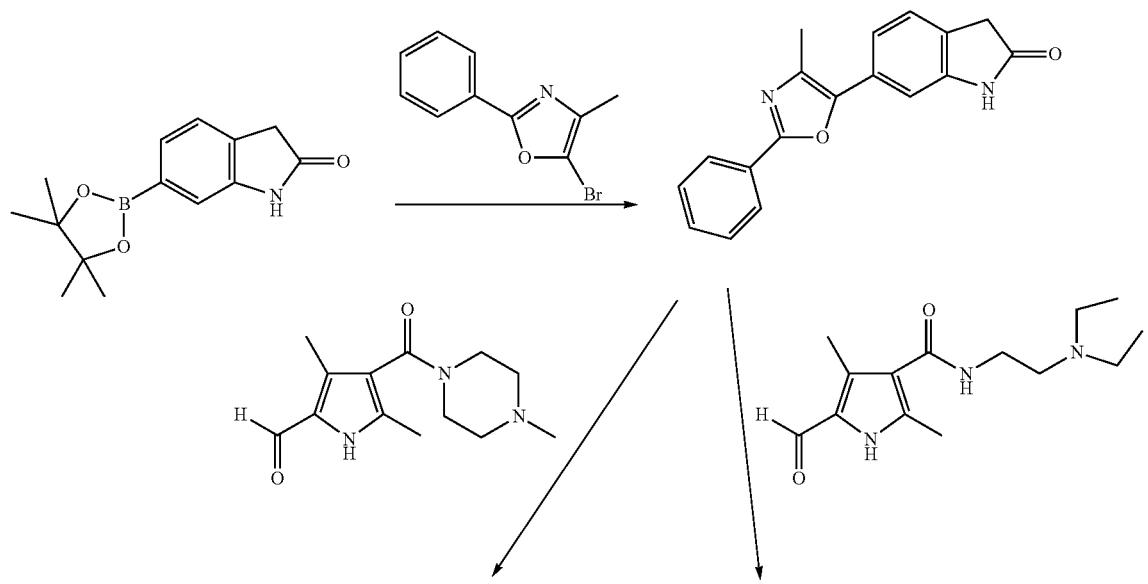

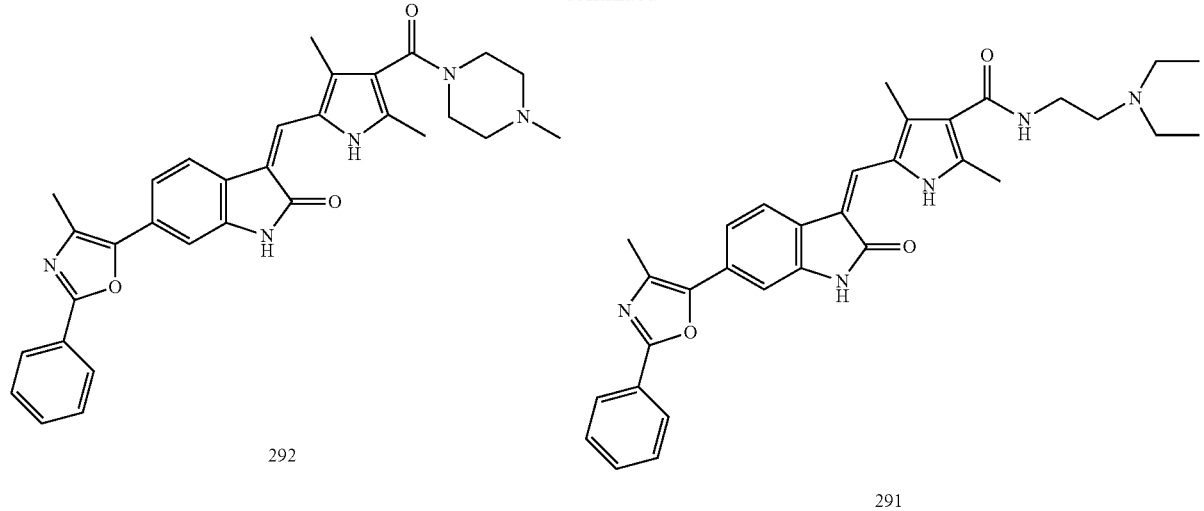
292
291
Example 71
Preparation of Compound 295 and 294
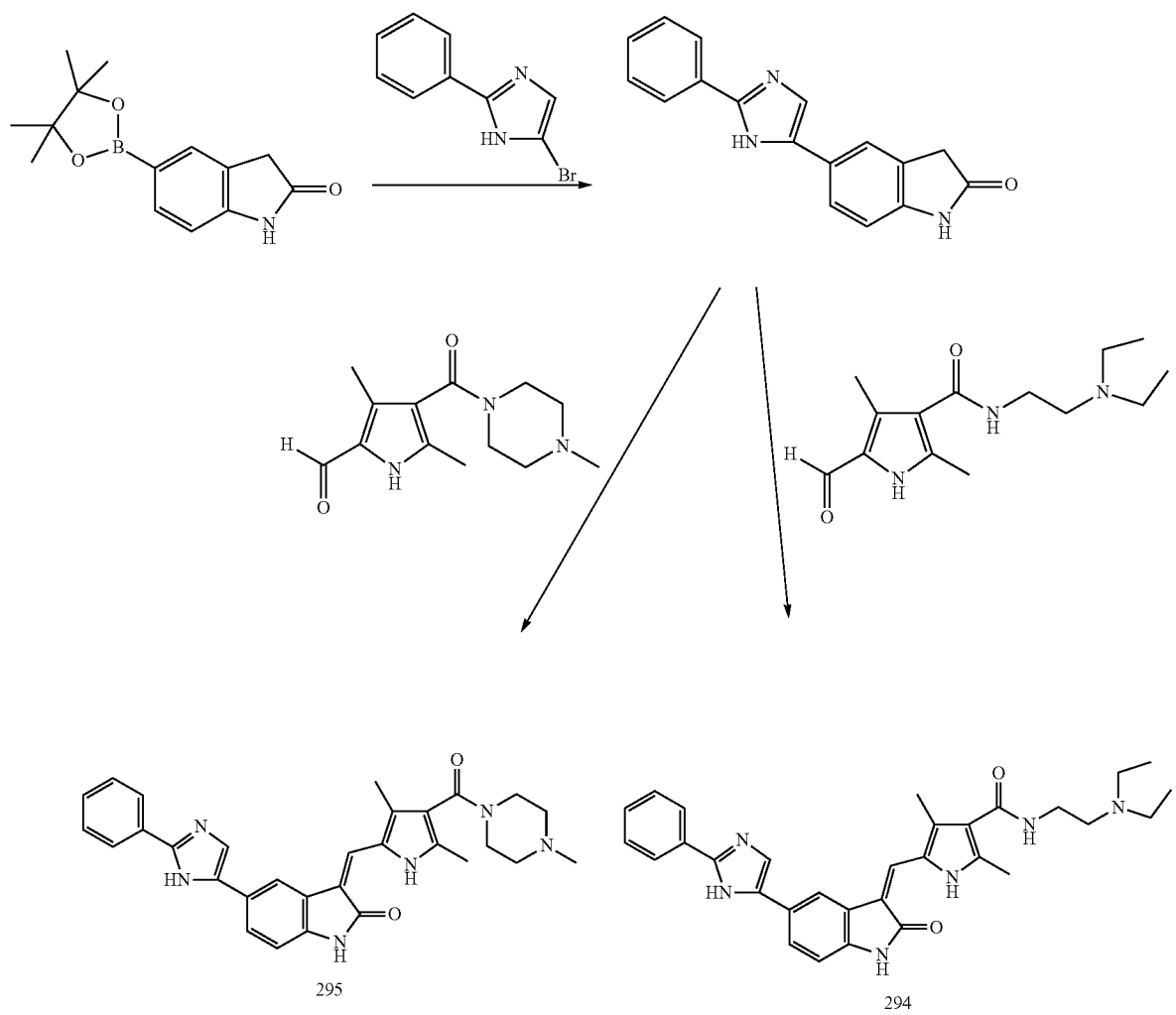
295
294

Example 72
Preparation of Compound 296
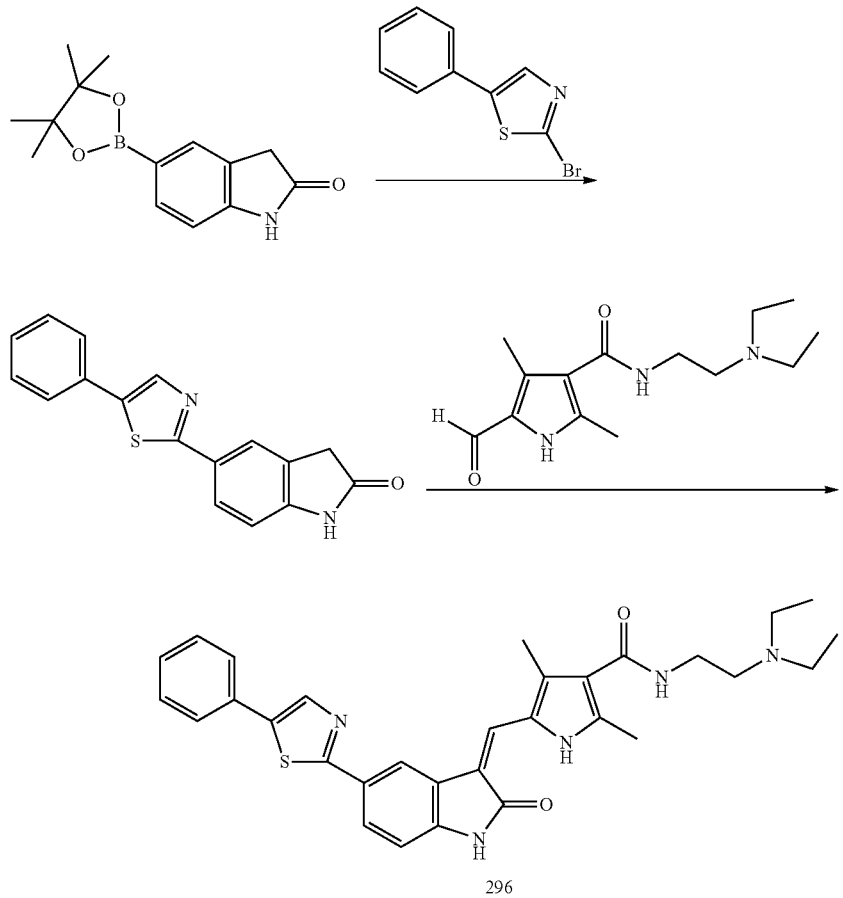
Example 73
Preparation of Compound 297
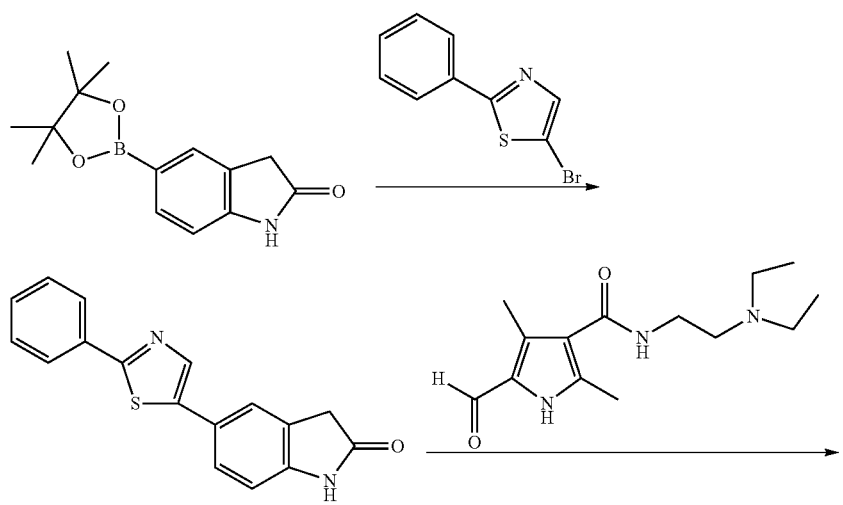

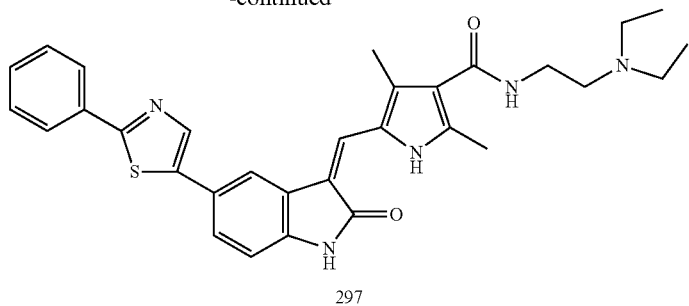
297
Example 74
Preparation of Compound 298
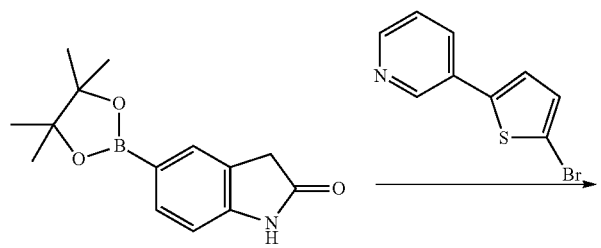
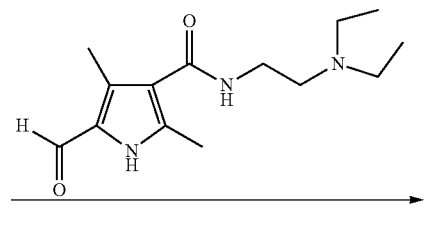
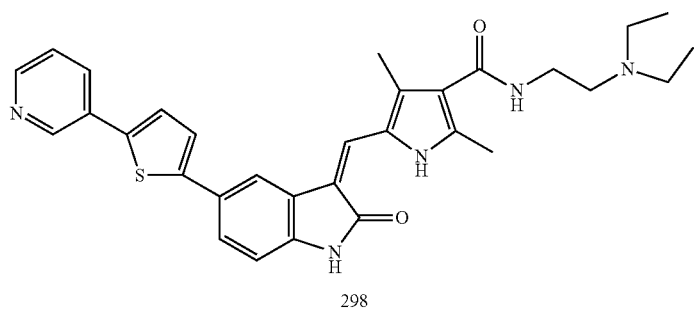
298

Example 75
Preparation of Compound 302, 301, 300 and 299
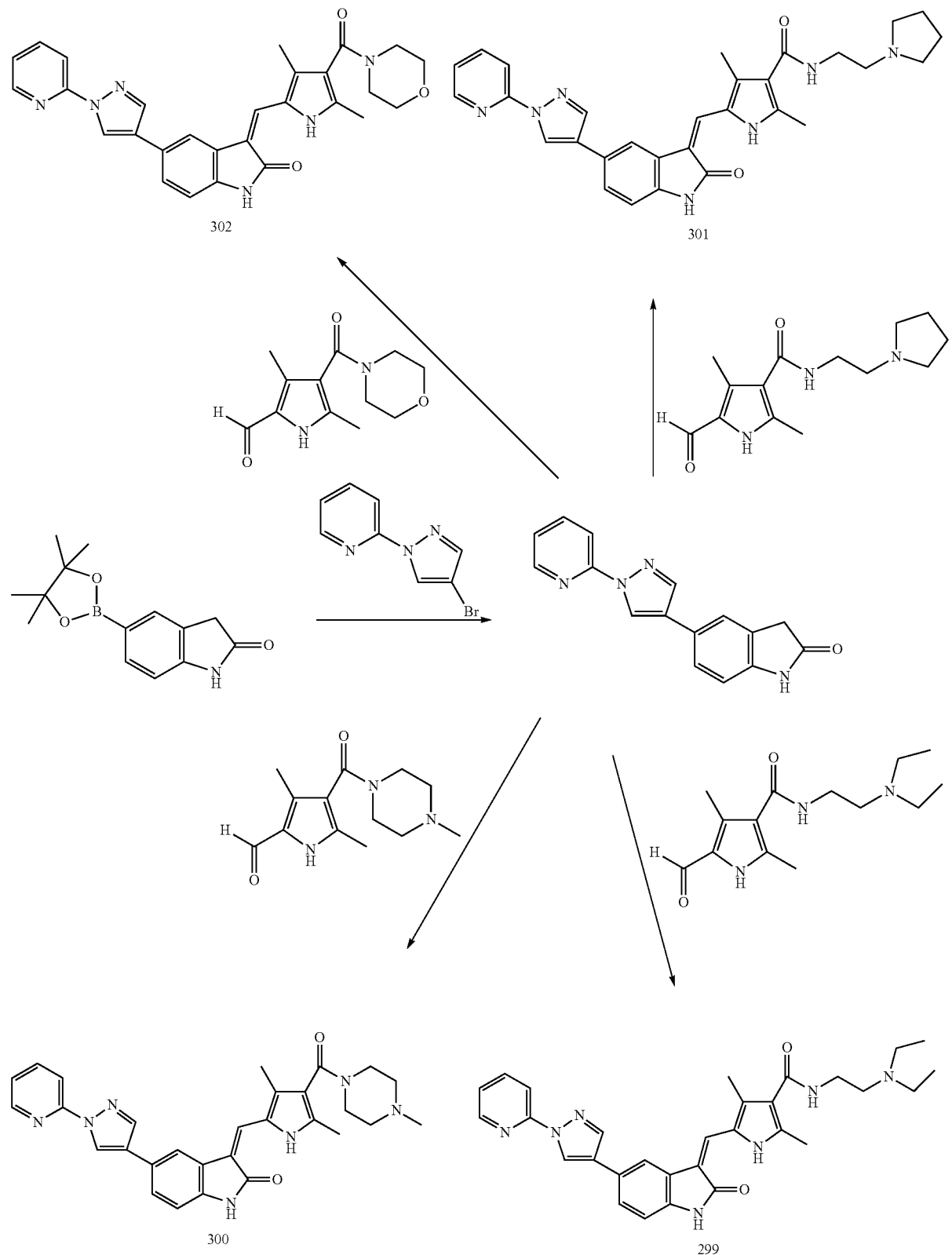

Example 76
Preparation of Compound 303
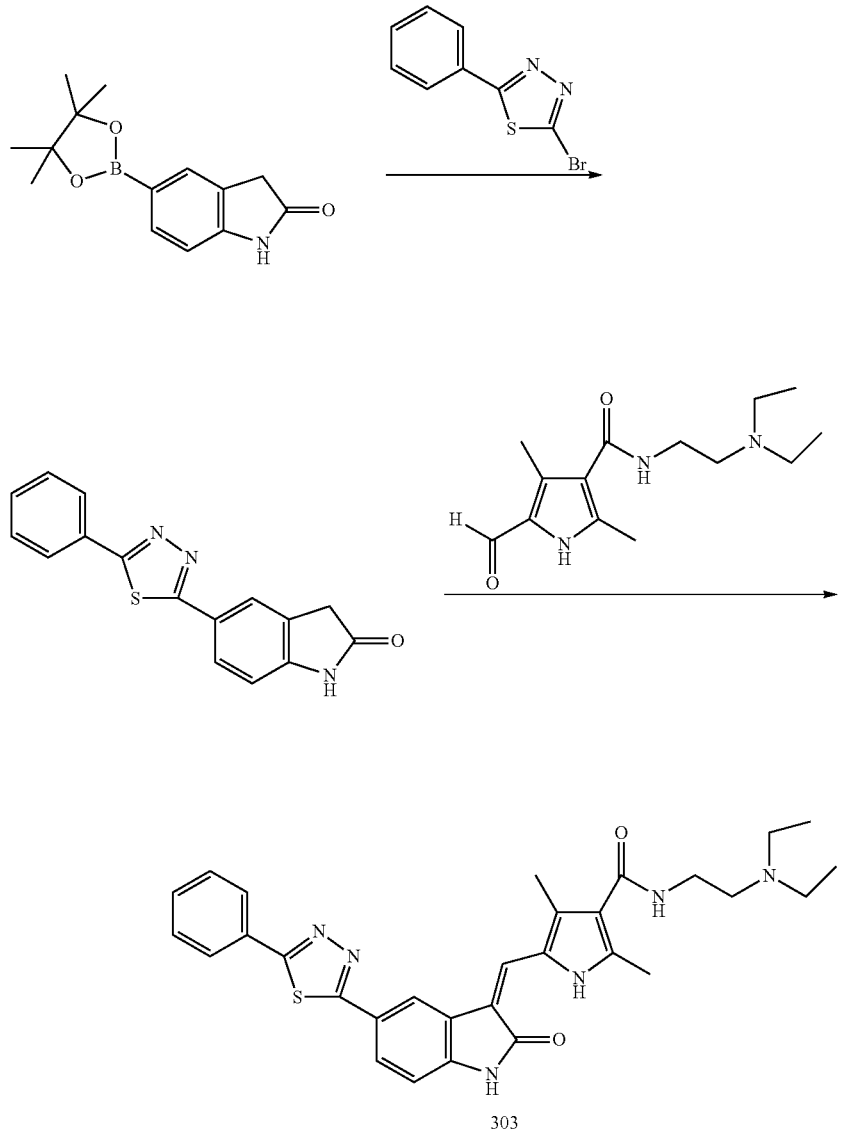
Example 77
Preparation of Compound 304
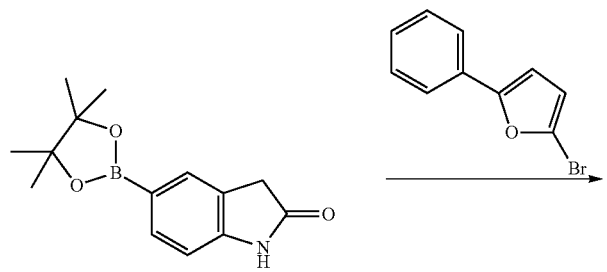

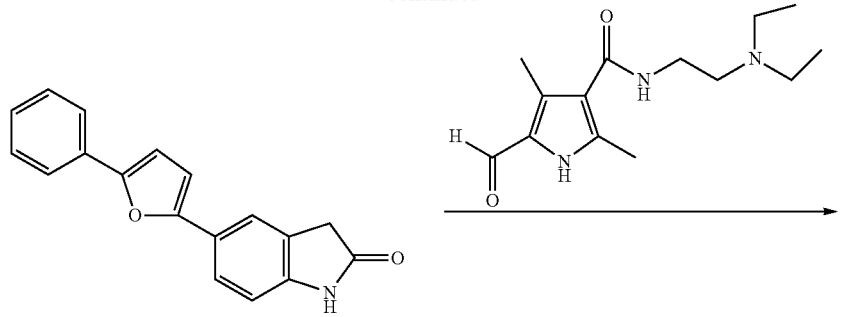
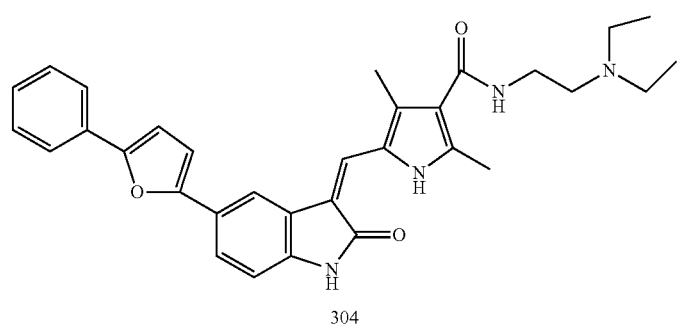
304
Example 78
Preparation of Compound 305
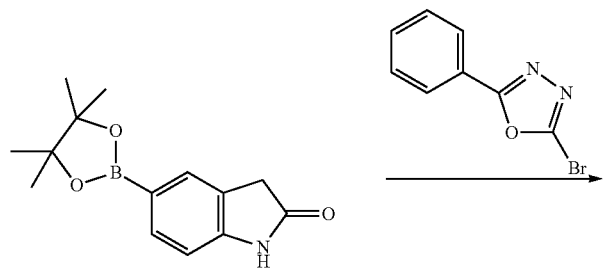
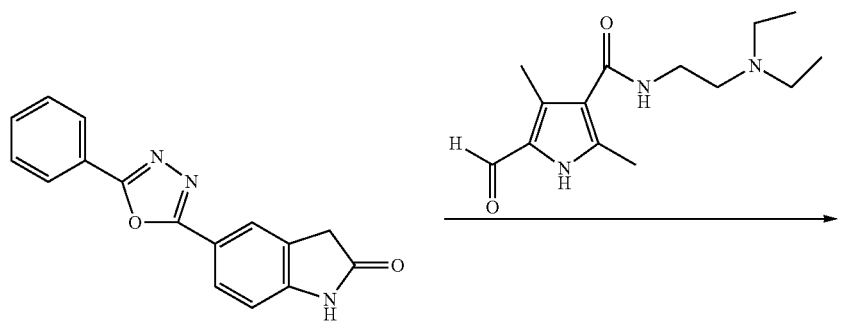

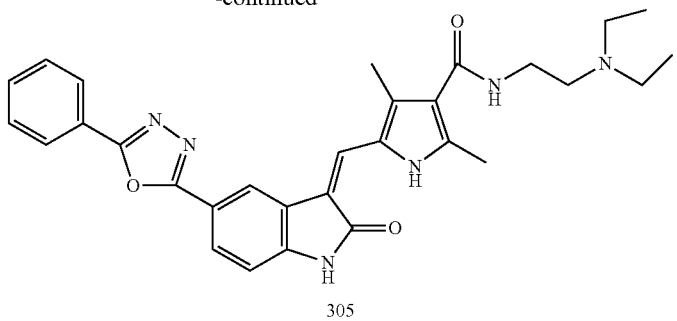
305
Example 79
Preparation of Compound 306
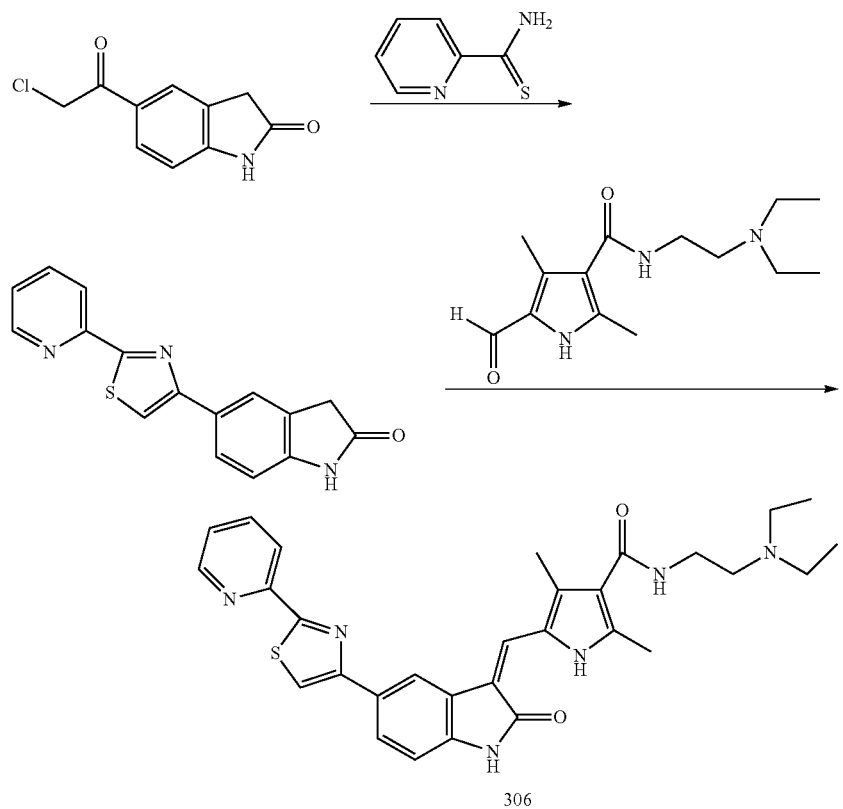
306
Example 80
Preparation of Compound 307
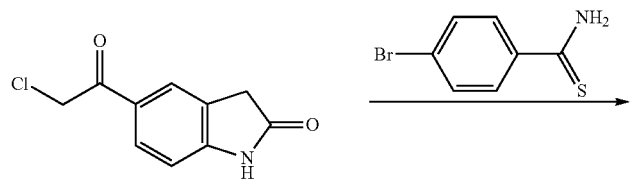

-continued
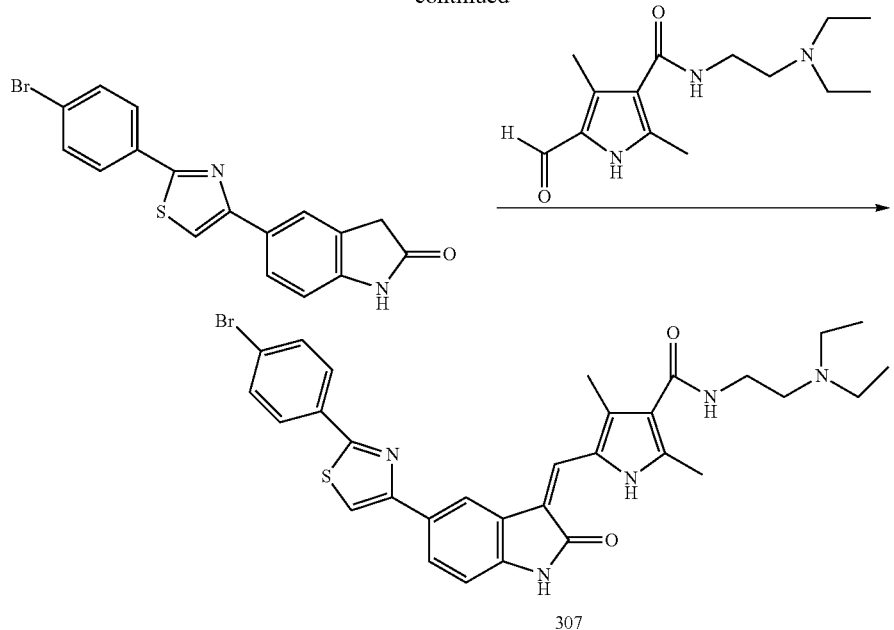
307
Example 81
Preparation of Compound 308
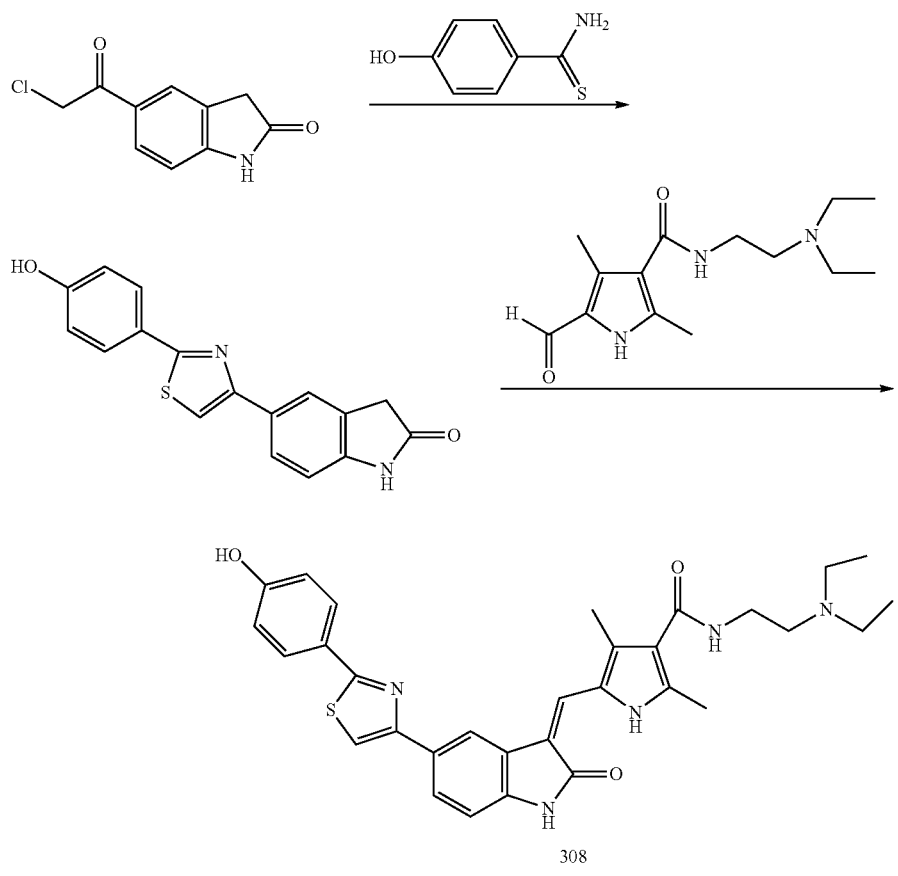
308

147
Example 82
Preparation of Compound 309
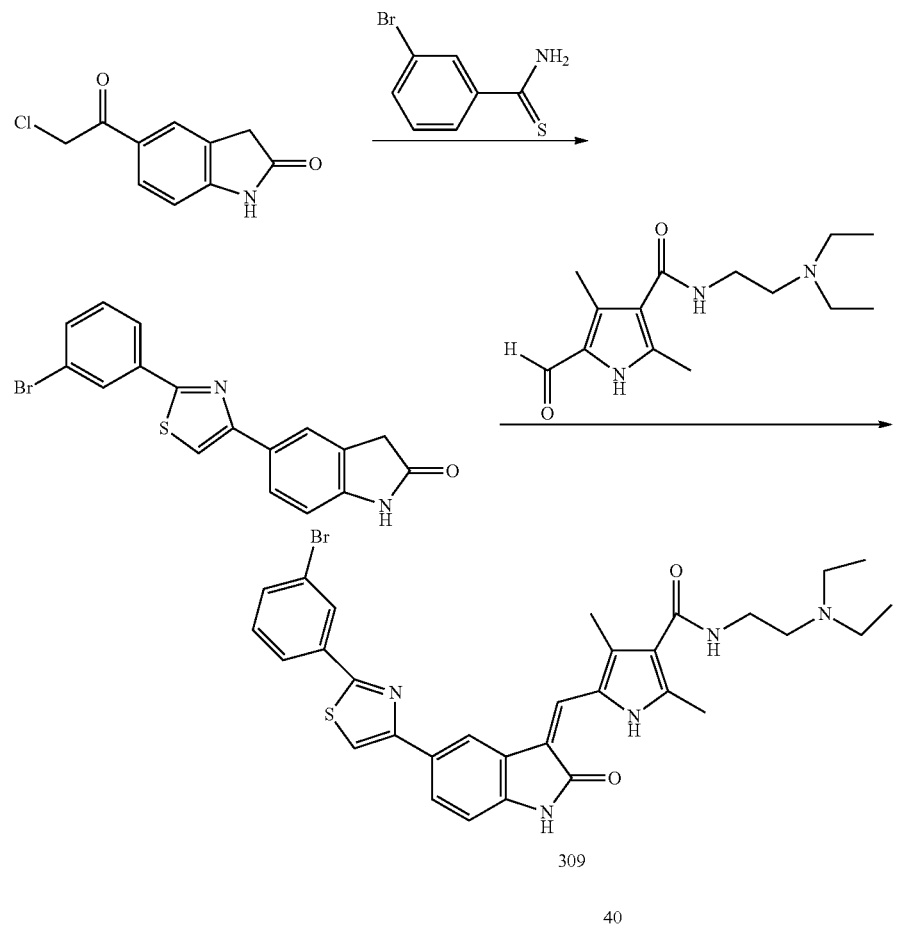
309
Example 83
Preparation of Compound 310
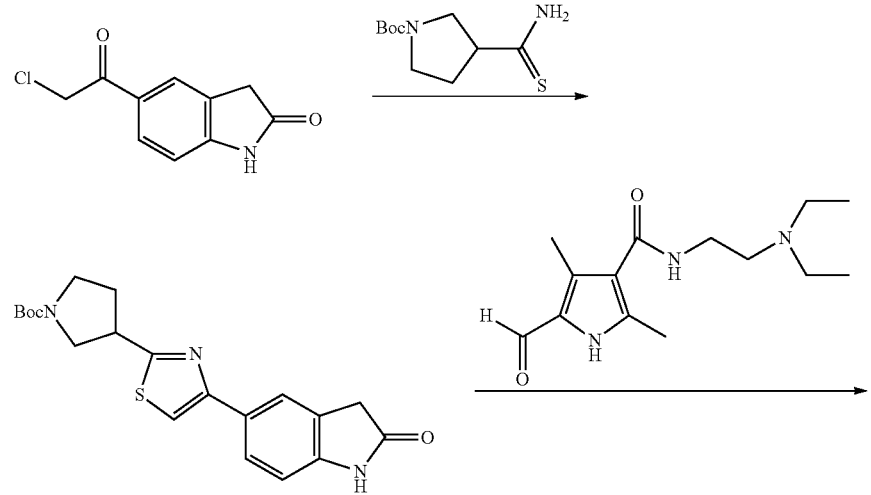

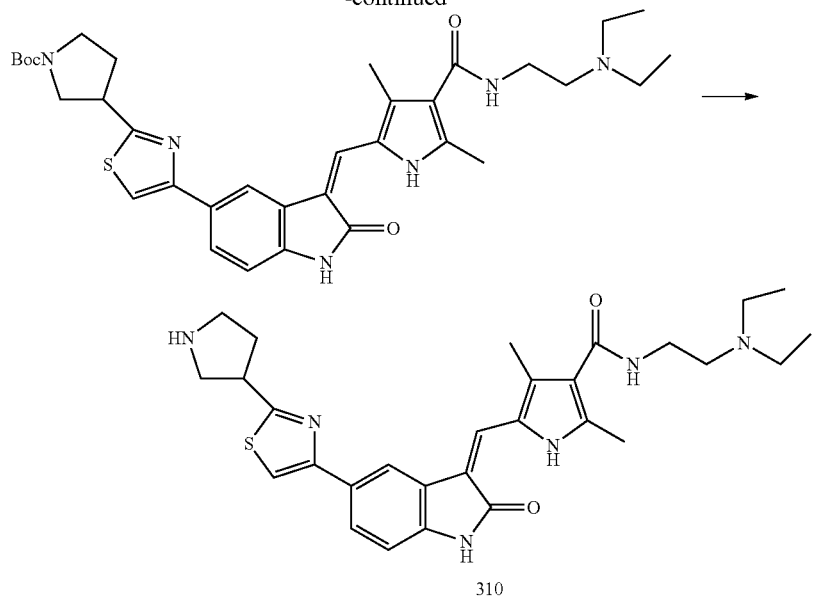
Example 84
Preparation of Compound 311
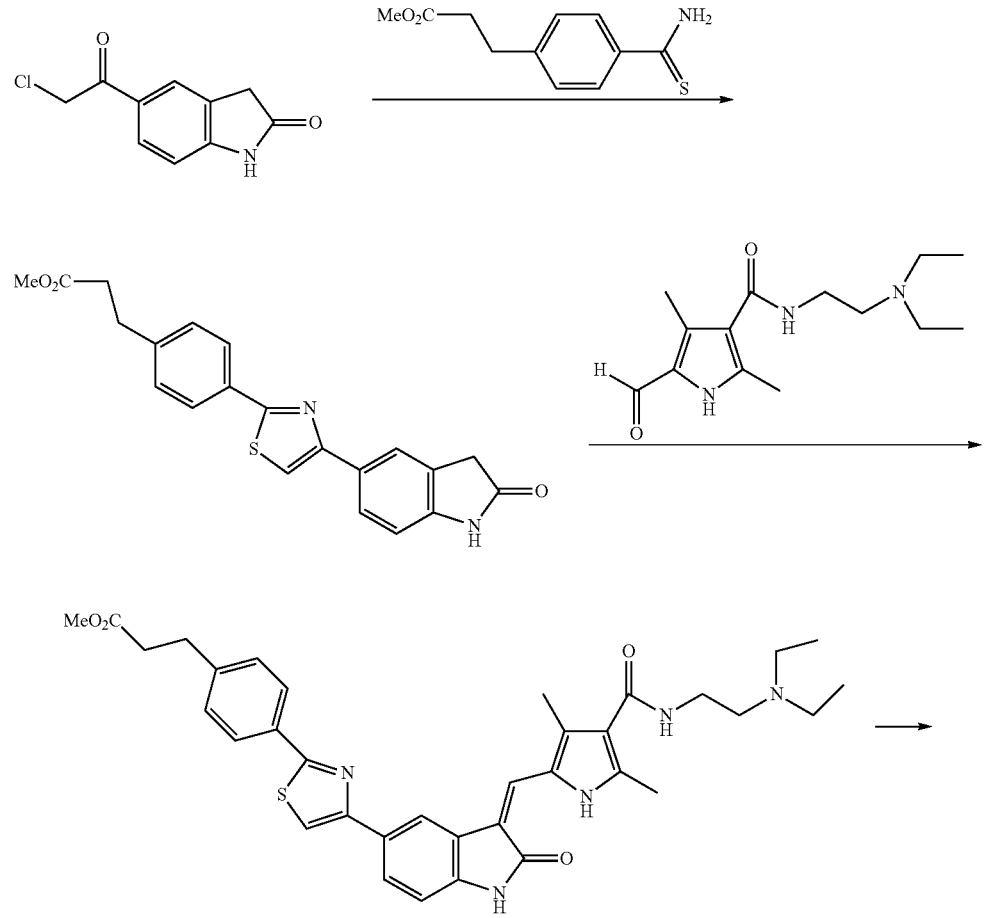

151
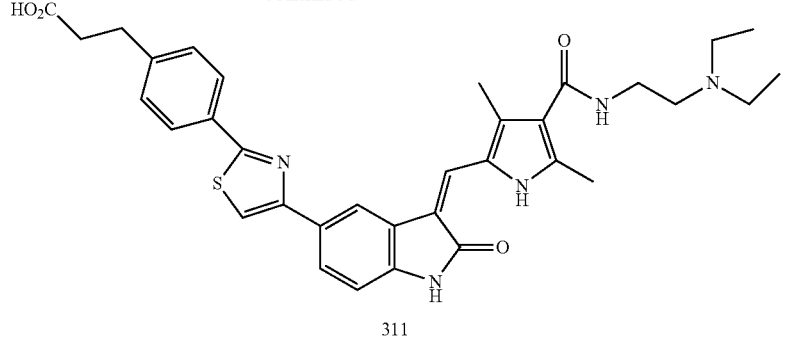
311
Example 85
Preparation of Compound 312
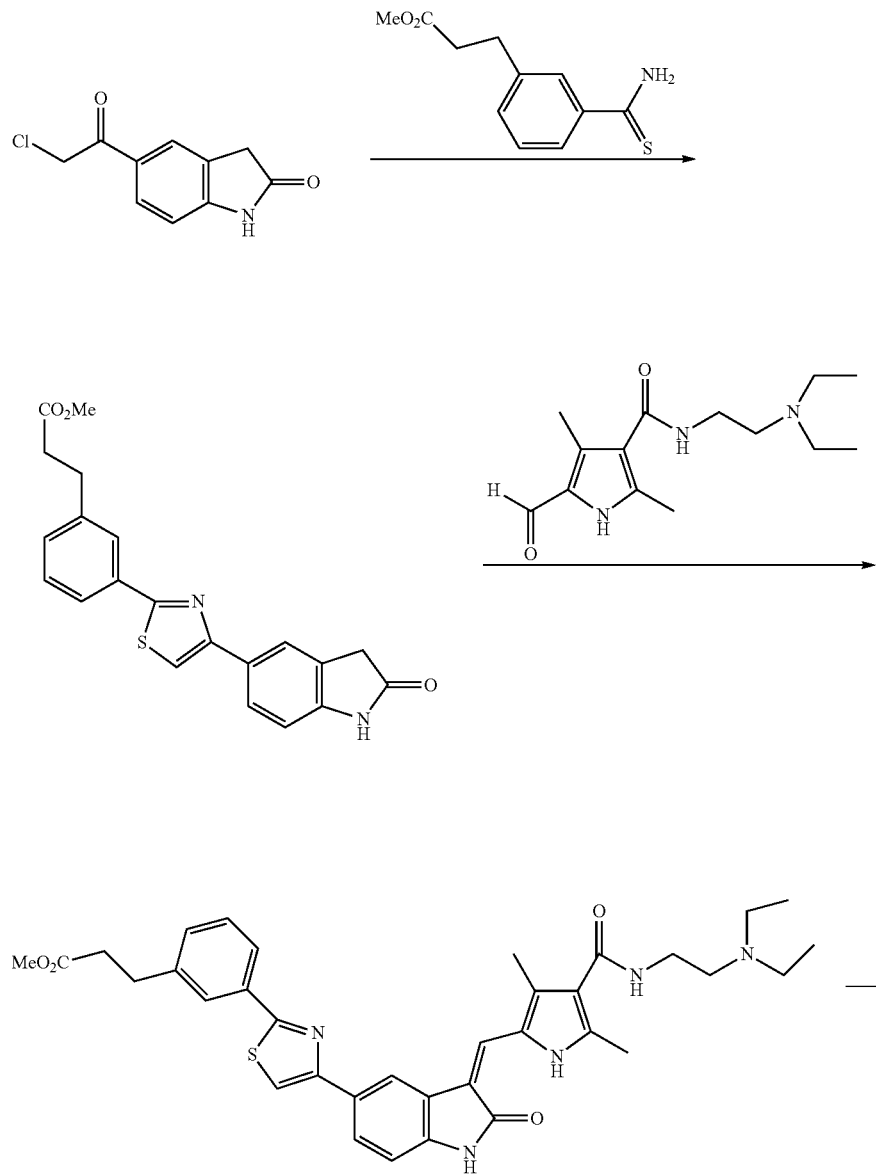

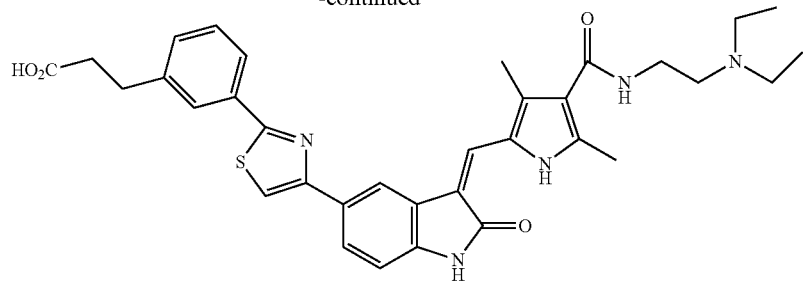
312
Example 86
Preparation of Compound 269 and 237
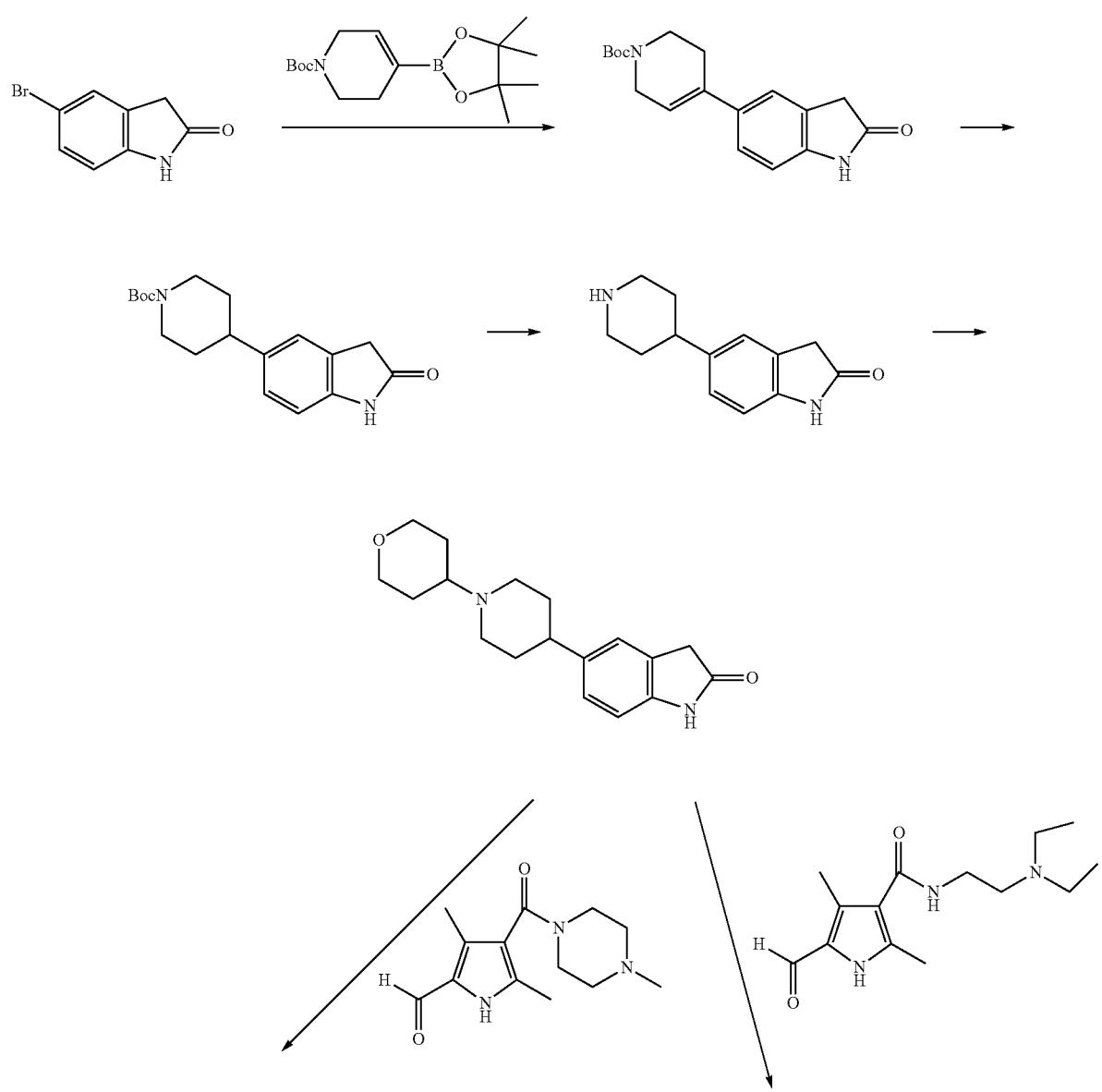

| 155 | 156 |
|---|---|
| 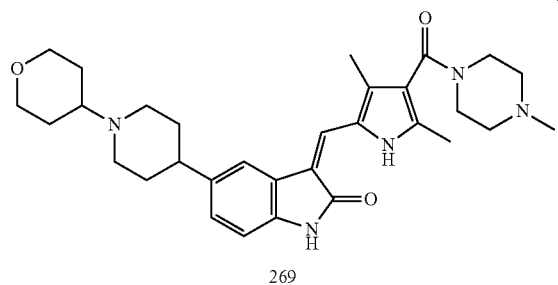 269 | -continued 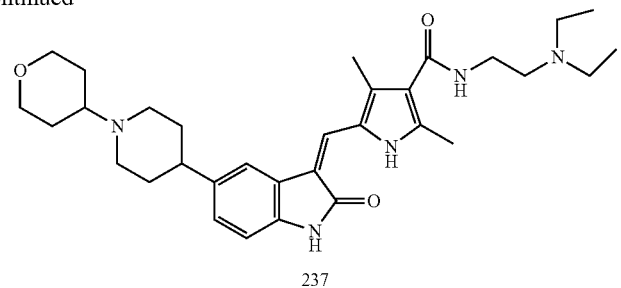 237 |
Example 87
Preparation of Compound 267
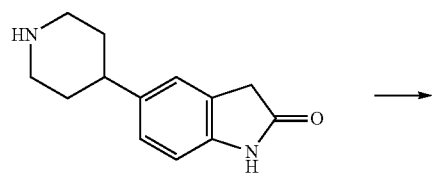
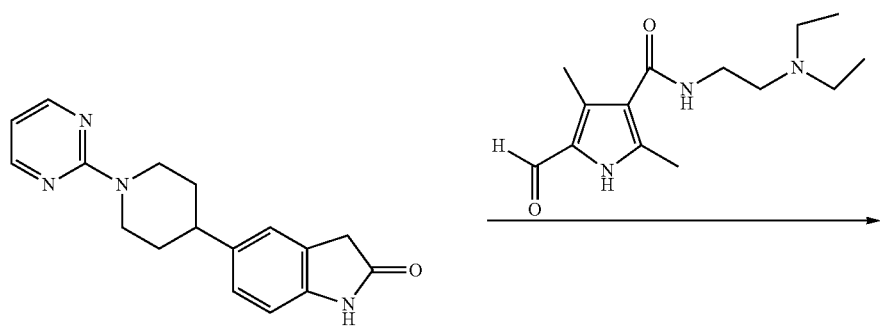
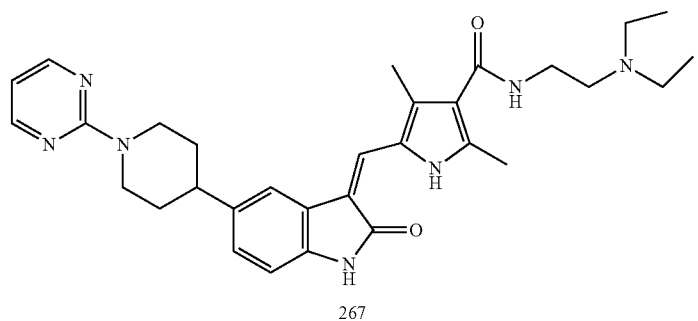
267

Example 88
Preparation of Compound 270 and 272
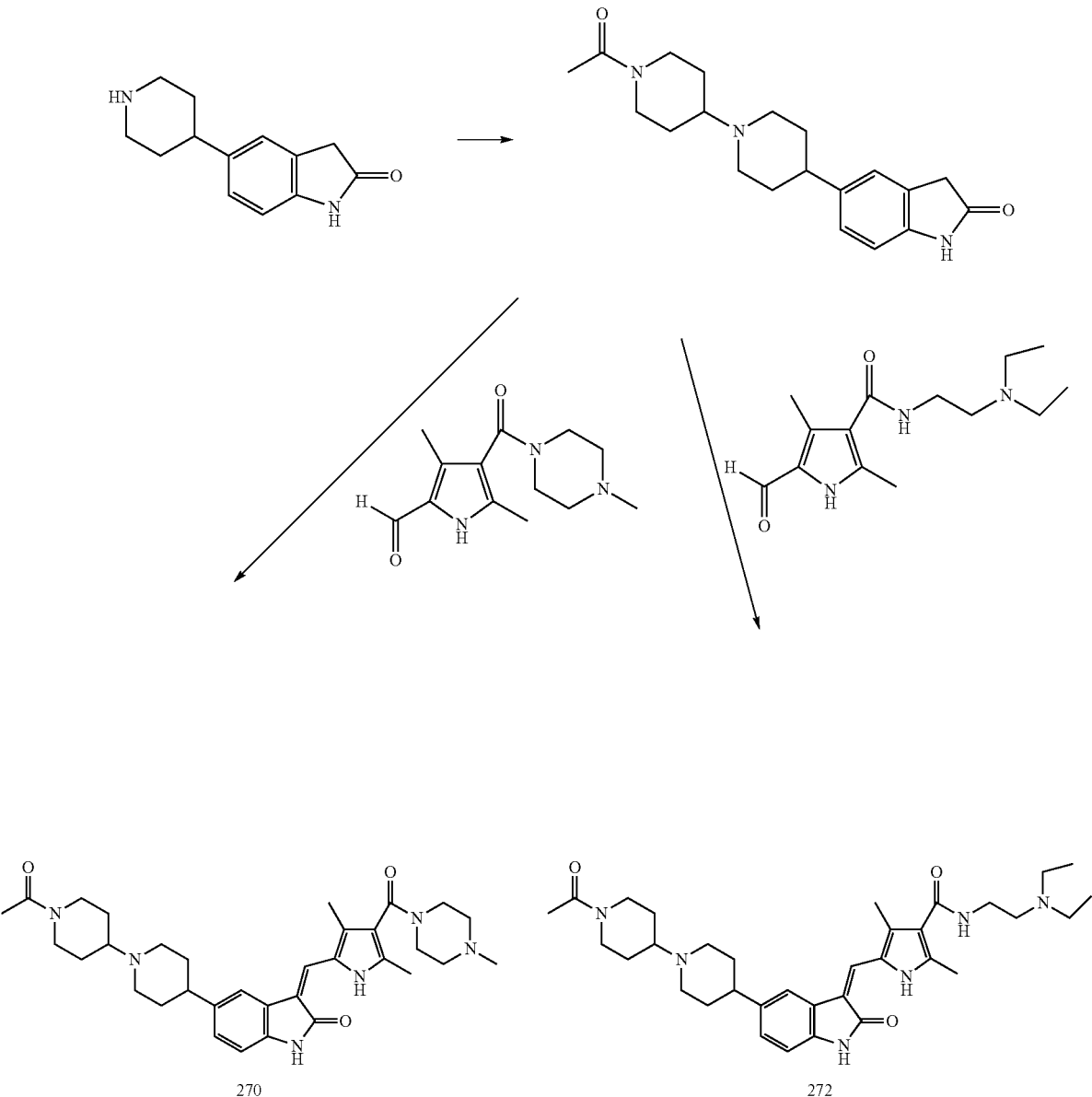
Example 89
Preparation of Compound 271
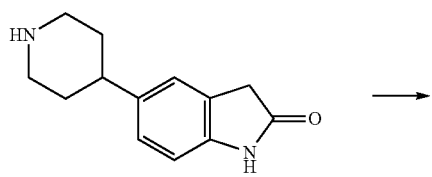

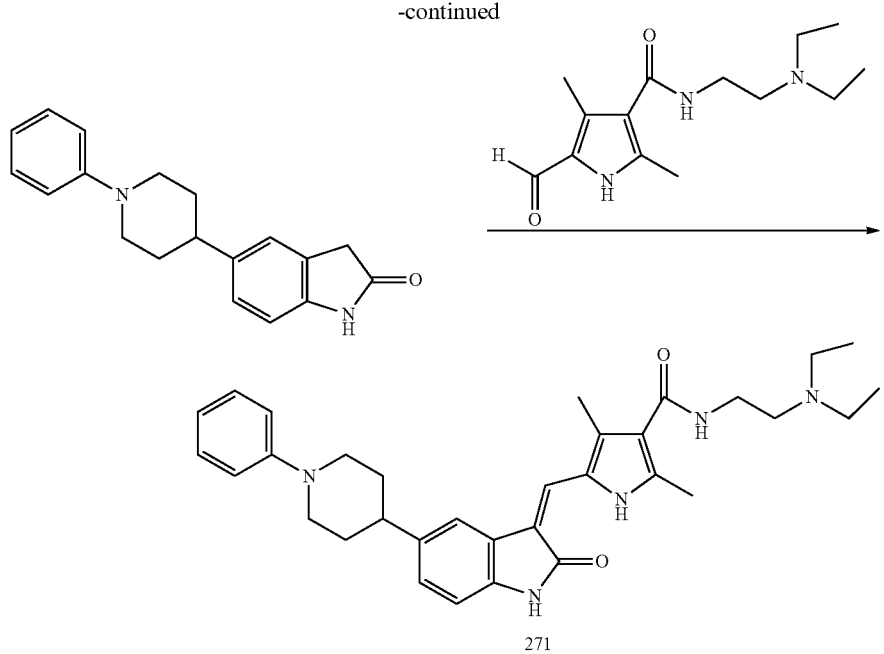

271

Biological Assays

Example 90

Identification of Compounds that Inhibit Kinases

The ability of the Compounds was evaluated for its ability to inhibit certain oncogenic kinases. Cells were treated with each of the compounds for 6 hours. Western blot analysis was performed to determine levels of the phosphorylated forms of ERK and RPS6. It was found that incubation of cells with compounds of the present invention blocked phosphorylation of ERK and RPS6 (FIG. 1).

Example 91

Identification of Compounds that Target Bulk Cancer Cells

Cancer cells were plated at 5000 cells per well in black-walled 96 well plates in 100 uL per well of complete media (DMEM, 10% FBS, 1% penicillin/streptomycin). Cells were treated with each of the compounds 24 hours after plating with a dose curve of the indicated compounds in triplicate wells. Cells were harvested 72 hours after drug treatment and viability was determined using CellTiter-Glo assay (Promega) as directed by the manufacturer. The results are shown in Table 1.

TABLE 1

|     | FaDu IC50 (uM) | A549 IC50 (uM) | ACHN IC50 (uM) |
|-----|----------------|----------------|----------------|
| 42  | 7.73           | 16.03          |                |
| 45  | 3.32           | 29.63          | 4.80           |
| 46  | 23.24          |                |                |
| 47  | 4.22           | 16.01          | 13.96          |
| 48  | 7.80           | 4.88           | 21.96          |
| 49  | 6.69           |                |                |

TABLE 1-continued

|     | FaDu IC50 (uM) | A549 IC50 (uM) | ACHN IC50 (uM) |
|-----|----------------|----------------|----------------|
| 50  | 6.16           |                |                |
| 51  | 1.81           |                |                |
| 52  | 2.15           |                |                |
| 53  | 8.23           |                |                |
| 102 | 7.41           |                |                |
| 127 | 5.17           | 4.75           | 5.83           |
| 128 | 1.61           | 8.60           | 2.12           |
| 129 | 3.04           |                |                |
| 130 | 3.14           | 1.48           | 3.86           |
| 131 | 4.43           | 3.97           | 4.65           |
| 132 | 3.73           |                |                |
| 133 | 7.27           |                |                |
| 134 | 2.77           |                | 3.94           |
| 135 | 0.66           |                |                |
| 136 | 1.50           | 4.29           | 3.02           |
| 233 | 5.02           |                |                |
| 234 | 6.29           | 26.34          | 11.61          |
| 235 | 5.30           | 1.96           | 3.20           |
| 236 | 11.29          | 5.41           | 15.16          |
| 237 | 23.94          |                |                |
| 238 | 4.74           |                | 7.60           |
| 239 | 25.42          |                |                |
| 241 | 21.11          | 10.14          | 12.82          |
| 242 | 6.76           |                |                |
| 243 | 4.44           |                |                |
| 244 | 87.64          |                |                |
| 245 | 9.73           |                | 12.20          |
| 246 | 12.10          |                |                |
| 247 | 7.35           |                | 63.30          |
| 250 | 14.06          | 48.90          | 83.90          |
| 251 | 6.25           | 5.35           | 2.28           |
| 252 | 3.62           | 6.91           | 3.40           |
| 253 | 3.01           | 2.94           | 6.57           |
| 254 | 4.55           |                |                |
| 256 | 17.29          |                |                |
| 257 | 1.11           | 5.09           | 1.60           |
| 258 | 7.56           | 21.50          | 14.90          |
| 260 | 39.21          |                |                |
| 261 | 1.51           | 1.12           | 1.75           |
| 262 | 3.62           | 3.15           | 2.83           |
| 263 | 2.41           | 3.64           | 3.31           |
| 264 | 99.81          |                |                |

TABLE 1-continued

| | FaDu IC50 (uM) | A549 IC50 (uM) | ACHN IC50 (uM) |
|---|---|---|---|
| 265 | 62.66 | | |
| 267 | 6.47 | | |
| 268 | 64.79 | | |
| 271 | 1.89 | | |
| 272 | 22.27 | | |
| 273 | 6.15 | 27.31 | 10.40 |
| 277 | 2.51 | | |
| 278 | 4.22 | 5.99 | 2.32 |
| 279 | 18.28 | 9.94 | 11.26 |
| 280 | 7.87 | 8.55 | 4.25 |
| 281 | 3.05 | | |
| 282 | 11.20 | | |
| 283 | 5.35 | | |
| 284 | 6.74 | | 4.73 |
| 285 | 6.58 | | 7.16 |
| 286 | 2.84 | 29.20 | 3.54 |
| 287 | 5.79 | | |
| 291 | 3.55 | 7.49 | 2.97 |
| 294 | 5.34 | | 20.60 |
| 295 | 5.54 | | |
| 296 | 1.18 | 4.74 | 1.64 |
| 297 | 23.70 | | |
| 298 | 14.30 | | |
| 299 | 0.51 | 1.72 | 1.24 |
| 300 | 3.67 | 18.90 | na |
| 301 | 2.53 | 2.53 | 1.64 |
| 303 | 7.98 | | 5.67 |
| 304 | 3.09 | 4.30 | 3.66 |
| 306 | 46.90 | | |
| 307 | 3.68 | | |
| 308 | 0.70 | 3.06 | 1.38 |
| 309 | 24.80 | | |
| 310 | 2.42 | 0.72 | 6.75 |
| 311 | 1.77 | | 1.27 |
| 332 | 7.87 | | 5.31 |
| 333 | 1.62 | 1.29 | 1.56 |
| 334 | 1.58 | 1.34 | 1.64 |
| 335 | 21.76 | 16.32 | 1.16 |
| 338 | 0.69 | 0.70 | 0.52 |
| 339 | 18.62 | 9.61 | 12.60 |
| 340 | 5.48 | 2.86 | 12.62 |
| 341 | 11.36 | 7.28 | 10.67 |
| 343 | 3.85 | 1.11 | 2.48 |
| 344 | 7.57 | 17.25 | 1.44 |
| 345 | 6.14 | 11.15 | 8.74 |
| 346 | 1.66 | 9.19 | 3.61 |
| 347 | 3.42 | 14.75 | 0.29 |
| 348 | 64.39 | | 14.59 |
| 349 | 20.25 | | 34.61 |
| 350 | | | 37.82 |
| 351 | 21.12 | 9.39 | 18.81 |
| 352 | 67.77 | | |
| 353 | 49.26 | | |
| 355 | 13.52 | 40.03 | 0.39 |
| 357 | | | 24.92 |
| 358 | | | 0.83 |
| 359 | 11.37 | 4.00 | 14.91 |
| 360 | | | 9.91 |
| 361 | 27.98 | 10.07 | 7.42 |
| 362 | 5.16 | 5.55 | 4.12 |
| 365 | 25.18 | 8.73 | |
| 366 | 2.59 | 5.79 | |
| 367 | 35.47 | | |
| 368 | 17.51 | | |
| 370 | 55.99 | | |
| 371 | 5.31 | 18.03 | |
| 373 | 8.67 | 7.06 | |

Example 92

Identification of Compounds that Target Cancer Stem Cells

Cancer Stem Cell (CSC) cultures were initiated from heterogenous cancer cell lines. Briefly, cancer cell cultures were trypsonized and collected in centrifuge tubes. Cells were then pelleted by centrifugation, media removed, and cells resuspended in phosphate buffered saline (PBS). Cells were then pelleted again, and the process repeated for a total of three PBS washes. Cells were subsequently resuspended in CSC media (DMEMF-12, 1×B27 supplement (Life Technologies), 0.4% BSA, 10 ng/ml EGF, 10 ng/ml FGF). Following resuspension, cells were passed through a 40 uM cell strainer to obtain a single cell suspension. Cells were then plated in 100 mm dishes coated with 0.5% Agar to prevent cell attachment. Cells were then allowed to grow for 5-7 days to allow CSC sphere formation.

CSC spheres that were a minimum of passage 2 were dissociated with Accutase and filtered through a 40 uM cell strainer before counting to remove any cell clumps. CSCs were then plated at 1000 cells per well in black-walled 96 well plates that have been coated in 0.5% Agar in 100 uL per well of CSC media. CSCs were then allowed to grow for 72 hours. CSC cultures were then treated with a dose curve of the indicated compounds in triplicate wells. CSC cultures were harvested 72 hours after drug treatment and viability determined using CellTiter-Glo assay (Promega) as directed by the manufacturer. The results are shown in Table 2.

TABLE 2

| | FaDu CSC IC50 (uM) | A549 CSC IC50 (uM) | ACHN CSC IC50 (uM) |
|---|---|---|---|
| 42 | 3.41 | | |
| 45 | 1.00 | | |
| 46 | 15.56 | | |
| 47 | 2.57 | | |
| 48 | 4.09 | | |
| 49 | 12.82 | | |
| 50 | 2.80 | | |
| 51 | 2.24 | | |
| 52 | 11.30 | | |
| 53 | 21.51 | | |
| 102 | 6.60 | | |
| 127 | 3.61 | | |
| 128 | 2.70 | | |
| 129 | 2.54 | | |
| 130 | 1.28 | | |
| 131 | 1.24 | | |
| 132 | 1.39 | | |
| 133 | 2.03 | | |
| 134 | 2.34 | | |
| 135 | 17.63 | | |
| 136 | 2.52 | | |
| 233 | 0.66 | 3.73 | 0.19 |
| 234 | 1.01 | 1.22 | 0.39 |
| 235 | 1.40 | 1.57 | 0.28 |
| 236 | 2.53 | 4.19 | 0.50 |
| 238 | 1.20 | | |
| 239 | 1.16 | | |
| 240 | 14.78 | | |
| 241 | 2.60 | 11.03 | 0.23 |
| 242 | 37.24 | | |
| 243 | 1.64 | | |
| 244 | 30.52 | | |
| 245 | 41.51 | | |
| 246 | 9.35 | | |
| 247 | 27.58 | 0.35 | |
| 248 | 2.38 | | |
| 250 | 0.23 | | |
| 251 | 0.60 | 4.83 | |
| 252 | 0.31 | 4.49 | |
| 253 | 3.46 | | |
| 254 | 11.48 | | |
| 255 | 48.22 | | |
| 256 | 4.96 | | |
| 257 | 0.28 | 4.32 | |
| 258 | 1.21 | 5.76 | |
| 259 | 1.60 | | |
| 261 | 0.65 | 0.62 | 0.97 |

TABLE 2-continued

| | FaDu CSC IC50 (uM) | A549 CSC IC50 (uM) | ACHN CSC IC50 (uM) |
|---|---|---|---|
| 262 | 1.10 | 2.01 | 0.40 |
| 263 | 8.16 | | |
| 264 | 23.15 | | |
| 265 | 33.67 | | |
| 267 | 18.84 | | |
| 268 | 41.90 | | |
| 271 | 1.30 | | |
| 273 | 9.05 | | |
| 276 | 20.16 | | |
| 277 | 0.83 | | |
| 278 | 0.31 | 12.20 | |
| 279 | 3.40 | 10.51 | 0.69 |
| 280 | 1.98 | 0.45 | |
| 282 | 4.75 | | |
| 283 | 2.17 | | |
| 284 | 2.90 | | |
| 285 | 3.00 | | |
| 286 | 1.31 | 4.90 | |
| 287 | 1.31 | | |
| 289 | 18.18 | | |
| 291 | 8.09 | | 1.65 |
| 292 | 1.60 | | 0.50 |
| 295 | 13.23 | | |
| 296 | 0.27 | 4.28 | |
| 298 | 40.82 | | |
| 299 | 0.05 | 2.53 | |
| 300 | 0.24 | 11.70 | |
| 301 | 1.65 | | |
| 302 | 8.94 | | |
| 303 | 12.61 | | |
| 304 | 1.41 | 8.25 | |
| 307 | 1.33 | | |
| 308 | 1.85 | 6.99 | |
| 309 | 7.82 | | |
| 310 | | 32.50 | |
| 311 | 4.88 | 4.21 | |
| 332 | 6.49 | | |
| 333 | 0.43 | 0.88 | 0.09 |
| 334 | 0.48 | 1.70 | 0.05 |
| 336 | 5.62 | | |
| 338 | 0.22 | 2.48 | |
| 339 | 6.74 | 4.80 | 6.16 |
| 340 | 6.56 | | 5.05 |
| 341 | 0.21 | 3.73 | 0.56 |
| 342 | | 1.65 | |
| 343 | 3.53 | 8.74 | 4.23 |
| 344 | 2.50 | 2.31 | 2.91 |
| 345 | 6.32 | 0.90 | |
| 346 | 22.06 | 7.18 | 28.90 |
| 347 | | 2.60 | 9.21 |
| 349 | 4.09 | 1.42 | 2.52 |
| 350 | | 0.80 | |
| 351 | 11.95 | 22.11 | 2.68 |
| 352 | 3.07 | | |
| 355 | | 13.17 | |
| 356 | 5.04 | | 4.08 |
| 357 | 4.49 | | na |
| 358 | 2.91 | | 1.60 |
| 359 | 3.13 | 26.66 | 4.04 |
| 361 | 4.57 | 35.71 | 1.24 |
| 362 | 0.76 | 2.04 | 0.10 |

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:
1. A compound of Formula I,

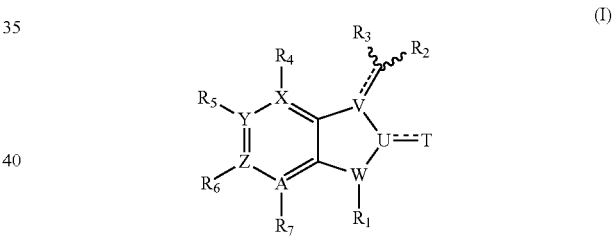

or an enantiomer, diastereomer, tautomer, or pharmaceutically acceptable salt or solvate thereof, wherein:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is monocyclic or bicyclic heterocycle or substituted heterocycle;

$R_3$ is hydrogen, alkyl or substituted alkyl, cycloalkyl or substituted cycloalkyl, heterocycle or substituted heterocycle, aryl or substituted aryl, halogen, $OR_a$, $C(=O)R_a$, $C(=O)OR_a$, $NR_aR_b$, or $S(=O)_2NR_aR_b$;

$R_4$, $R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, S(=O)₂NR$_b$R$_c$, P(=O)₂NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)₂NR$_b$R$_c$, NR$_d$P(=O)₂NR$_b$R$_c$, NR$_b$C(=O)R$_a$, or NR$_b$P(=O)₂R$_e$;

T is O, S or R$_a$;

U and V are each independently carbon;

W is N;

X, Y, Z, and A are each independently carbon;

with the provision that one of R$_4$, R$_5$, R$_6$, and R$_7$ is

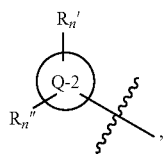

wherein:

Q-2 is a 5- or 6-membered aromatic or non-aromatic ring or ring system having at least one ring carbon atom substituted with a heteroatom selected from N, O and S;

R$_n$' and R$_n$" are each independently hydrogen, halogen, cyano, nitro, trihalomethyl, OCF$_3$, alkyl or substituted alkyl, heterocycle or substituted heterocycle, aryl or substituted aryl, or OR$_a$;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are each independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

2. The compound of claim 1, having the Formula (I-a)

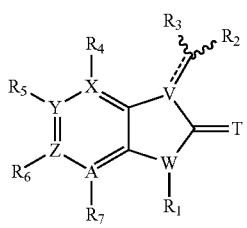

wherein T is O or S.

3. The compound of claim 2, wherein the compound is selected from the group consisting of:

(i) a compound wherein T is O, (I-b)

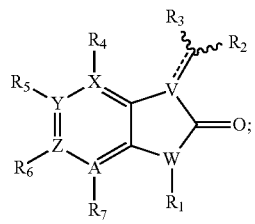

(ii) a compound wherein V is carbon, (I-c)

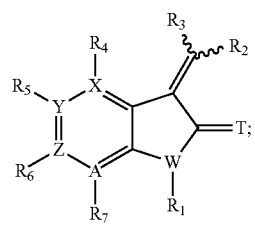

(iii) a compound wherein W is N, (I-d)

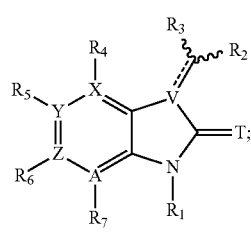

(iv) a compound wherein T is O, (I-e)

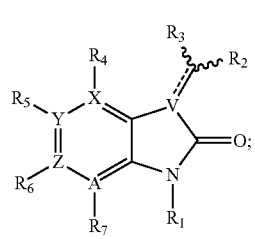

and
(v) a compound wherein T is O,

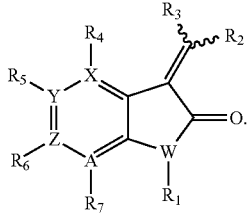
(I-f)

4. The compound of claim 1, wherein T is O,

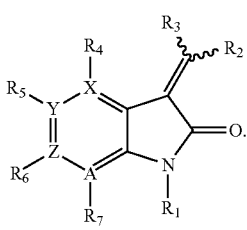
(I-g)

5. The compound of claim 4, wherein $R_2$ is

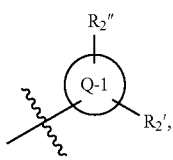

wherein:
Q-1 is a 5- or 6-membered aromatic or non-aromatic ring or ring system having at least one ring carbon atom substituted with a heteroatom selected from N, O and S;
$R_2'$ and $R_2''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$.

6. A compound of Formula II,

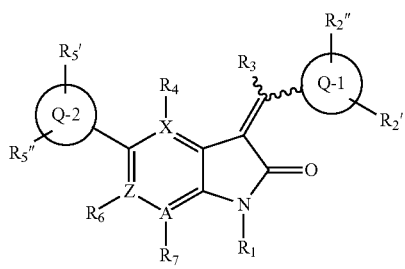
(II)

or an enantiomer, diastereomer, tautomer, or pharmaceutically acceptable salt or solvate thereof, wherein:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, $OR_a$, $C(=O)R_a$, $C(=O)OR_a$, $NR_aR_b$, or $S(=O)_2NR_aR_b$;

$R_4$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Z, and A are each independently carbon;

Q-1 and Q-2 are each independently a 5- or 6-membered aromatic or non-aromatic ring or ring system optionally having at least one ring carbon atom substituted with a heteroatom selected from N, O and S;

$R_2'$ and $R_2''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2R_e$;

$R_5'$ and $R_5''$ are each independently hydrogen, halogen, cyano, nitro, $CF_3$, $OCF_3$, alkyl or substituted alkyl, heterocycle or substituted heterocycle, aryl or substituted aryl, or $OR_a$;

wherein:

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are each independently hydrogen, alkyl or substituted alkyl, cycloalkyl or substituted cycloalkyl, heterocycle or substituted heterocycle, aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

7. The compound of claim 6, wherein the compound is selected from the group consisting of:

(i) a compound having the formula:

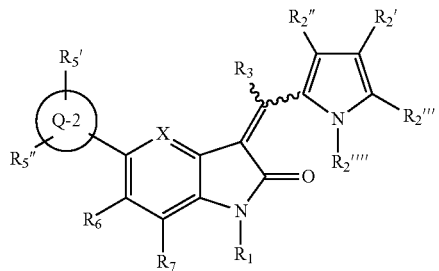

(II-b)

wherein:

X is C;

$R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$; and $R_2'''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

(ii) a compound having the formula:

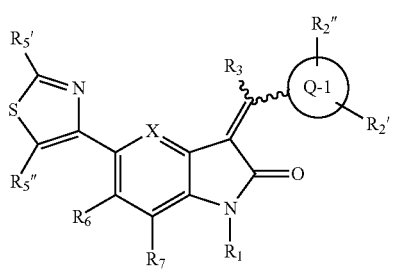

(II-c)

wherein X is C; and (iii) a compound having the formula:

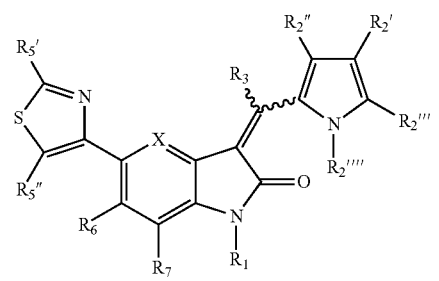

(II-d)

wherein:

X is C;

$R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2R_e$; and $R_2'''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

8. The compound of claim 7, wherein $R_2'''$ is H, each of $R_2''$ and $R_2'''$ is H, or $R_2''$ is H and each of $R_2'$ and $R_2'''$ is H.

9. A compound of Formula III,

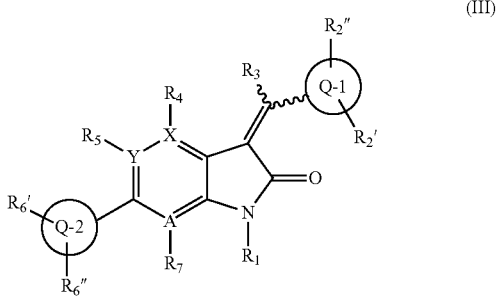

(III)

or an enantiomer, diastereomer, tautomer, or pharmaceutically acceptable salt or solvate thereof, wherein:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, $OR_a$, $C(=O)R_a$, $C(=O)OR_a$, $NR_aR_b$, or $S(=O)_2NR_aR_b$;

$R_4$, $R_5$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Y, and A are each independently carbon;

Q-1 and Q-2 are each independently a 5- or 6-membered aromatic or non-aromatic ring or ring system optionally having at least one ring carbon atom substituted with a heteroatom selected from N, O and S;

$R_2'$ and $R_2''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_6'$ and $R_6''$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein:

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are each independently hydrogen, alkyl or substituted alkyl, cycloalkyl or substituted cycloalkyl, heterocycle or substituted heterocycle, aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

10. The compound of claim 9, wherein the compound is selected from the group consisting of:

(i) a compound having the formula:

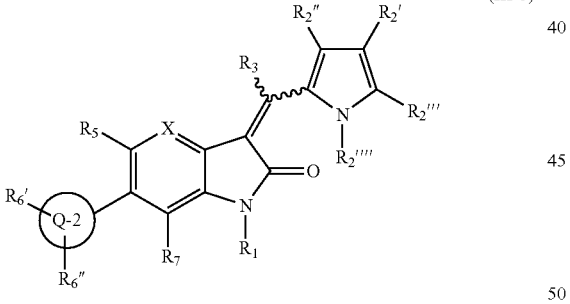

(III-b)

wherein

X is C;

$R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)2R_e$; and $R_2'''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

(ii) a compound having the formula:

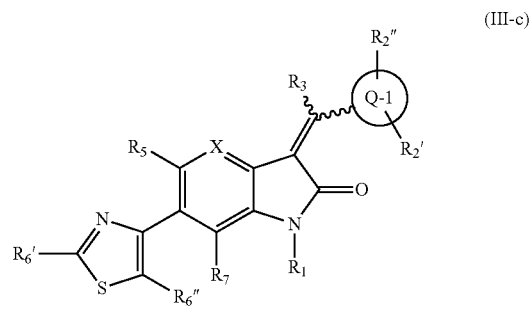

(III-c)

wherein X is C; and (iii) a compound having the formula:

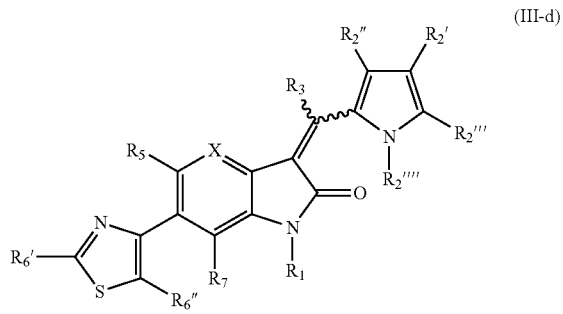

(III-d)

wherein

X is C or N;

$R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$; and $R_2'''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

11. The compound of claim 10, wherein $R_2'''$ is H, each of $R_2''$ and $R_2'''$ is H, or $R_2'$ is H and each of $R_2''$ and $R_2'''$ is H.

12. A compound of Formula IV,

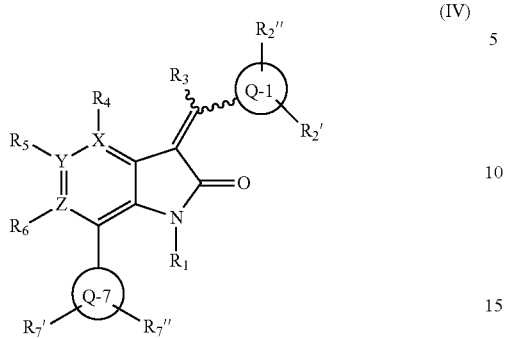

or an enantiomer, diastereomer, tautomer, or pharmaceutically acceptable salt or solvate thereof, wherein:
- $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;
- $R_3$ is hydrogen, alkyl or substituted alkyl, cycloalkyl or substituted cycloalkyl, heterocycle or substituted heterocycle, aryl or substituted aryl, halogen, $OR_a$, $C(=O)R_a$, $C(=O)OR_a$, $NR_aR_b$, or $S(=O)_2NR_aR_b$;
- $R_4$, $R_5$, and $R_6$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;
- X, Y, and Z are each independently carbon;
- Q-1 and Q-2 are each independently a 5- or 6-membered aromatic or non-aromatic ring or ring system optionally having at least one ring carbon atom substituted with a heteroatom selected from N, O and S;
- $R_2'$ and $R_2''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;
- $R_7'$ and $R_7''$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein:
- $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;
- $R_b$, $R_c$, and $R_d$ are each independently hydrogen, alkyl or substituted alkyl, cycloalkyl or substituted cycloalkyl, heterocycle or substituted heterocycle, aryl or substituted aryl, or said $R_b$ and $R_c$ together with the N to which they are bonded optionally form a heterocycle or substituted heterocycle; and
- $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

13. The compound of claim 12, wherein the compound is selected from the group consisting of:

(i) a compound having the formula:

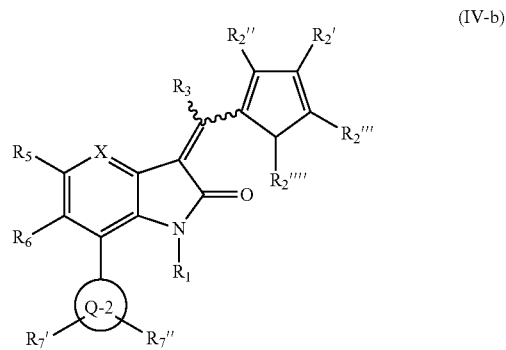

wherein:
- X is C;
- $R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$; and
- $R_2''''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

(ii) a compound having the formula:

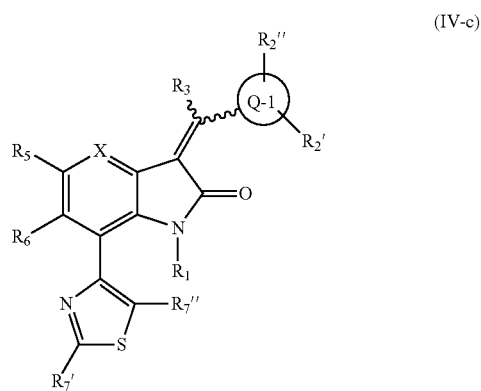

wherein X is C; and
(iii) a compound having the formula:

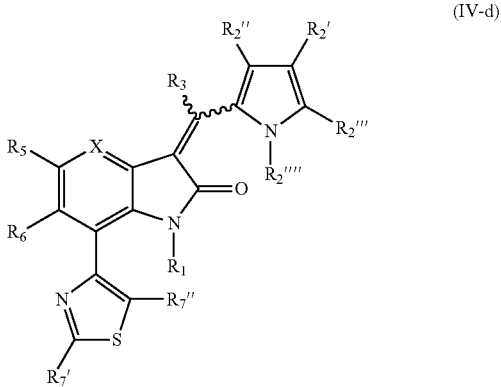

(IV-d)

wherein:
X is C;
$R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$; and
$R_2''''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

14. The compound of claim 13, wherein $R_2'''$ is H, each of $R_2''$ and $R_2'''$ is H, or $R_2''$ is H and each of $R_2'$ and $R_2'''$ is H.

15. A compound of Formula V,

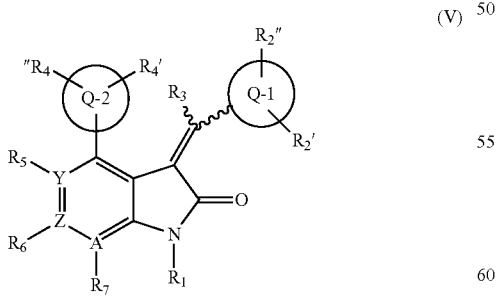

(V)

or an enantiomer, diastereomer, tautomer, or pharmaceutically acceptable salt or solvate thereof, wherein:
$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, $OR_a$, $C(=O)R_a$, $C(=O)OR_a$, $NR_aR_b$, or $S(=O)_2NR_aR_b$;

$R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

Y, Z and A are each independently carbon;

Q-1 and Q-2 are each independently a 5- or 6-membered aromatic or non-aromatic ring or ring system optionally having at least one ring carbon atom substituted with a heteroatom selected from N, O and S;

$R_2'$ and $R_2''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_7'$ and $R_7''$ are each independently hydrogen, halogen, cyano, nitro, trihalomethyl, $OCF_3$, alkyl or substituted alkyl, heterocycle or substituted heterocycle, aryl or substituted aryl, or $OR_a$;

wherein:

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are each independently hydrogen, alkyl or substituted alkyl, cycloalkyl or substituted cycloalkyl, heterocycle or substituted heterocycle, aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

16. The compound of claim 15, wherein the compound is selected from the group consisting of:

(i) a compound having the formula:

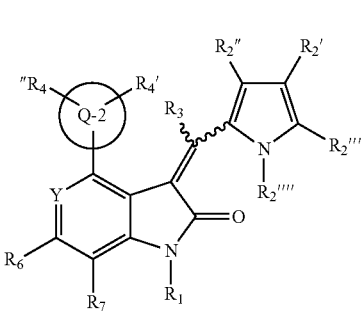

(V-b)

wherein:

Y is C;

$R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$; and $R_2''''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

(ii) a compound having the formula:

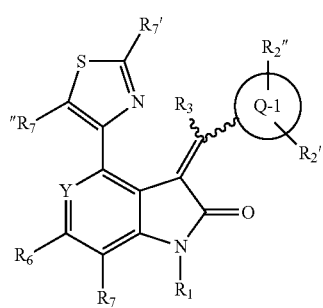

(V-c)

wherein Y is C; and (iii) a compound having the formula:

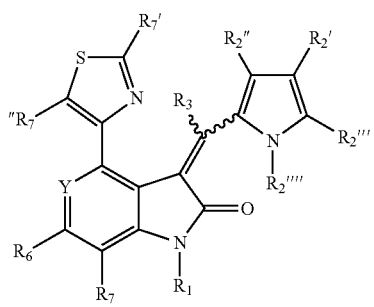

(V-d)

wherein:

Y is C;

$R_2'$, $R_2''$, and $R_2'''$ are each independently hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$; and $R_2''''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$.

17. The compound of claim 16, wherein $R_2''''$ is H, each of $R_2''$ and $R_2'''$ is H, or $R_2'''$ is H and each of $R_2''$ and $R_2'''$ is H.

18. A pharmaceutical composition comprising a compound of claim 1, or a pharmaceutically acceptable salt, ester or pro-drug thereof, and a pharmaceutically acceptable excipient, carrier, or diluent.

* * * * *